(12) United States Patent
Ragusky et al.

(10) Patent No.: US 9,928,478 B2
(45) Date of Patent: Mar. 27, 2018

(54) METHOD AND SYSTEM FOR TRACKING EQUIPMENT

(71) Applicant: Medical Solutions, Inc., Chantilly, VA (US)

(72) Inventors: Stephanie Ragusky, Chantilly, VA (US); Alex Cabrera, Bristow, VA (US); Durward I. Faries, Jr., Las Vegas, NV (US)

(73) Assignee: Medical Solutions, Inc., Chantilly, VA (US)

( * ) Notice: Subject to any disclaimer, the term of this patent is extended or adjusted under 35 U.S.C. 154(b) by 200 days.

(21) Appl. No.: 14/182,750

(22) Filed: Feb. 18, 2014

(65) Prior Publication Data

US 2014/0236615 A1    Aug. 21, 2014

Related U.S. Application Data

(60) Provisional application No. 61/766,269, filed on Feb. 19, 2013.

(51) Int. Cl.
*G06Q 10/08* (2012.01)
*G06F 19/00* (2018.01)

(52) U.S. Cl.
CPC ......... *G06Q 10/087* (2013.01); *G06F 19/328* (2013.01)

(58) Field of Classification Search
None
See application file for complete search history.

(56) References Cited

U.S. PATENT DOCUMENTS

| | | |
|---|---|---|
| 5,810,771 A | 9/1998 | Blomquist |
| 6,553,336 B1 | 4/2003 | Johnson et al. |
| 6,566,631 B2 | 5/2003 | Faries, Jr. |
| 6,850,252 B1 | 2/2005 | Hoffberg |
| 6,987,452 B2 | 1/2006 | Yang |
| 7,031,778 B2 | 4/2006 | Hsiung et al. |
| 7,041,941 B2 | 5/2006 | Faries, Jr. et al. |
| 7,276,675 B2 | 10/2007 | Faries, Jr. et al. |
| 7,307,245 B2 | 12/2007 | Faries, Jr. et al. |
| 7,328,654 B2 | 2/2008 | Shei |
| 7,417,205 B2 | 8/2008 | Faries, Jr. et al. |
| 8,659,420 B2 * | 2/2014 | Salvat, Jr. ............ G01S 5/0027 235/384 |
| 2003/0135388 A1 | 7/2003 | Martucci et al. |
| 2003/0216831 A1 | 11/2003 | Hart et al. |
| 2004/0247016 A1 | 12/2004 | Faries, Jr. et al. |
| 2005/0060165 A1 * | 3/2005 | Knight .................. G06Q 10/08 705/22 |
| 2005/0222933 A1 | 10/2005 | Wesby |
| 2006/0291533 A1 | 12/2006 | Faries, Jr. et al. |
| 2007/0000910 A1 | 1/2007 | Faries, Jr. et al. |

(Continued)

OTHER PUBLICATIONS

PCT International Search Report and Written Opinion, PCT/US2014/016869, Jun. 27, 2014, 10 pages.

*Primary Examiner* — Paul Danneman
(74) *Attorney, Agent, or Firm* — Edell, Shapiro & Finnan, LLC

(57) ABSTRACT

Present invention embodiments include a tool to track manufactured and other products from cradle to grave. This includes tracking the history of locations where equipment has been placed, loaned, evaluated, stored, and sold. The system includes Return Authorization (RA) and Complaints for equipment and parts.

33 Claims, 98 Drawing Sheets

FIG.1

(56) References Cited

U.S. PATENT DOCUMENTS

| | | |
|---|---|---|
| 2007/0015975 A1 | 1/2007 | Faries, Jr. et al. |
| 2009/0055215 A1* | 2/2009 | Giraldo ................ G06F 19/327 |
| | | 705/2 |
| 2009/0082726 A1 | 3/2009 | Ogawa |
| 2009/0204462 A1* | 8/2009 | McCue ................ G06Q 10/06 |
| | | 705/37 |
| 2010/0082459 A1 | 4/2010 | Tusa et al. |
| 2010/0108761 A1* | 5/2010 | Nycz ................ G06Q 10/087 |
| | | 235/385 |
| 2011/0030565 A1 | 2/2011 | Shei |
| 2011/0307274 A1 | 12/2011 | Thompson et al. |
| 2012/0265336 A1 | 10/2012 | Mallett et al. |
| 2013/0253952 A1 | 9/2013 | Burke et al. |

\* cited by examiner

USERS/SALES EXECUITVES HOME PAGE

FIG.3 SELECTING SEARCH FROM THE MENU BAR

SEARCH WINDOW

TEXTBOX SEARCH FIELDS EXAMPLE

FIG.5

DROP-DOWN MENU SEARCH FIELDS EXAMPLE

| Serial No | Model | PL Date | PL Type | Current Location | City | Qty | Linked Eq | Equipment Notes |
|---|---|---|---|---|---|---|---|---|
| 2084 | 1058... | 03/27/99 | SOLD | VA001 - Inova Fairfax Hospital | Falls Church | 1 | K24 STD O... #2027 | |
| 2027 | K24 STD O... | 03/27/99 | LOAN | VA001 - Inova Fairfax Hospital | Falls Church | 1 | 1058... #2084 | |
| 6384 | 1058H-S... | 03/19/99 | SOLD | VA001 - Inova Fairfax Hospital | Falls Church | 1 | K24 STD O... #3189 | |
| 3189 | K24 STD O... | 03/19/99 | SOLD | VA001 - Inova Fairfax Hospital | Falls Church | 1 | 1058H-S... #6384 | |

Found 510 Current Equipment devices that matched your request.

Number of Hits

RESULTS GRID FOR SEARCH EQUIPMENT IN VIRGINIA

FIG.7

USING THE RESULTS GRID

| Equipment: 246810-1075HS - 42 | | close or Esc Key |
|---|---|---|
| Serial Number | 246810 | |
| Model | 1075HS - 42 | |
| Mfg Date Code | XXXX | |
| Equipment Condition | N | |
| Linked Equipment | k24.ORT.0.. #1357811 | |
| Equipment Ownership | ORS | |
| SA Expiration | 01/01/0001 | |
| Warranty Expiration | 01/01/0001 | |
| General Ledger | On | |
| Current RA No | | |
| Equipment Notes | | |
| Edit | | |

NOTE: After editing Equipment device, please click the Search button again in the Equipment Page to refresh the results and show the edits.

Placement History

| | PL Date | PL Type | Location | City | Qty | Linked Eq | New Placement | PL Notes |
|---|---|---|---|---|---|---|---|---|
| ✎ | 05/20/10 | NEW | 001ST-STOCK | Chantilly | 1 | k24.ORT.0.. #1357811 | | |

EQUIPMENT DEVICE DETAILS WINDOW

FIG.9

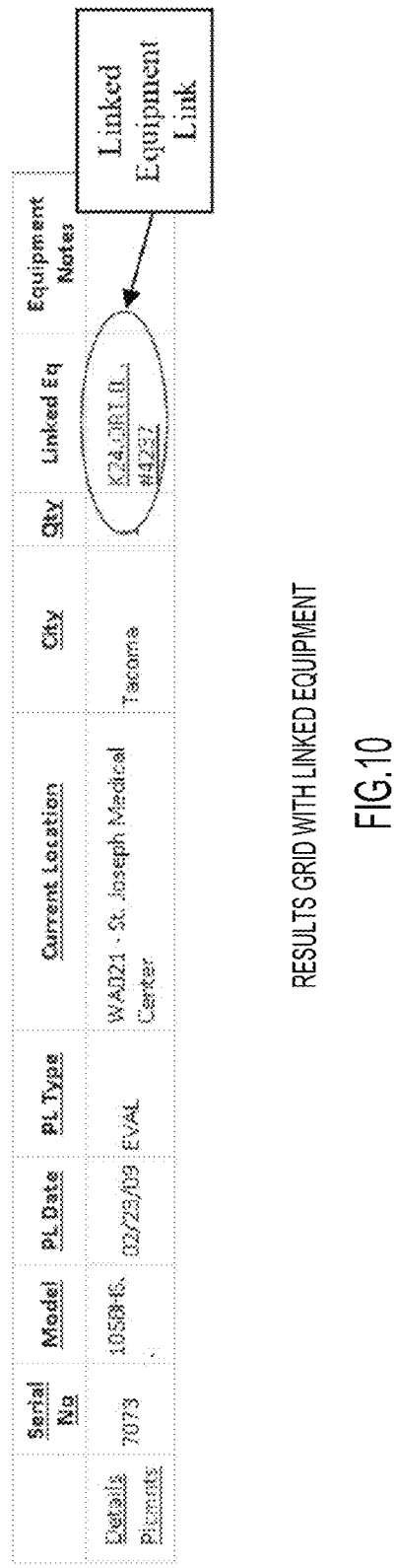
FIG.10 RESULTS GRID WITH LINKED EQUIPMENT

LINKED EQUIPMENT DETAILS

FIG.11

"EXPORT RESULT TO EXCEL" DIALOGUE BOX

SAVING EXPORT RESULTS TO EXCEL SPREADSHEET

ACCESSING RESOURCES

LOCATIONS SEARCH PAGE

FIG.15

Found 68 Locations that matched your search criteria.

| | Loc ID | Loc Name | Loc Class | Territory | City | State | Country | Loc Notes | Status |
|---|---|---|---|---|---|---|---|---|---|
| Details History | VA001 | Inova Fairfax Hospital | Hospital_Customer | VA001 | Falls Church | VA | USA | ACT Script: Name, City Updated on 1/23/2009 ACT Script: Name, City Updated on 1/23/2009 | 1 |
| Details History | VA002 | Bon Secours Memorial Regional Medical Center | Hospital_Customer | VA001 | Mechanicsville | VA | USA | ACT Script: Name, City Updated on 1/23/2009 | 1 |

RESULTS GRID FOR LOCATION SEARCH

FIG.16

LOCATION DETAILS PAGE

FIG. 17

Location: VA001  CLOSE or ESC KEY

Placement History

Below find ALL historical placements ever used for this location.

| PlDate | PlType | Qty | SerialNo | Model | Account | AccountName |
|---|---|---|---|---|---|---|
| 03/17/2009 | SOLD/REPL | 1 | 2017 | 1058 | VA001 | Inova Fairfax Hospital |
| 03/17/2009 | SOLD/REPL | 1 | 4927 | K24.ORT.0 | VA001 | Inova Fairfax Hospital |
| 03/17/2009 | SOLD/REPL | 1 | 4927 | K24.ORT.0 | VA001 | Inova Fairfax Hospital |
| 03/17/2009 | SOLD/REPL | 1 | 2017 | 1058 | VA001 | Inova Fairfax Hospital |
| 03/17/2009 | SOLD | 1 | 2142 | 1058 | VA001 | Inova Fairfax Hospital |
| 03/17/2009 | SOLD | 1 | 2417 | K14.STD.0 | VA001 | Inova Fairfax Hospital |
| 02/25/2009 | EVAL | 1 | 47113 | 2057.D.0 | VA001 | Inova Fairfax Hospital |
| 02/25/2009 | EVAL | 1 | 47118 | 2057.D.0 | VA001 | Inova Fairfax Hospital |
| 02/25/2009 | EVAL | 1 | 43704 | 2094.R.0 | VA001 | Inova Fairfax Hospital |
| 05/20/2008 | EVAL | 1 | 4667 | 2058.D.0 | VA001 | Inova Fairfax Hospital |

LOCATION HISTORY PAGE

FIG.18

PLACEMENT TYPES RESOURCES PAGE

Models Management

Below find all the available Models and the Model Classes. For Status 0: Inactive, 1: Equipment, 2 : Accessory, Contact the System Administrator for deletion of models.

| Catalogue | Model | Configuration | ProductLevel | Model Description | Status |
|---|---|---|---|---|---|
| 2000 Series Warmers | 2038 | | | 3.8 Liter Warming Basin | 0 |
| 2000 Series Warmers | 2038 | D | E | 3.8 Liter Warming Basin, D Version | 1 |
| 2000 Series Warmers | 2038 | DF | | 3.8 Liter Warming Basin - D Version, Foreign | 1 |
| 2000 Series Warmers | 2038 | F | | 3.8 Liter Warming Basin, Foreign | 0 |
| 2000 Series Warmers | 2057 | | | 5.7 Liter Warming Basin/Endoscopic - original | 0 |
| 2000 Series Warmers | 2057 | D | E | 5.7 Liter Warming Basin/Endoscopic Warming, D Version | 1 |
| 2000 Series Warmers | 2057 | DF | | 5.7 Liter Warming Basin/Endoscopic, D Version, Foreign | 1 |

MODELS RESOURCES PAGE

FIG.20

Catalogue Management

Below find all the available Catalogues which are used to group Models. For Status 0: Inactive, 1: Active, deletion of models.

| Catalogue | Catalogue Description | Status |
|---|---|---|
| 2000 Series Warmers | | 1 |
| Accessories | | 1 |
| Auto Slush | | 1 |
| Hush Slush | | 1 |

CATALOGUE RESOURCES PAGE

FIG.21

Territory Management

Below find all the available Territories. Note: The Sales Exec Username must be an exact match. of Territories.

| Territory | Region | Sales Exec Username | Territory Description |
|---|---|---|---|
| ✏ AS001 | WESTERN | kmontanez | astone |
| ✏ AZ001 | WESTERN | khilgenberg | |
| ✏ BB001 | SOUTH CENTRAL | mllaneza | |
| ✏ CC001 | NORTH-CENTRAL | ccordell | |

TERRITORIES RESOURCES PAGE

FIG.22

Regions Management

Below find all the available Regions. Contact the System Administrator for deletion or updates of Regions.

Important: The Sales Manager Username must be an exact match.

| | Region | Reg Mngr Username | Sales Admin | Region Description |
|---|---|---|---|---|
| ✏ | N/A | N/A | | |
| ✏ | NORTH-CENTRAL | Jeff Marcus | Kristin Linthicum | |
| ✏ | NORTHEAST | notjog | Kristin Linthicum | |
| ✏ | SOUTH CENTRAL | John Soldevila | Kristin Linthicum | |

REGIONS RESOURCES PAGE

FIG.23

REPORTS ON MAIN MENU

REPORT ENGINE PARAMETERS EXAMPLE

FIG. 25

SAMPLE REPORT

FIG. 26

NEW EQUIPMENT ENTRY SCREEN

FIG. 27

CREATING LINKED EQUIPMENT

LINKED EQUIPMENT

| Equipment 246810-1075HS-42. | | close or Esc Key |
|---|---|---|
| Serial Number | 246810 | |
| Model | 1075HS - 42. | |
| Mfg Date Code | XXXX | |
| Equipment Condition | N | |
| Linked Equipment | K24.ORT.0. #1357911 | |
| Equipment Ownership | ORS | |
| SA Expiration | 01/01/0001 | |
| Warranty Expiration | 01/01/0001 | |
| General Ledger | On | |
| Current RA No | | |
| Equipment Notes | | |
| Edit | | |

NOTE: After editing Equipment device, please click the Search button again in the Equipment Page to refresh the results and show the edits.

Placement History

| | PL Date | PL Type | Location | City | Qty | Linked Eq | New Placement | PL Notes |
|---|---|---|---|---|---|---|---|---|
| ✏ | 05/20/10 | NEW | 001ST-STOCK | Chantilly | 1 | K24.ORT.0. #1357911 | | |

SELECTING DETAILS TO REVIEW LINKED EQUIPMENT INFORMATION

FIG.30

LINKED Equipment close or Esc Key

| | |
|---|---|
| Serial Number | 1357911 |
| Model | K24.ORT.O.. |
| Mfg Date Code | XXX |
| Equipment Condition | N |
| Linked Equipment | 1075HS - 42 . #246810 |
| Equipment Ownership | OPS |
| SA Expiration | 01/01/0001 |
| Warranty Expiration | 01/01/0001 |
| General Ledger | On |
| Current RA No | |
| Equipment Notes | |
| Edit | |

NOTE: After editing Equipment device, please click the Search button again in the Equipment Page to refresh the results and show the edits.

Placement History

New Placement

| PL Date | PL Type | Location | City | Qty | Linked Eq | PL Notes |
|---|---|---|---|---|---|---|
| 05/2010 | NEW | 001ST-STOCK | Chantilly | 1 | 1075HS - 42 . #246810 | |

Edit Linked Equipment

LINKED EQUIPMENT LINK

FIG.31

UNLINKING EQUIPMENT

UNLINKING EQUIPMENT CONTINUED

FIG. 34

SELECTING EQUIPMENT DEVICES FOR PLACEMENT

ENTERING NEW PLACEMENT INFORMATION

ALTERNATE PLACEMENTS FUNCTIONALITY

"DELETING" EQUIPMENT DEVICES

MANAGING LOCATIONS

EDIT LOCATIONS PAGE

FIG.39

CREATE NEW LOCATION

Found 1 Locations that matched your search criteria.

| Loc ID | Loc Name | Loc Class | Territory | Region | City | State | Country | Loc Not |
|---|---|---|---|---|---|---|---|---|
| VA001 / Details History | Inova Fairfax Hospital | Customer | VA001 | NORTH EASTERN | Falls Church | VA | USA | .ACT Script: Name Updated on 1/23/: Script: Name, City 1/23/2009 |

Color Coded Status on Location ID

EA STATUS INDICATOR IN LOCATION

FIG.41

CREATING EAs

EA DETAILS FORM

ADDING EQUIPMENT INFORMATION TO EA DETAILS

LOCATION DETAILS PAGE WITH EA INFORMATION

FIG. 45

EDITING PLACEMENT TYPES

CREATING A NEW PLACEMENT TYPE

Models Management

Below find all the available Models and the Model Classes. For Status 0: Inactive, 1: Equipment, 2: Accessory. Contact the System Administrator for deletion of models.

| Catalogue | Model | Configuration | ProductLevel | Model Description | Status |
|---|---|---|---|---|---|
| 2000 Series Warmers | 2050 | | | 3.8 Liter Warming Basin | 0 |
| 2000 Series Warmers | 2050 | D | | 3.8 Liter Warming Basin, D Version | 1 |
| 2000 Series Warmers | 2050 | DF | m | 3.8 Liter Warming Basin - D version, Foreign | 1 |
| 2000 Series Warmers | 2050 | F | | 3.8 Liter Warming Basin, Foreign | 0 |
| 2000 Series Warmers | 2057 | D | | 5.7 Liter Warming Basin/Endoscopic - original | 0 |
| 2000 Series Warmers | 2057 | D | m | 5.7 Liter Warming Basin/Endoscopic Warming, D Version | 1 |
| 2000 Series Warmers | 2057 | DF | | 5.7 Liter Warming Basin/Endoscopic, D Version, Foreign | 1 |

Save or Cancel Edit Icons

Click to edit Models

EDITING MODELS

FIG.48

CREATING MODELS

FIG.50 EXAMPLES OF MODIFIED EQUIPMENT DEVICES

EDITING CATALOGUES

CREATING CATALOGUES

EDITING TERRITORIES

CREATING TERRITORIES

EDITING REGIONS

CREATING REGIONS

EDITING LOCATION CLASSES

FIG. 58 CREATING A NEW LOCATION CLASS

CREATING A RA

RA PAGE (TOP)

ENTER RETURN AND REPLACEMENT EQUIPMENT

REASONS FOR RETURN

FIG. 62

RETURN AND REPLACEMENT EQUIPMENT INFORMATION

FIG. 63

From: MSIET_RA_Notifications@warmw.com [mailto:MSIET_RA_Notifications@warmw.com]
Posted At: Friday, February 04, 2011 3:59 PM
Posted To: Customer Service
Conversation: Create Packing Slip for MSI RA #: 110011 EqT V. 3.2-MSI
Subject: Create Packing Slip for MSI RA #: 110011 EqT V. 3.2-MSI RA #110011 Shipment to Account VA-042: Inova Fair Oaks Hospital Shipping Method: FedEx 3rd Day Saver
-------Shipping Address--------
Test
Test
Fairfax, VA 12345
-------Devices--------
Model: TEMP3.7000.G  Replacement Type: Permanent  Comments: Include K-780

For more information review RA: http://test.ossolutions.us/QA/NewRA.aspx?RAID=110011

Thanks, for any questions please email: stagusky

E-MAIL TO CUSTOMER SERVICE REPLACEMENT EQUIPMENT

FIG.64

ADDING EQUIPMENT TO RA

REPLACEMENT EQUIPMENT TABLE IN RA

FIG.65B

RELATING NEW PLACEMENT TO RA

FIG.66

RA STATUS UPDATE

Status: Pending

Ship Method:
INCOMPLETE
Active
Partial Ret
Closed
Pending
CANCELLED
Test

RA Type: Equipment

...wer

Inova Fairfax Hospi

Department:

Account:

Address:

MANUAL UPDATE OF RA STATUS

FIG.68

MAIN MENU BAR QUALITY MENU ITEMS

CREATING A DRAPE RA

RETURNED DRAPES GRID

FIG.71

CREATING A PART RA

FIG. 72A

Returned Parts

| | ID | Part # | Lot # | Qty | Reason for Return | Ret Date | Adt Info | Comments | Complaint |
|---|---|---|---|---|---|---|---|---|---|
| ✏ | | 2324 | | 0 | ▼ | | ▣ | | |

Email Customer Service | Create Complaint

Replacement Parts

| | ID | Model | Qty | Part Serial # | Sent Date | Comments | Complaint |
|---|---|---|---|---|---|---|---|
| ✏ | | 2324 | 1 | | | | ✕ |

RETURN AND REPLACEMENT PARTS GRID

FIG.72B

RA SEARCH PAGE

RA SEARCH RESULTS GRID

FIG. 75

Returned Equipment

| | ID | Model | Serial # | Qty | Reason for Return | Ret Date | Adt Info | Ownership | Comments |
|---|---|---|---|---|---|---|---|---|---|
| ✎ | 200 | 2038 STD.G. | 1307 | 1 | Recheck and Re-inventory | | | ORS | |
| ✎ | 201 | 2038 STD.G. | 1364 | 1 | Recheck and Re-inventory | | | ORS | |
| ✎ | 217 | 2038 O.B. | 4119 | 1 | Controller/Display Error Code | 06/02/10 | | ORS | Stands Returns |
| ▣ | | | | | | | | | |

Accessories / Stands

Accessories Returns

| | ID | Part # | Lot # | Qty | Reason for Return | Ret Date | Adt Info | Comments | Compl |
|---|---|---|---|---|---|---|---|---|---|
| ✎ | 439 | S-22 | 00 | 1 | Return to inventory | | | | |
| ▣ | | | | | | | | | |

ACCESSORIES RETURNS

FIG.76

SEARCH COMPLAINTS

COMPLAINTS PAGE (TOP)

FIG. 79

COMPLAINT FORM (BOTTOM)

FIG. 80

CREATE COMPLAINT EQUIPMENT

FIG.81

TOP PORTION OF COMPLAINT FORM

FIG.82

BOTTOM PORTION OF COMPLAINT FORM

FIG.83

COMPLAINT LINK CROSS REFERENCE IN RAs

FIG. 84

CAPA Form Required? No ▾    If YES Form #: [          ]

[Save Changes] [Reset]    [Create RA] [Copy Complaint]

COPY COMPLAINT

FIG.85

Copy Complaint: Enter Model & Serial for Copy
- ● Equipment    Model         Serial
- ○ Drape       [TEMP2.6000 ▾] [6017 ▾]
- ○ Parts                      6017
                               6124
  [Copy Complaint] [Cancel]    6053
                               6062
                               6074

SELECT COPY COMPLAINT TYPE

FIG.86

Summary of Incident:
Sales Rep reports power cord is split but she does not id wrong serial number label showing it as a 1075HS which is a 2038D.

Complaint Notes         ⌵

―――――――――――――――――

Complaint Attachments   ⌵

―――――――――――――――――

COMPLAINT ATTACHMENTS ARROW

FIG.87

ADDING COMPLAINT ATTACHMENTS
FIG.88
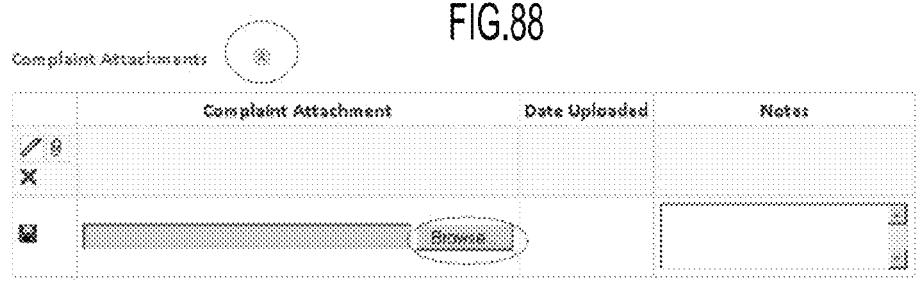
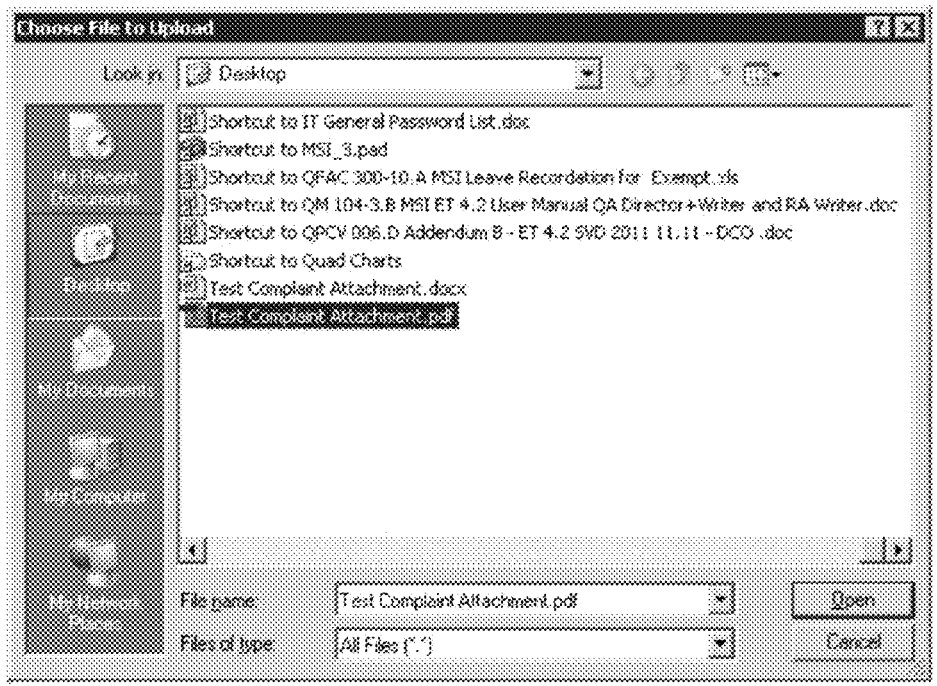
BROWSING TO COMPLAINT ATTACHMENT FILE
FIG.89

COMPLAINTS SEARCH PAGE

FIG.91

SEARCH RESULTS GRID

FIG.92

PRINT QUALITY FORMS MENU

FIG.93

RA FULL FORM PRINT PARAMETERS

FIG. 94

RA FULL FORM PRINT FORM SAMPLE

FIG. 95

UPDATE E-MAIL TO SHIPPING

```
-----Original Message-----
From: ET_RA_Updated@warmiv.com [mailto:ET_RA_Updated@warmiv.com]
Sent: Wednesday, June 09, 2010 12:45 PM
To: Frances Carter
Subject: A Return Authorization #: 100334 had a DEVICE DELETED on
6/9/2010 EqT V. 3.2.0-ORS RA #100334       Account VA001: Inova Fairfax HospitalRA has been
modified please review RA in Equipment tracker:
http://test.orsolutions.us/QA/NewRA.aspx?RAID=100334

Thanks, for any questions please email:
```

E-MAIL NOTIFICATION RA EQUIPMENT DELETED

FIG. 97

Found 30 Complaints that match the selected criteria

| | ID | Date | Model | Serial/Lot | Account | AccountName | Type | Status |
|---|---|---|---|---|---|---|---|---|
| ▶ Edit | 110120 | 10/28/11 | 16N1.B4 | 1117 | CA-330 | Providence Little Company of Mary Medical Center San Pedro | Equipment | Active |
| ☐ Edit | 110119 | 10/28/11 | TEMP2.6000 | 6330 | CA-363 | St. Joseph Hospital | Equipment | Active |
| ▶ Edit | 110118 | 10/28/11 | TEMP2.6000 | 6263 | CA-383 | St. Joseph Hospital | Equipment | Active |
| ☐ Edit | 110117 | 10/26/11 | TEMP3.7000.G | 7053 | CA-158 | Kaiser Permanente Redwood City Medical Center | Equipment | Active |
| ▶ Edit | 110116 | 10/25/11 | TEMP1.9B6L.B | 503309099 | MN-114 | St. John's Hospital | Equipment | Active |

New Complaint    Print

PRINT SELECTED COMPLAINTS OR RAs

FIG. 98

MANAGING QA RESOURCES

| | | |
|---|---|---|
| ✎ Mis-pick | Inventory | Drape |
| ✎ Customer Over Order | Inventory | Drape |
| ✎ Incorrect Part | MFG One | Parts |
| ✎ TBD | MFG One | Parts |
| ✎ test | MFG One | Parts |
| ✎ Order Error - Customer | Inventory | Drape |
| ✎ Not as Expected | Inventory | Equipment |
| ✎ Return to Inventory | Inventory | Equipment |

Reason for Return, Destination, RA Type & Comment

ENTERING NEW REASON FOR RETURN

FIG.100

METHOD AND SYSTEM FOR TRACKING EQUIPMENT

CROSS-REFERENCE TO RELATED APPLICATIONS

This application claims priority to U.S. Provisional Patent Application Ser. No. 61/766,269, entitled "Method and System for Tracking Equipment", and filed Feb. 19, 2013, the disclosure of which is incorporated herein by reference in its entirety.

BACKGROUND

1. Technical Field

Present invention embodiments pertain to equipment tracking and, more specifically, to a computerized tool to track manufactured products from cradle to grave.

2. Discussion of Related Art

Various inventory systems maintain the status of manufactured products within inventory. This provides sellers of the products with various information in order to determine courses of action. For example, when a product has a low quantity within inventory, the product may be ordered or manufactured in preparation for potential future sales. However, information from these types of systems is typically limited to presence of products within the inventory and corresponding quantity information.

SUMMARY

Present invention embodiments include a tool to track manufactured and other products from cradle to grave. This includes tracking the history of locations where equipment has been placed, loaned, evaluated, stored, and sold. The system includes Return Authorization (RA) and Complaints for equipment and parts.

The above and still further features and advantages of the present invention will become apparent upon consideration of the following detailed description of example embodiments thereof, particularly when taken in conjunction with the accompanying drawings, wherein like reference numerals in the various figures are utilized to designate like components.

BRIEF DESCRIPTION OF THE DRAWINGS

FIG. 5 is a schematic illustration of an example graphical user interface screen of a textbox search fields example.

FIG. 7 is a schematic illustration of an example graphical user interface screen of a results grid for a search for equipment in Virginia.

FIG. 9 is a schematic illustration of an example graphical user interface screen of a equipment device details window.

FIG. 10 is a schematic illustration of an example graphical user interface screen of a results grid with linked equipment.

FIG. 11 is a schematic illustration of an example graphical user interface screen of linked equipment details.

FIG. 15 is a schematic illustration of an example graphical user interface screen of a locations search page.

FIG. 16 is a schematic illustration of an example graphical user interface screen of a results grid for a location search.

FIG. 17 is a schematic illustration of an example graphical user interface screen of a location details page.

FIG. 18 is a schematic illustration of an example graphical user interface screen of a location history page.

FIG. 20 is a schematic illustration of an example graphical user interface screen of a models resources page.

FIG. 21 is a schematic illustration of an example graphical user interface screen of a catalogue resources page.

FIG. 22 is a schematic illustration of an example graphical user interface screen of a territories resources page.

FIG. 23 is a schematic illustration of an example graphical user interface screen of a regions resources page.

FIG. 25 is a schematic illustration of an example graphical user interface screen of a report engine search parameters example.

FIG. 26 is a schematic illustration of an example graphical user interface screen of a sample report.

FIG. 27 is a schematic illustration of an example graphical user interface screen for new equipment entry.

FIG. 30 is a schematic illustration of an example graphical user interface screen enabling selection of details to review linked equipment information.

FIG. 31 is a schematic illustration of an example graphical user interface screen providing a link for linked equipment.

FIG. 34 is a schematic illustration of an example graphical user interface screen for selection of equipment devices for placement.

FIG. 39 is a schematic illustration of an example graphical user interface screen for editing locations.

FIG. 41 is a schematic illustration of an example graphical user interface screen providing a status indicator for equipment agreements in a location.

FIG. 45 is a schematic illustration of an example graphical user interface screen of a location details page with equipment agreement information.

FIG. 48 is a schematic illustration of an example graphical user interface screen for editing models.

FIG. 50 is a schematic illustration of an example graphical user interface screen providing examples of modified equipment devices.

FIG. 60 is a schematic illustration of an example graphical user interface screen of an upper portion of an RA page.

FIG. 61 is a schematic illustration of an example graphical user interface screen for entering return and replacement equipment.

FIG. 62 is a schematic illustration of an example graphical user interface screen for providing reasons for a return.

FIG. 63 is a schematic illustration of an example graphical user interface screen providing return and replacement equipment information.

FIG. 64 is a schematic illustration of an example e-mail to customer service concerning replacement equipment.

FIG. 65B is a schematic illustration of an example graphical user interface screen of a replacement equipment table.

FIG. 66 is a schematic illustration of an example graphical user interface screen for relating a new placement to an RA.

FIG. 68 is a schematic illustration of an example graphical user interface screen for manually updating RA status.

FIG. 71 is a schematic illustration of an example graphical user interface screen of a returned drapes grid.

FIG. 72A is a schematic illustration of an example graphical user interface screen for creating a part type RA.

FIG. 72B is a schematic illustration of an example graphical user interface screen of a return and replacement parts grid.

FIG. 73 is a schematic illustration of an example graphical user interface screen of a RA search page.

FIG. 74 is a schematic illustration of an example graphical user interface screen of a RA search results grid.

FIG. 75 is a schematic illustration of an example graphical user interface screen providing details of an RA.

FIG. 76 is a schematic illustration of an example graphical user interface screen for accessories returns.

FIG. 77 is a schematic illustration of an example graphical user interface screen for searching complaints.

FIG. 78 is a schematic illustration of an example graphical user interface screen for highlighting RA's complaint hyperlink.

FIG. 79 is a schematic illustration of an example graphical user interface screen of an upper portion of a complaints page.

FIG. 80 is a schematic illustration of an example graphical user interface screen of the lower portion of the complaints page.

FIG. 81 is a schematic illustration of an example graphical user interface screen for creating a complaint for equipment.

FIG. 82 is a schematic illustration of an example graphical user interface screen of an upper portion of a complaint.

FIG. 83 is a schematic illustration of an example graphical user interface screen of the lower portion of the complaint.

FIG. 84 is a schematic illustration of an example graphical user interface screen for cross-referencing complaint links in RAs.

FIG. 85 is a schematic illustration of an example graphical user interface screen for copying complaints.

FIG. 86 is a schematic illustration of an example graphical user interface screen for selecting a complaint type for copying.

FIG. 87 is a schematic illustration of an example graphical user interface screen of complaint attachments.

FIG. 88 is a schematic illustration of an example graphical user interface screen for adding complaint attachments.

FIG. 89 is a schematic illustration of an example graphical user interface screen for browsing to a complaint attachment file.

FIG. 91 is a schematic illustration of an example graphical user interface screen of a complaints search page.

FIG. 92 is a schematic illustration of an example graphical user interface screen of a Complaint search results grid.

FIG. 93 is a schematic illustration of an example graphical user interface screen of a print Quality forms menu.

FIG. 94 is a schematic illustration of an example graphical user interface screen for searching and printing RA Full Forms.

FIG. 95 is a schematic illustration of an example graphical user interface screen of a RA Full Form print form.

FIG. 97 is a schematic illustration of an example e-mail concerning deletion of RA equipment.

FIG. 98 is a schematic illustration of an example graphical user interface screen for selecting complaints or RAs for printing.

FIG. 100 is a schematic illustration of an example graphical user interface screen for entering a new reason for a return.

DETAILED DESCRIPTION OF EXAMPLE EMBODIMENTS

Figure 1:
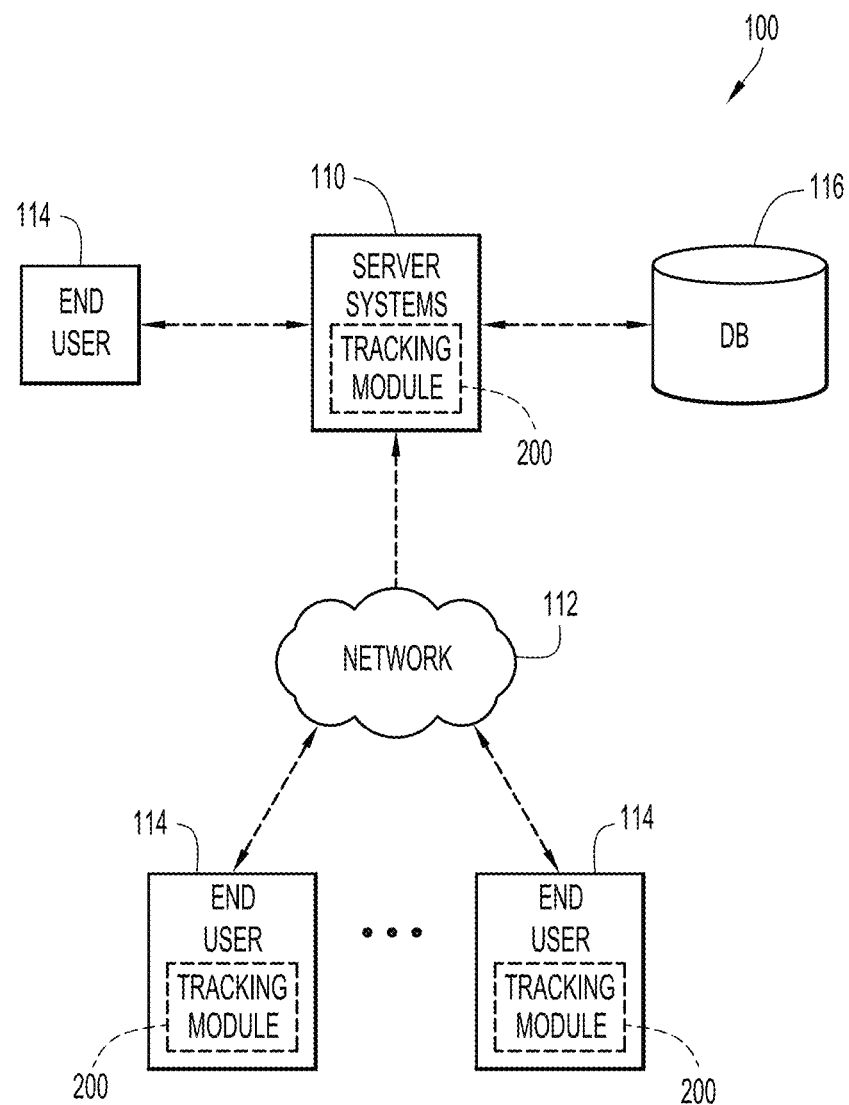
FIG. 1 is a diagrammatic illustration of an example computing environment for use with an embodiment of the present invention.

An example environment for use with present invention embodiments to track equipment or other items is illustrated in FIG. 1. Specifically, environment 100 includes one or more server systems 110, and one or more client or end-user systems 114. The server systems preferably include one or more servers to handle various functions (e.g., security authentication, accounting, sales, electronic mail (e-mail), file operations, print operations, back-up operations, tracking, etc.). In addition, the environment may include various other devices for network communications and other functions (e.g., one or more printers, firewalls, access switches or hubs, routers, etc.).

Server systems 110 and client systems 114 may be remote from each other and communicate over a network 112. The network may be implemented by any number of any suitable communications media (e.g., wide area network (WAN), local area network (LAN), Internet, Intranet, etc.). Alternatively, server systems 110 and client systems 114 may be local to each other, and communicate via any appropriate local communication medium (e.g., local area network (LAN), hardwire, wireless link, Intranet, etc.).

Client systems 114 enable users to interact with server systems 110 to perform equipment tracking and various other related functions (e.g., returns, complaints, etc.). The information (e.g., equipment attributes, locations, customers, etc.) is stored within one or more database systems 116. The database systems may be implemented by any conventional or other databases or storage units, may be local to or remote from server systems 110 and client systems 114, and may communicate via any appropriate communication medium (e.g., local area network (LAN), wide area network (WAN), Internet, hardwire, wireless link, Intranet, etc.). Server systems 110 include tracking and other modules to track equipment as described below. Client systems 114 may present a graphical user (e.g., GUI, etc.) or other interface (e.g., command line prompts, menu or other screens, etc.) to solicit information from users pertaining to the desired information and operations, and provide various reports.

Server systems 110 and client systems 114 may be implemented by any conventional or other computer systems preferably equipped with a display or monitor, a base (e.g., including the processor, memories and/or internal or external communications devices (e.g., modem, network cards, etc.)), optional input devices (e.g., a keyboard, mouse or other input device), and any commercially available and/or custom software (e.g., server/communications software, tracking and other modules, browser/interface software, etc.).

Alternatively, one or more client systems 114 may perform equipment tracking and other operations when operating as a stand-alone unit. In a stand-alone mode of operation, the client system stores or has access to the information, and includes the tracking and other modules to perform the operations. The graphical user (e.g., GUI, etc.) or other interface (e.g., command line prompts, menu or other screens, etc.) solicits information from a corresponding user pertaining to the desired information and operations, and may provide various reports.

Server system 110 includes various modules to process information and perform the tracking and other operations described below. Specifically, server system 110 includes tracking module 200 to track equipment and perform other operations as described below. The tracking and other modules of the server and client systems may be implemented by any combination of any quantity of software and/or hardware modules or units.

Server systems 110 and/or client systems 114 (e.g., via tracking module 200) perform various functions pertaining to tracking of equipment or other items as described below. By way of example only, present invention embodiments may be utilized to track equipment pertaining to medical thermal treatment devices (e.g., warming devices, cooling devices, accessories for these devices (e.g., drapes, etc.), etc.). However, present invention embodiments may be utilized to perform tracking and other functions for any desired items.

Roles and Responsibilities

The following table describes the roles and responsibilities for various users associated with the tracking functions (e.g., tracking module 200). In general, subordinate permissions sets are available to higher hierarchy roles. The exceptions to this policy are Accounting, QA roles, and the Restricted role, which are either independent (as with the Restricted role), or assigned in conjunction with other roles (as with the Accounting role). The roles are defined in the Table I below.

TABLE I

| Role | Departments | Responsibilities |
| --- | --- | --- |
| System Administrator (SA) | IS | Development and Maintenance<br>Views SA only data (backend ID's)<br>Manage and customize Reports<br>Delete Resources as needed (Scripts through SSMS)<br>User accounts setup and maintenance<br>Manage Placement Types, and Location Classes |
| Equipment Tracker Administrator (EqT Admin) | Accounting/Inventory Control | Manage Models<br>Manage Locations<br>Manage Equipment<br>Manage Territories and Regions |

TABLE I-continued

| Role | Departments | Responsibilities |
| --- | --- | --- |
| | | Create and update placement information |
| | | Maintain status levels for all |
| | | Inventory Reconciliation |
| | | Reviews BOL's and Pickup Forms |
| | | Manage Equipment Agreements (EAs) |
| Writer | | Create Equipment |
| | | Place Equipment |
| | | Manage EAs |
| User | QA, Customer Service, Sales Mgmt and Support, MFG Maintenance, Exec Mgmt | Conduct searches Run Reports |
| Regional Managers | Sales | Search information (limited to their region, including Sales Executives Inventory Locations and EAs) Submit Bill of Ladings (BOLs) and Pickup Forms (future) Run Selected Reports |
| Sales Executives | Sales | Search information (limited to their territory, excluding Rep Inventory and EAs) Submit Bill of Ladings (BOLs) and Pickup Forms (future) Run Selected Reports |
| Accountants | Accounting | Use separate web page to run approved accounting reports. Ancillary role with access to functionality not available to any other role. |
| QA Writer | QA | Generate Complaints and RAs related to Complaints. Run Reports Ancillary role with access to functionality not available to any other role. |
| QA Director | QA | Manage Complaints including completing selected fields in Complaints not accessible to any other role. All QA Writer functions |
| QA User | Customer Service, MFG, EqT Admin, and Exec Management (including the Legal Department) | Search and run Reports |
| RA Writer | Shipping, Customer Service Manager | Customer Service creates Drape and Parts RA Shipping creates Equipment RAs Run reports and search Manage RAs |
| Restricted | Customer Service | Run selected reports only. |

I. Users With "User", "Sales Executive" or Similar Roles

The following provides a description pertaining to individuals assigned the "User", "Sales Executives", or similar roles for equipment tracking. Definitions for each of the fields used within the system can be found below.

Accessing Equipment Tracking

The system is accessible using any commercial web browser. All users must be granted access and assigned a security role by the System Administrator. Once access is granted, the system will automatically check your network credentials and allow you to access the site. Users cannot access the system, unless they have logged into the network. The following is an example session to gain access.

Figure 2:
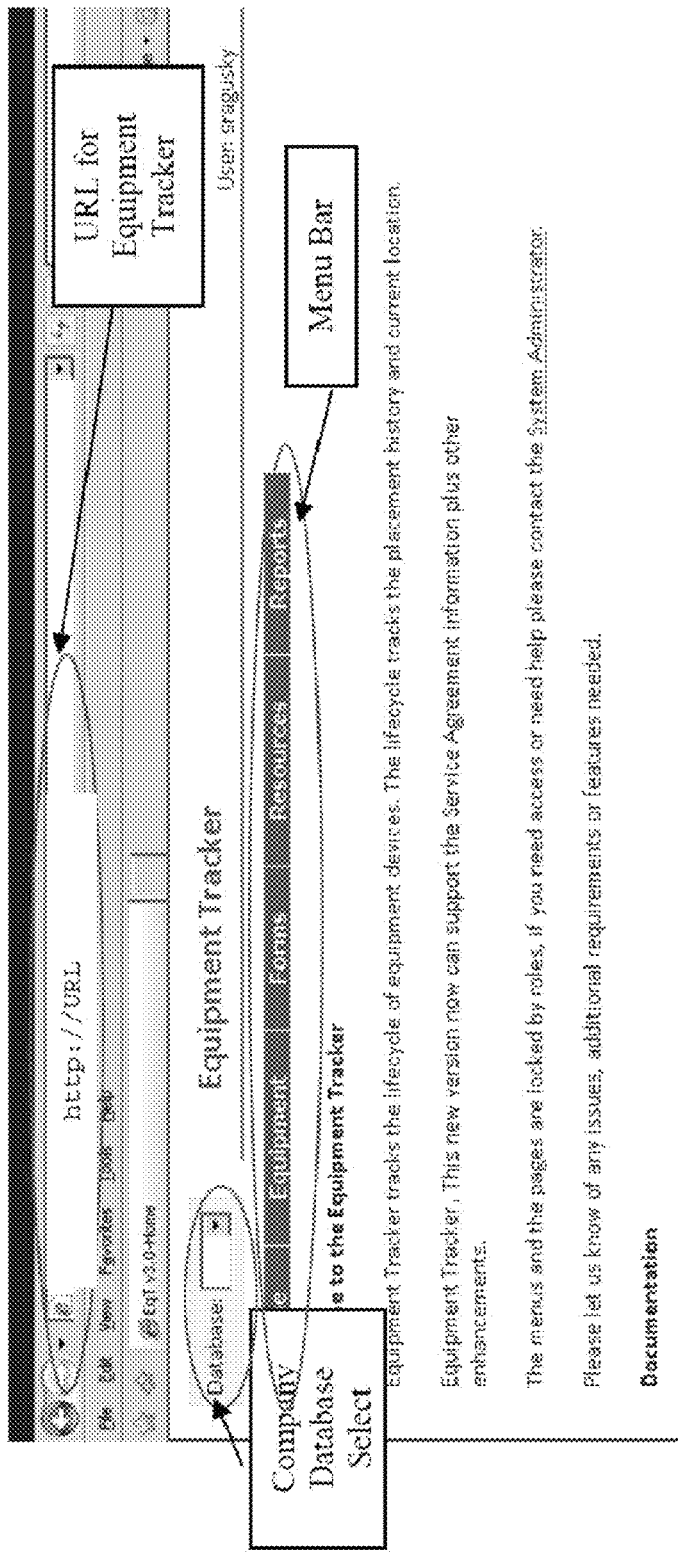
FIG. 2 is a schematic illustration of an example graphical user interface screen of a Users/Sales Executives home page.

1. Open the browser and enter the URL for the system and add to "Bookmarks": The system will open to the Home Page as displayed in FIG. 2—Users/Sales Executives Home Page).

2. Select the Company database. The default is set for specific users. The version of the equipment tracking application and the database being accessed are clearly displayed at the top of the Home Page. The menu bar provides access to all functionality.

Users can "Search" for Equipment Devices and also have access to "Resources", which provide supporting data to assist in queries on Equipment and locations. "Reports" provides access to selected report formats. "Forms" provides access to selected forms.

How to Search for Current Equipment

Generally, Sales Executives can only see equipment located in their territory. Access is not provided to Rep Inventory Locations in order to ensure accurate physical inventories. Regional Sales Managers can see equipment in their Region, including Rep Inventory Locations. The following is an example session to search for equipment.

Figure 3:
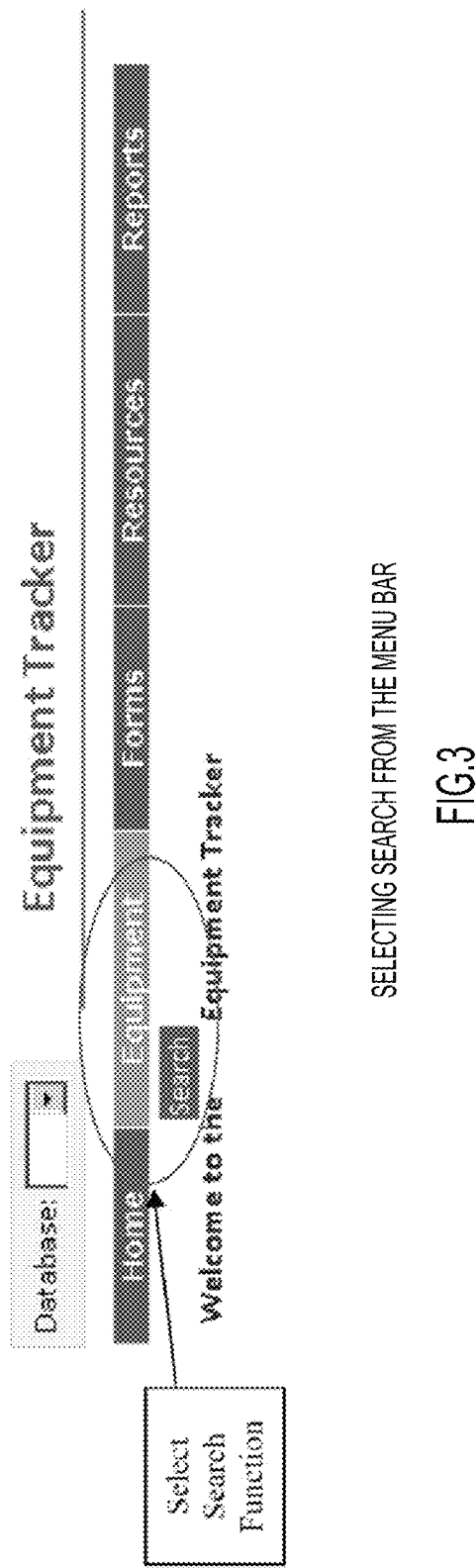
FIG. 3 is a schematic illustration of an example graphical user interface screen to enable a search.

1. Move the cursor over the menu bar "Equipment" button to access the "Search" function. Slide the cursor over the Search button. See FIG. 3—Selecting Search from the Menu Bar.

Figure 4:
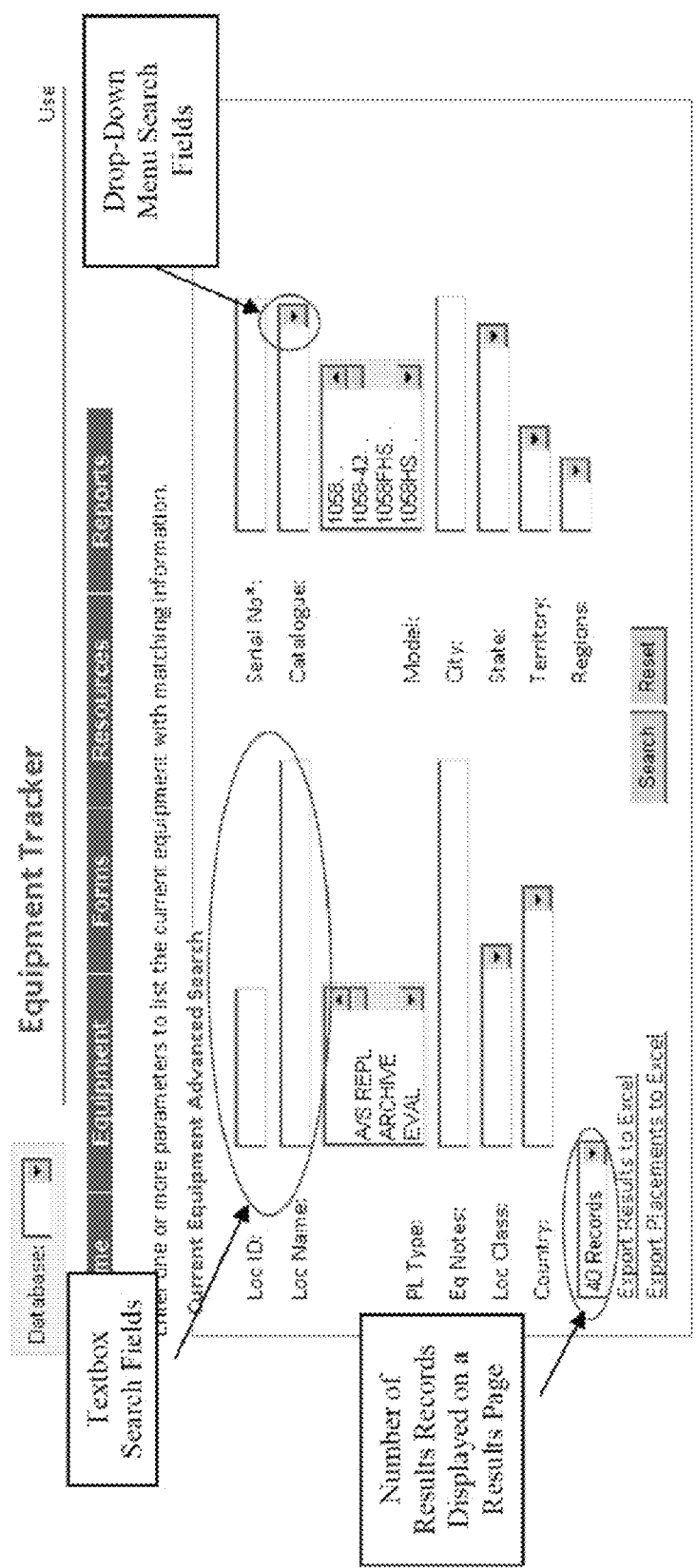
FIG. 4 is a schematic illustration of an example graphical user interface screen of a search window.

2. Selecting the Search button on the menu bar displays the Search Window (See FIG. 4—Search Window). Any combination of fields can be searched to refine the Results.

3. Identify the Fields for your search. There are two types of search fields; Textbox Search Fields and Drop-Down Menu Search Fields. The default is set to 40 records being returned on a page. You can change the number of results by setting the Drop-Down Menu on the bottom left to 100 or 1000. If a search results in more than 40 records, the results will be displayed on multiple pages. Simply click on the page numbers at the bottom of the results grid to move to the next page of results.

Searching on Textbox Search Fields

Figure 5:
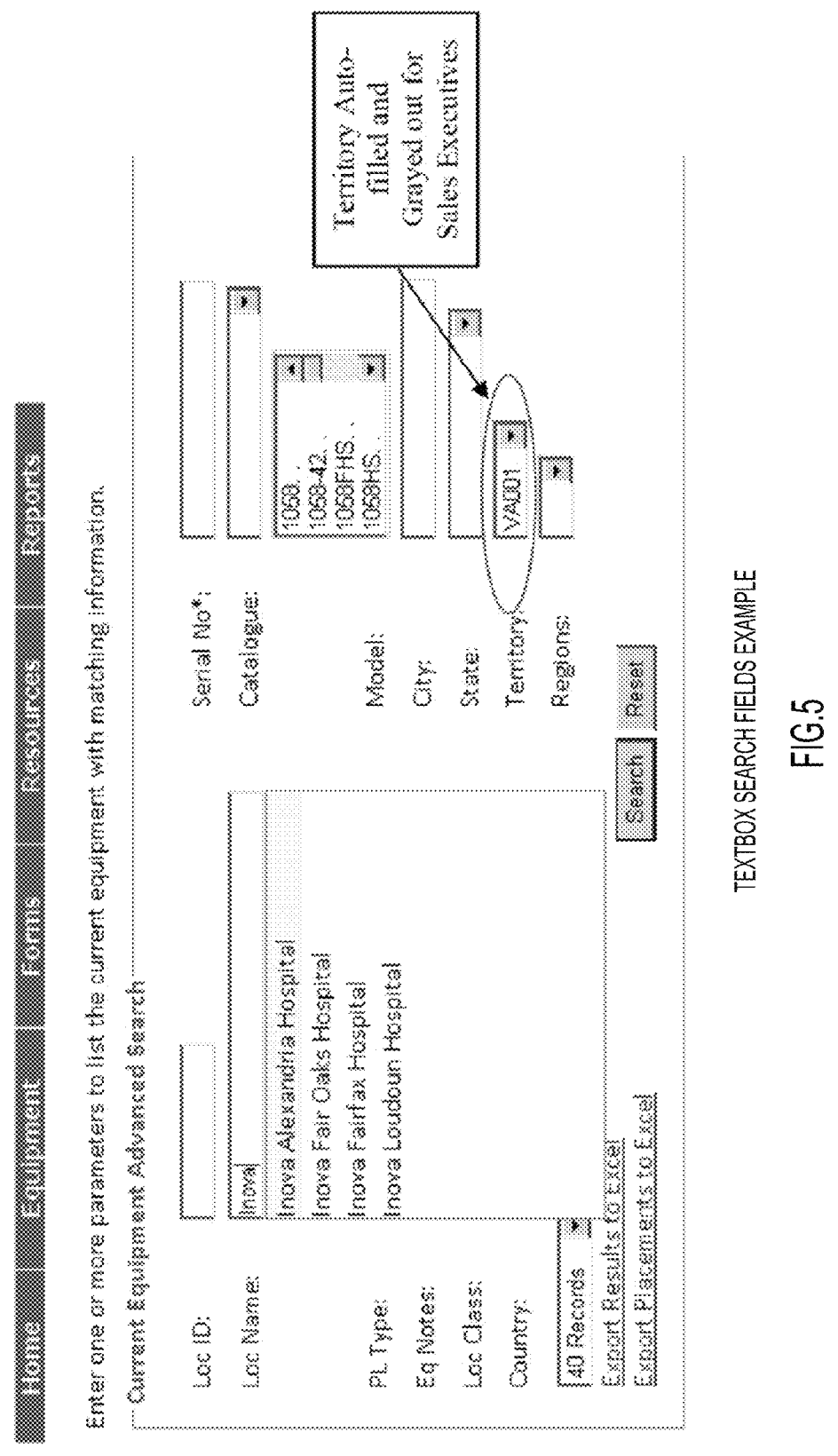

The textbox fields display an "auto complete" list of valid values as you type. You select one of the items in the auto complete list. Refer to FIG. 5. The following is an example session to search for equipment.

4. Click into a Textbox field and type query information.

5. In the Loc Name field begin typing "Inova".

6. The auto complete list will display all current locations with a matching name; continue typing until the item searched for is displayed in the window.

7. Click on the desired item. For this example, click on Inova Fairfax Hospital. This will fill the Loc Name search field. The Territory field is grayed out for Sales Executives, with their Territory filled in. This filters all search results automatically for Sales Execs. All data in the database will be displayed in Textbox Search Fields, but only results pertinent to your Territory will be returned. This same policy applies for Regional Sales Managers and the Region field.

8. Click on the Search Button.

9. All equipment currently located at Inova Fairfax Hospital will be displayed in the Results Grid as shown in FIG. 7. In this example, the Sales Executive for the VA001 Territory (Northern Virginia) is conducting the search.

Searching on Drop-Down Menu Search Fields

Figure 6:
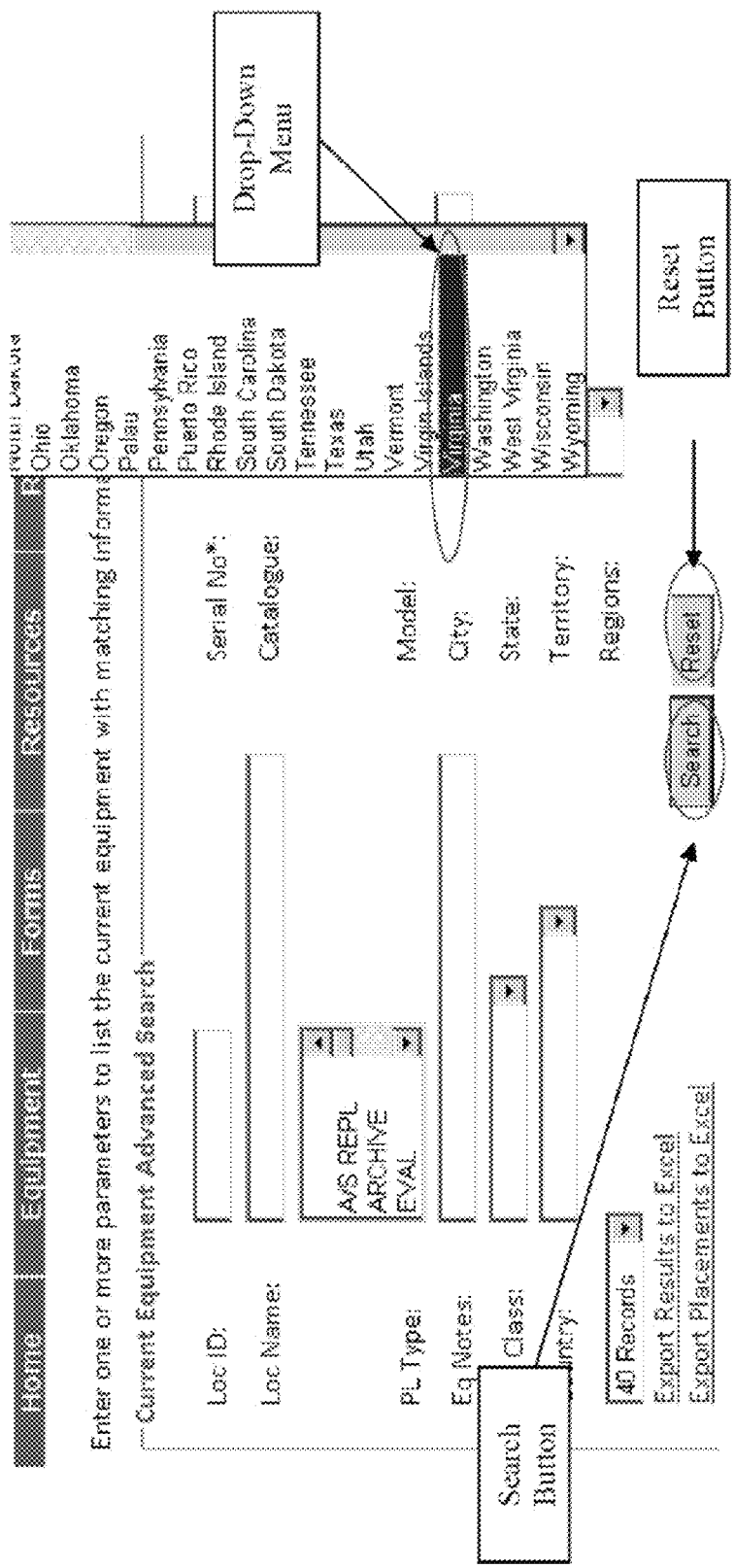
FIG. 6 is a schematic illustration of an example graphical user interface screen of a drop-down menu search fields example.

Fields with arrows provide Drop-Down Menu Search Fields as shown in FIG. 6—Drop-Down Menu Search Fields Example. The following is an example session to search in a Drop-Down Menu field.

10. Click on the arrow of the field and slide the cursor to the desired item or type the first letter, which will move the cursor to the first occurrence in the list.

11. Click on the State field and type "V", this moves the list to Vermont. Scroll down to Virginia and click. You can also quickly type the second letter of the name to select that item (Typing MO will give you Montana). You can also use the up and down arrows to select items.

12. Click on the Search Button.

13. All equipment currently located in the state of Virginia will be returned in the Results Grids shown in FIG. 7—Results Grid for Search Equipment in Virginia.

The Results window will also display the number of records matching the search parameters.

Sales Execs will only see Locations in their Territory rather than every account in the State for those States that are divided among two or more Territories. Clicking the Reset button resets all the search fields to blank.

Using the Search Results Grid

The Search Results are displayed in a Result Grid (See FIG. 8—Using the Results Grid), which allows you to:

Sort.

Review Details and Placements Links. This provides detailed information on the equipment and a history of its placements.

Navigate to detailed information on Linked Equipment.

Export results to an Excel spreadsheet.

Sorting Results Grids

Figure 8:
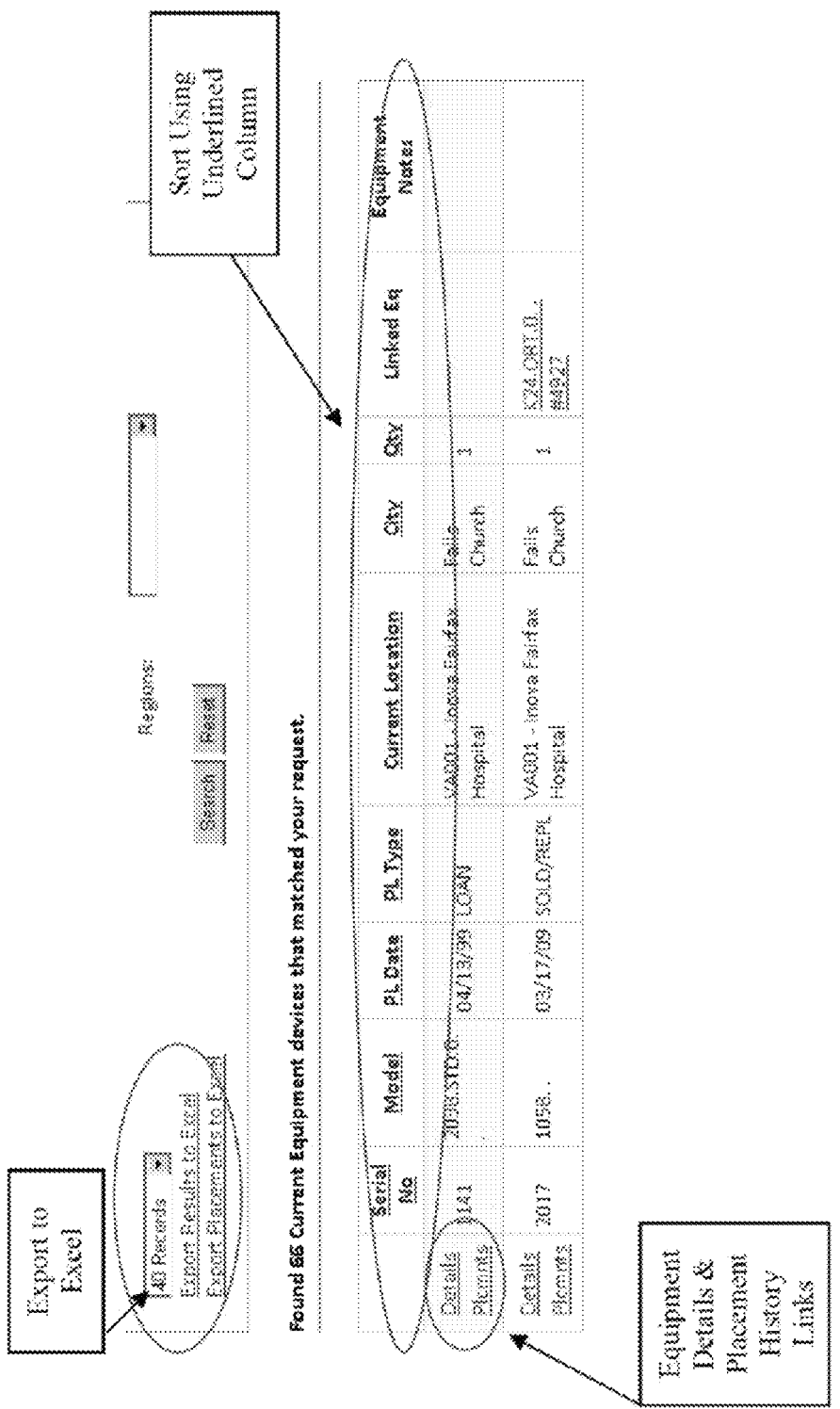
FIG. 8 is a schematic illustration of an example graphical user interface screen showing use of a results grid.

Results Grids can be sorted by clicking on any underlined column header (See FIG. 8). Clicking the header will toggle between ascending and descending order.

Drilling Down in Results Grids

Additional details are available for each Equipment device listed in the Search Results (See FIG. 8). This includes Equipment Details, Placement History, and information on Linked Equipment.

Equipment Details

The "Details" link provides additional data on an individual equipment device (See FIG. 9—Equipment Device Details Window). The following is an example session.

1. Click on the Details Link.

2. The detailed information is displayed in a table.

Information on Manufacturing Date Codes, Equipment Condition, and Notes will be populated based on new Manufacturing procedures and as required.

On/Off GL indicates if the equipment is on or off the General Ledger.

SA Expiration (Service Agreement) and Warranty Expiration Dates are also tracked here and apply to SOLD equipment devices.

This information is also being populated.

The "01/01/0001" in these fields indicated there is no Warranty or SA in effect or the information needs to be entered.

3. Click on "close" to return to the Results Grid.

Placement History information is also displayed on the Equipment Details page. Placement History identifies all the locations where the Equipment has been placed since its manufacture.

Placement History

Placement History can also be obtained for Equipment by clicking on the Plcmnts link. When you click on the Placements Link, the same Results Grid, as shown in FIG. 9—Equipment Device Details Window, will appear at the BOTTOM of the Results Grid Page. No Equipment Details will be provided. The total number of placements for the selected Equipment is identified above the Placement History information.

Linked Equipment

Equipment can be linked to other devices, which is documented by using Linked Equipment. Users can readily identify equipment links and easily navigate to Equipment details without having to search the database again. The following is an example session.

1. Click on the Linked Equipment Link (See FIG. 10—Results Grid with Linked Equipment).

Figure 11:
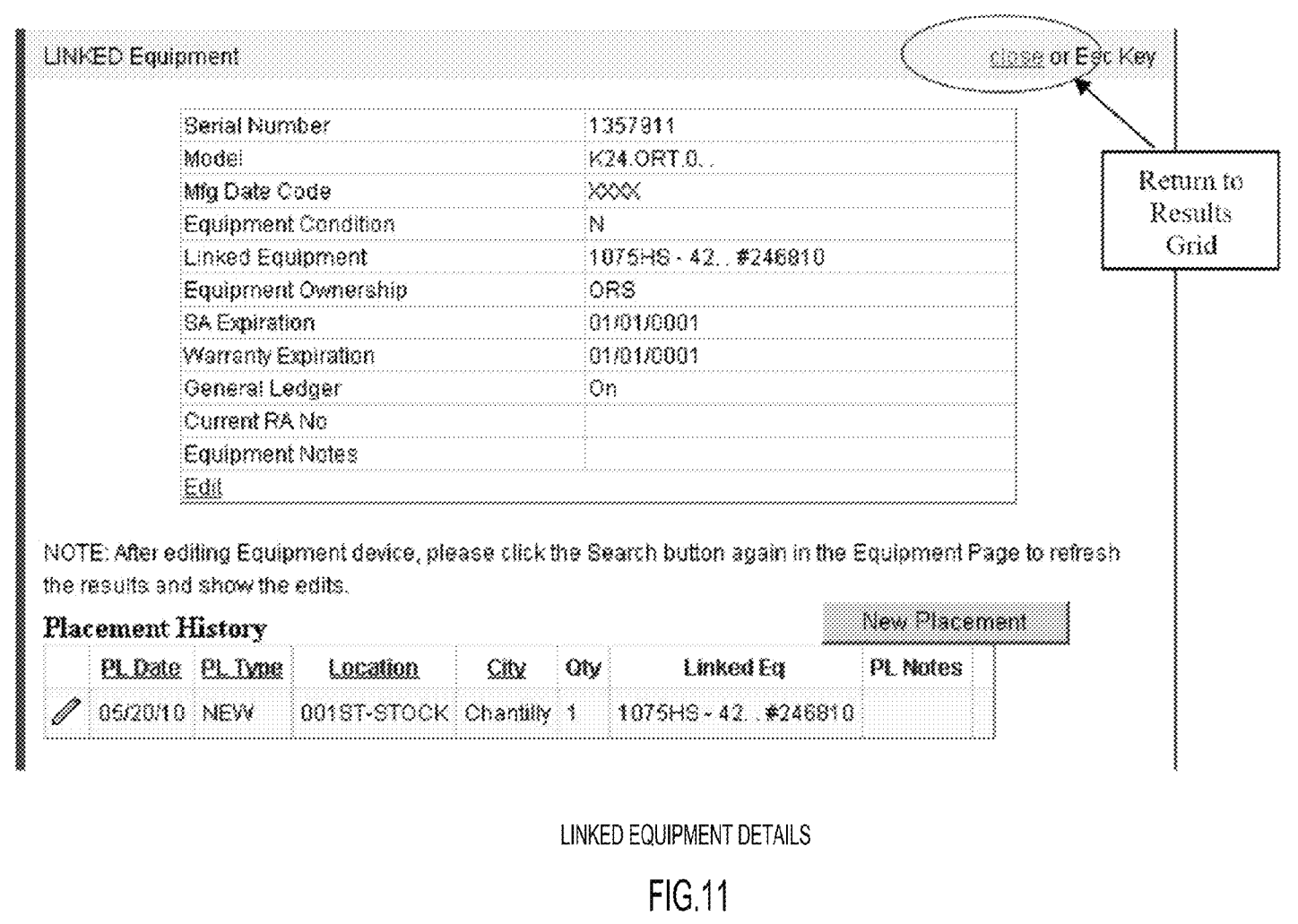

2. The Linked Equipment Detail page will display (See FIG. 11—Linked Equipment Details). This page provides the same details as clicking on the "Details" link from a Result Grid, without having to separately search for the Linked Equipment.

3. Click on the "Close" or Esc Key to return to the Results Grid.

Exporting Results to Excel

The system allows you to export the Results Grid and the Placement History for a specific device to an excel spreadsheet (See FIG. 8—Using the Results Grid above). The following steps provide an example session in how to export Search Results.

1. Complete a search.

2. Click on the Export Results to Excel link.

Figure 12:
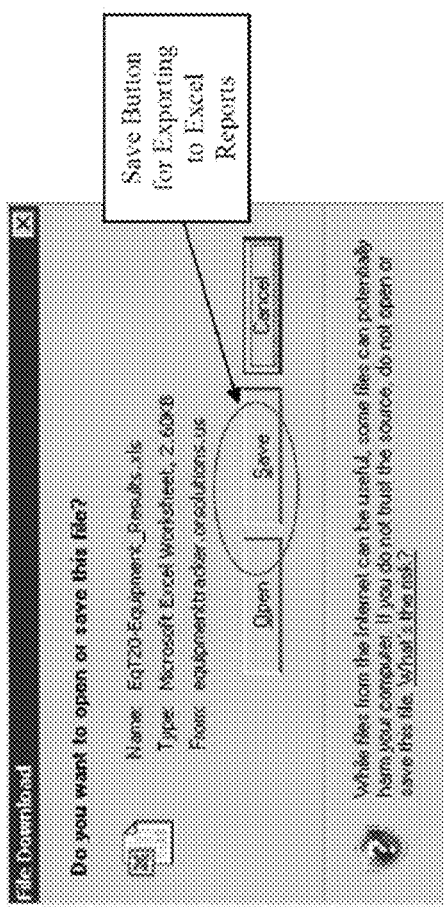
FIG. 12 is a schematic illustration of an example graphical user interface screen of an export dialogue box.

3. A dialogue window will display (See FIG. 12—"Export Result to Excel" Dialogue Box). Click Save. Selecting "Open" in this dialogue box will cause the file type to default to "Html" rather than "xls" format. You can elect to Open the file first, but be sure to change the file type in the "Save As" Dialog Window to EXCEL Workbook.

Figure 13:
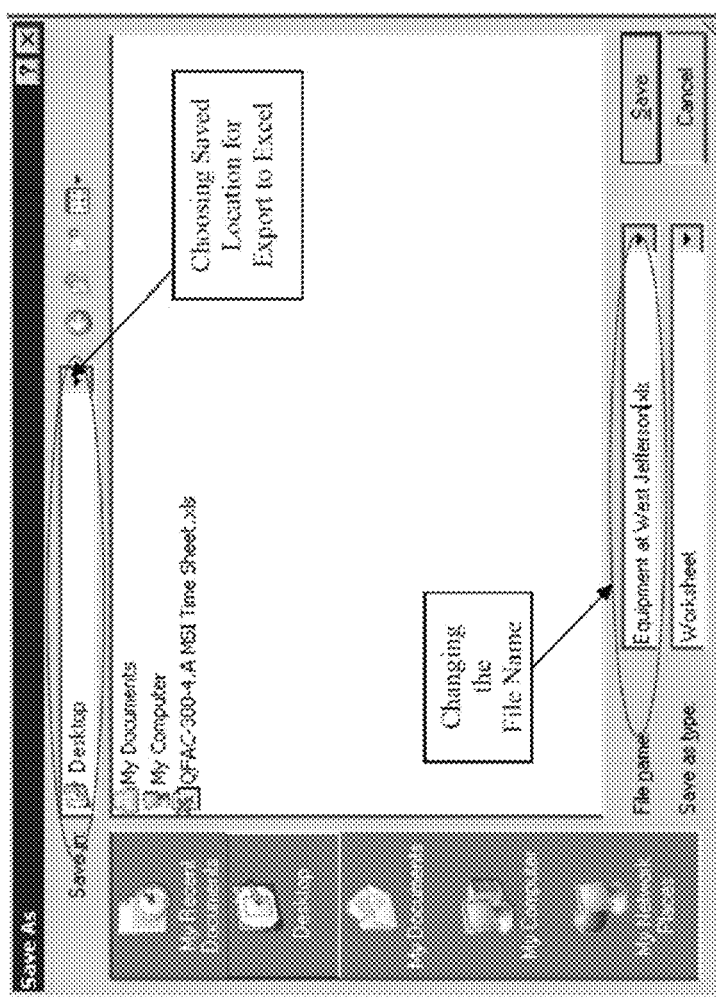
FIG. 13 is a schematic illustration of an example graphical user interface screen for saving export results.

4. Determine the location to save the EXCEL spreadsheet (in this example: Desktop) and provide a name for the file (See FIG. 13—Saving Export Results to Excel Spreadsheet).

5. The spreadsheet contains multiple columns. Not all will be pertinent for your use and can be deleted. All EXCEL functions are available.

You can also generate a Placement History Export. The following is an example session.

1. Identify the Equipment Device and click on the Placement History Link

2. Select "Export Placements to Excel".

3. Follow steps 3 and 4 above. There is no need to provide a file name for exporting Placements. It is automatically providing using the Model and Serial Number of the Equipment Device. Additional reports are available on the Main Menu Bar under "Reports" as described below. Custom reports can be created by the SA upon a User's request through submission of the Report Request Form.

Search Tips

The following provides helpful information on conducting searches.

1. The system takes advantage of INTERNET EXPLORER functionality. In addition to the Search capability, you can use the CTRL+F keys on your computer to search any page (including Results Grids).

2. Non-serial numbered items do not have placement history. Note that Accessory Placements have been consolidated (resulting in QTY values greater than one).

3. The Number of Hits identified will not always equal the number of pieces of equipment. Accessories have Quantity (QTY) values greater than one as these items are not tracked by Serial Number.

4. Searching on the "Model" field or the "PL Types" field provides the additional capability to select multiple search items within the Drop-Down Menus.

To select multiple items in sequence use the Shift key.

To select multiple items out of sequence use the Control key.

5. The Catalogue Field allows you to search for groups of like Models. For example, if you want to find all devices of a particular model in your territory, select the model from the Drop-Down Menu in the Catalogue Field.

You can obtain the same search results by multiple selecting all the device models in the Model field using the instruction in #4 above.

6. Care needs to be taken not to introduce conflicting parameters such as searching for equipment in Loc ID AZ-010 and in the state of Virginia. If you do not get expected results for a search, double check the search parameters.

7. Any field with an * supports wildcard search. Just use the "%" sign either as a leading or ending character. Currently only the "Serial Number" field is available for wildcard searches.

8. You can use the "Location History" available under "Locations" to review Historical Placement information as described below. This assists in answering questions such as: "Did Inova Fairfax Hospital ever evaluate a 1058HS?"

How to Use Resources

"Resources" provides information required to manage and group data. "Resources" is used primarily by the EqT Admin, but can assist general users in understanding data elements of interest in searches. "Resources" is accessible from the Menu Bar and provides access to:

Locations. (Available to Sales Execs)
Placement Types. (Available to Sales Execs)
Models. (these are listed in the Drop-Down Menu for the Model Field in the Search Window)
Catalogues. (these are listed in the Drop-Down Menu for the Catalogue Field in the Search Window)
Territories.
Regions.

The following is an example session to access Resources:

1. Click on Resources on the Menu Bar.

Figure 14:
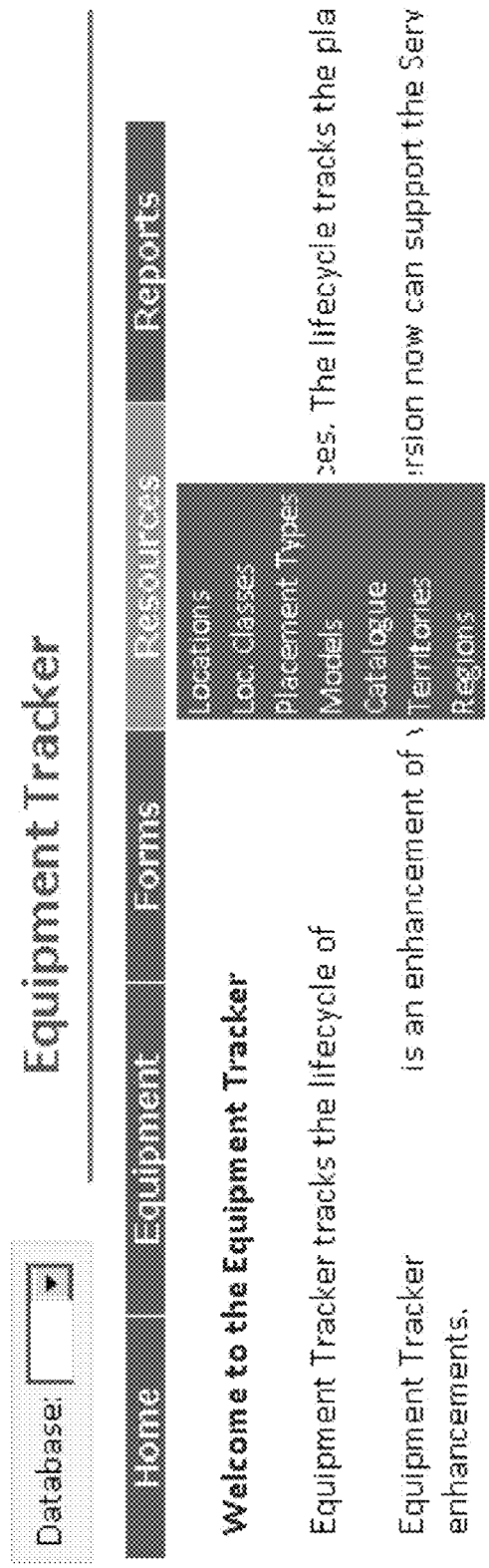
FIG. 14 is a schematic illustration of an example graphical user interface screen for accessing resources.

2. Slide cursor to the pop-up menu and select the Resource of interest (See FIG. 14).

Locations

"Locations" refers to Hospitals, Rep Inventories and other Company locations. The Location Name, City and State are populated from a database, and updated via automating synchronization weekly based on the Account Number. The Loc ID is the same identifier used for the Account Number.

The Location Search Window allows you to search on fields related to location information including Loc ID, Name and Location Class (Hospital_Customer, Rep Inventory, Company or Disposed). For Sales Executives, the Territory search is automatically completed. When selecting Locations from Resources on the Main Menu bar, all Locations for the Territory will be displayed. This same policy applies for Regional Sales Managers and Region information.

Figure 15:
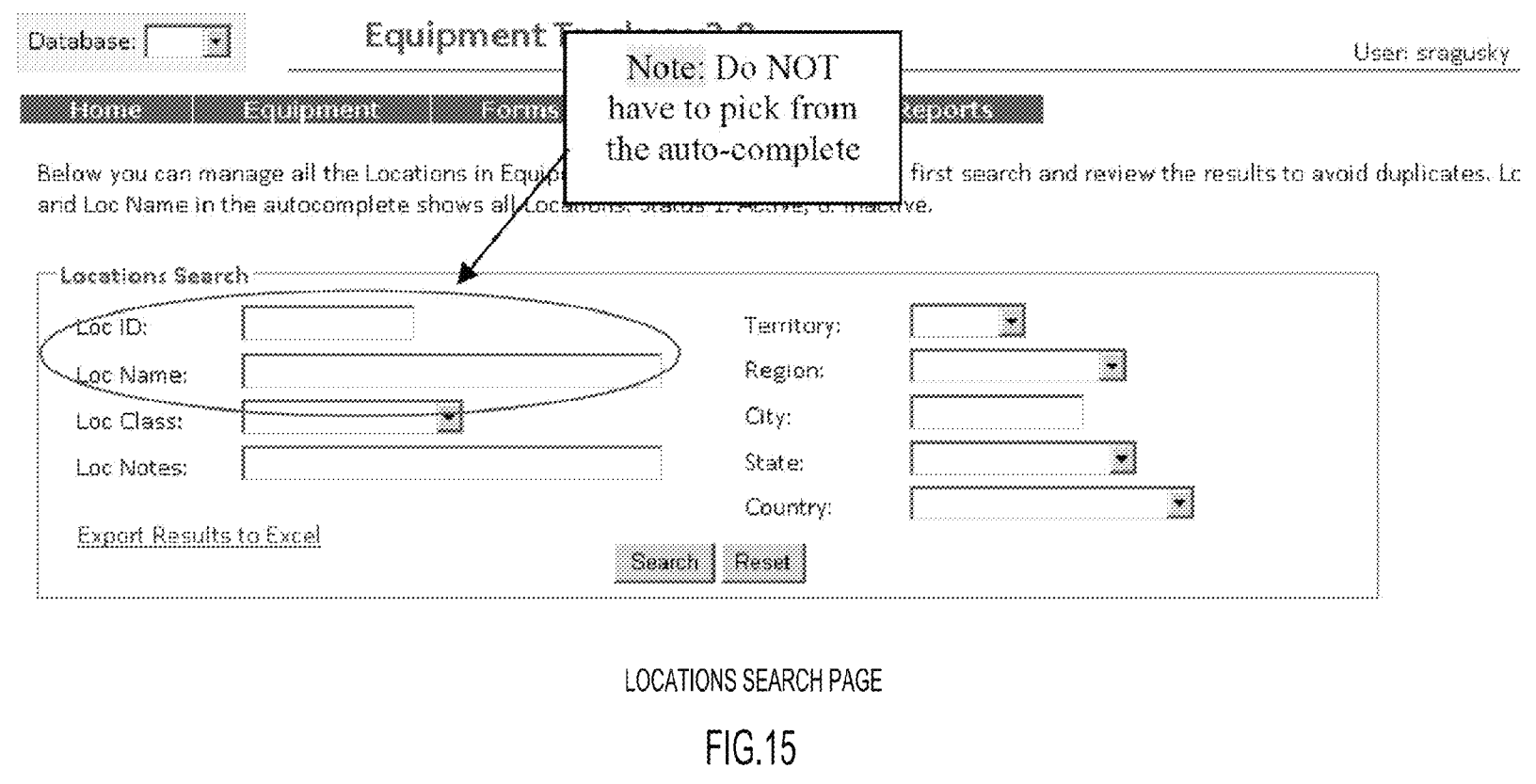

The Search capability functions are similar to the Equipment Search. The main difference is that Loc ID and Loc Name do not have to be selected from the auto-complete list and can be entered incomplete (See FIG. 15—Locations Search Page). Locations also have a "Status" field, which identifies if the Location is active (=1) or inactive (=0). Equipment can not be placed at Inactive locations.

Using the Location Results Grid

Completing a search on the Locations Search Page will display a Results Grid (See FIG. 16—Results Grid for Location Search). Functionality for this Results Grid is the same as for an Equipment Search. Underlined Column Headers can be clicked on to change the sort order. Selecting the Details and/or History Link provides additional information on an individual Location.

Equipment Agreements (EAs) are also stored in the system. The status of the location and the EA is indicated by the color coding of the Location ID in the Results Grid. For example:

GREEN=EA exists and equipment quantities on the EA match the Placements in ET.
ORANGE=EA exists, but quantities do not match.
RED=EA does not exist.

Location Details

Figure 17:
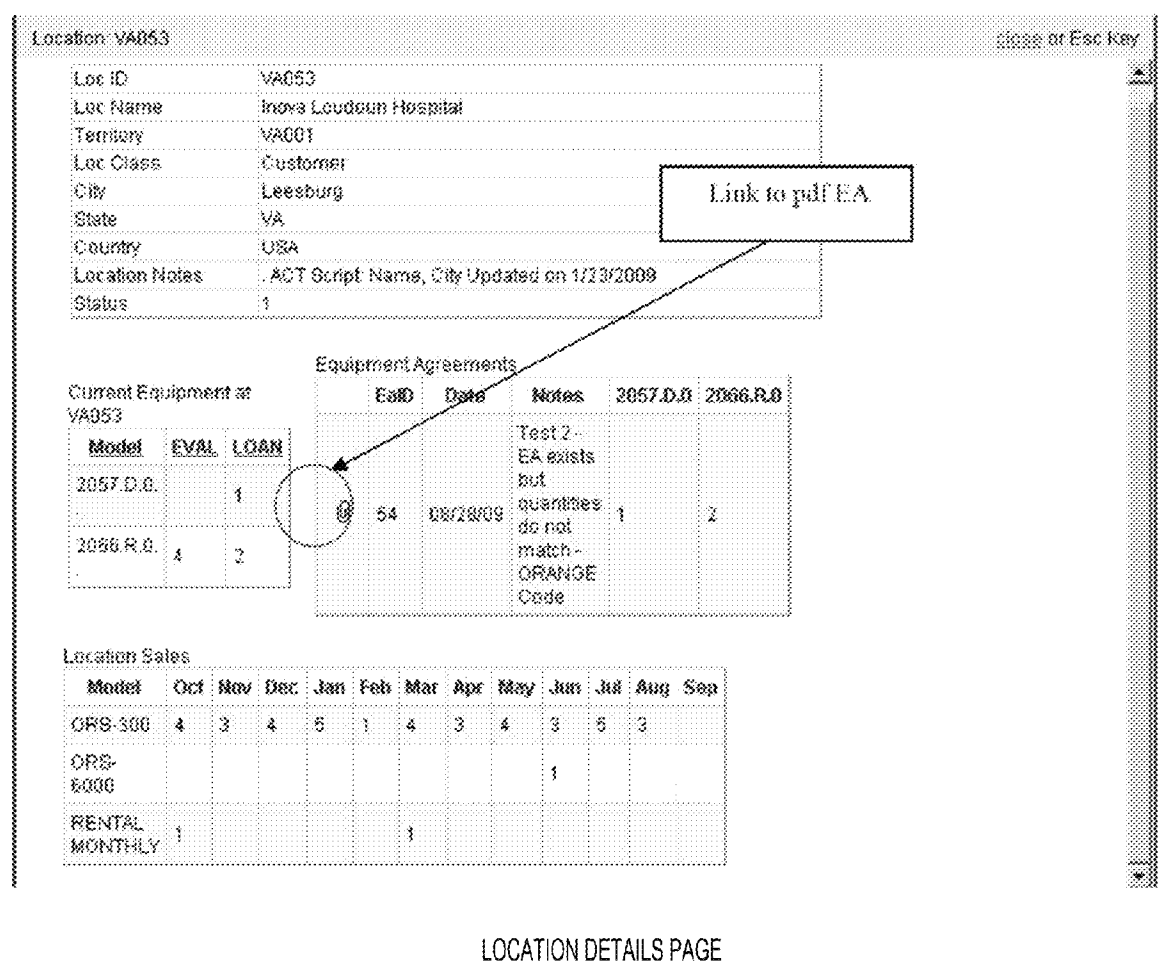

Clicking on the Details Link in the Location Results Grid provides a matrix of current equipment and Placement Type Status (See FIG. 17—Location Details Page). Sales for the period are identified. Also provided is information on EAs associated with the Location. This functionality is not available to Sales Executives. Sales Executives are to coordinate EA activities with Sales Support and their management. The following is an example session.

1. Click on the EA "paperclip"

2. A dialogue box asking if you want to save or open the attachment will appear.

3. Select open to see a pdf document of the EA.

4. The equipment documented on the EA is also displayed.

5. Selecting the "Close" or pressing the Esc key will return you to the Results Grid.

Location History

Selecting the "History" Link on the Results Grid provides a snapshot of all equipment ever placed at the Location (See FIG. 18—Location History Page). The Window provides the same capabilities as the Results Grid, by allowing you to sort on underlined Column Headers. The "Close" or Esc Key will take you back to the Locations Search Results Grid.

Placement Types

Placement Types contains the list of all available Placements for Equipment including:

Loan, Eval, Sold, Rep Inventory, Stock, etc.

Figure 19:
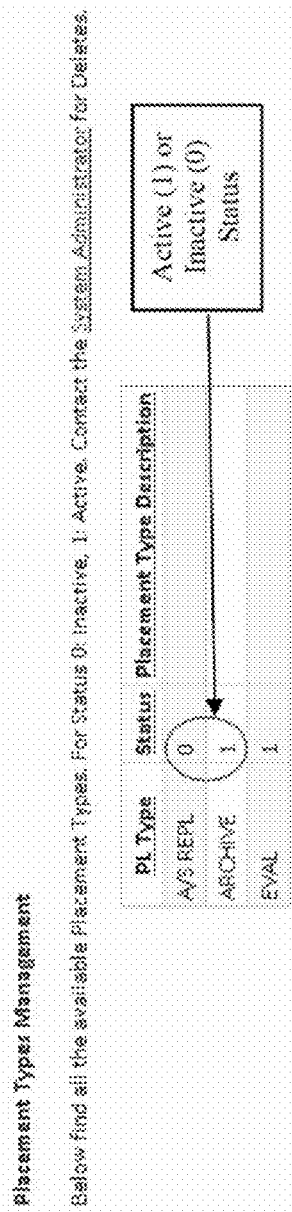
FIG. 19 is a schematic illustration of an example graphical user interface screen of a placement types resources page.

Descriptions on use for each Placement Type can be found below. FIG. 19—Placement Types Resources Page displays the "Placement Types" page. Placement Types also has a Status Field, which indicates Active ([=1] option is available for new placements) or Inactive ([0] placement type is no longer used). Inactive Placement Types are available in the Equipment Search window because of historical placements that used the type.

Models

The Models Resources page provides information on each of the products produced. FIG. 20—Models Resources Page displays the information detailed on the Models Resources page.

Column headers can be used to sort the list of models and Models also has a Status field. The Status field indicates Active models with a "1", which identifies those products currently under manufacture. A Status of "0" indicates models that are no longer being manufactured, but remain in use. A Status of "2" is assigned to non-serial numbered items such as Stands, which are not currently tracked.

Catalogues

The Catalogues Resources page (See FIG. 21—Catalogue Resources Page) provides information on logical groupings of Equipment. For example: IV Warming Systems, which includes all warming units and all models of those warming units. Catalogues has a Status Field (1=Active, 0=Inactive), and can also be sorted by clicking on the column headers. Catalogue Description will be populated in the operational database as described below.

Territories

The Territories Resources page (See FIG. 22—Territories Resources Page) provides information on Sales Territories. This information can be used to facilitate searches for Equipment or Locations located within a particular Sales Territory. The primary city within the Territory is the Territory Identifier. Regions are defined geographically. Territory Descriptions are populated with the zip code ranges defining each territory.

Regions

The Regions Resources Page (See FIG. 23—Regions Resources Page) provides further information for how equipment is physically managed and identifies the Regional Sales Manager and Sales Support staff assigned to the Region. Region descriptions will be populated in the operational database and identify the States assigned to the Region.

Reports

A Crystal Report Engine allows Users and Sales Executives to run selected pre-formatted reports. "Reports" is available from the Main Menu Bar. The following is an example session.

Figure 24:
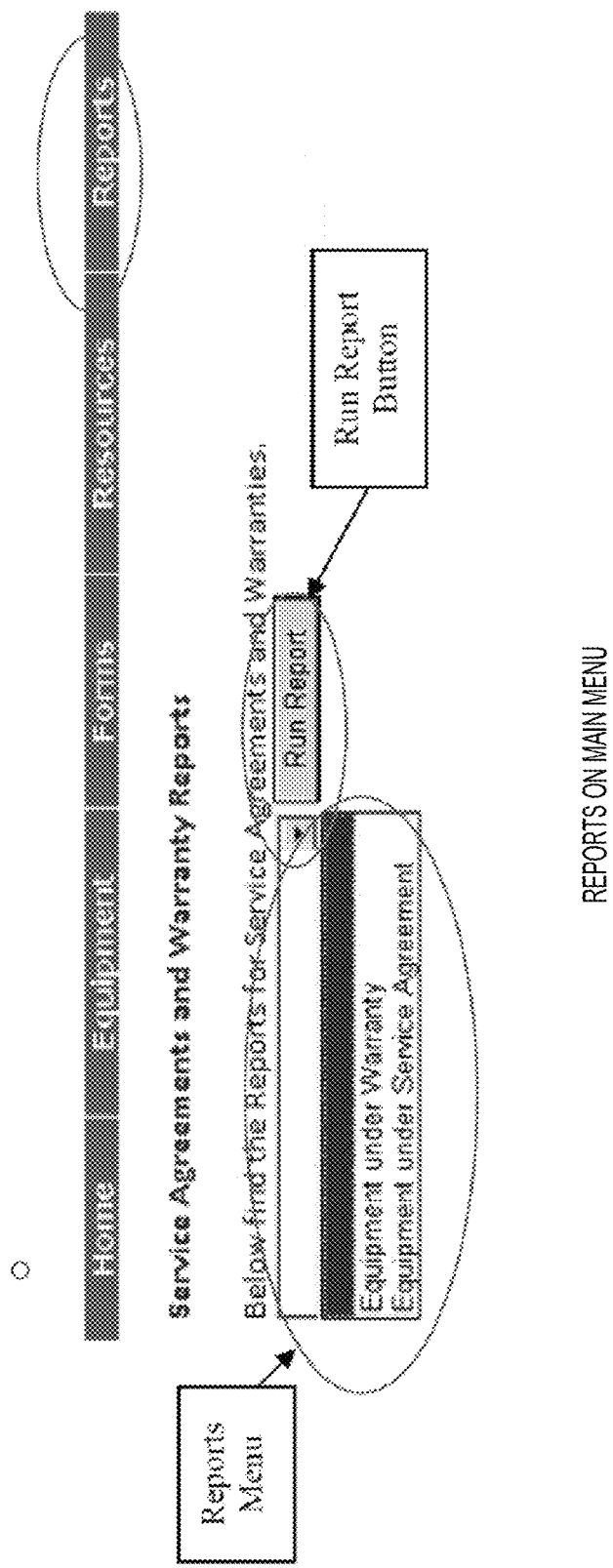
FIG. 24 is a schematic illustration of an example graphical user interface screen of reports.

1. The reports available to you are defined by Role and access to databases. (See FIG. 24—Reports on Main Menu). Sales Executives have access to reports under Misc and Service Agreements.

2. Select the category of Report.

3. The page will update with a drop-down list of report formats.

4. Highlight the report you wish to run and click on the "Run Report" button.

Figure 25:
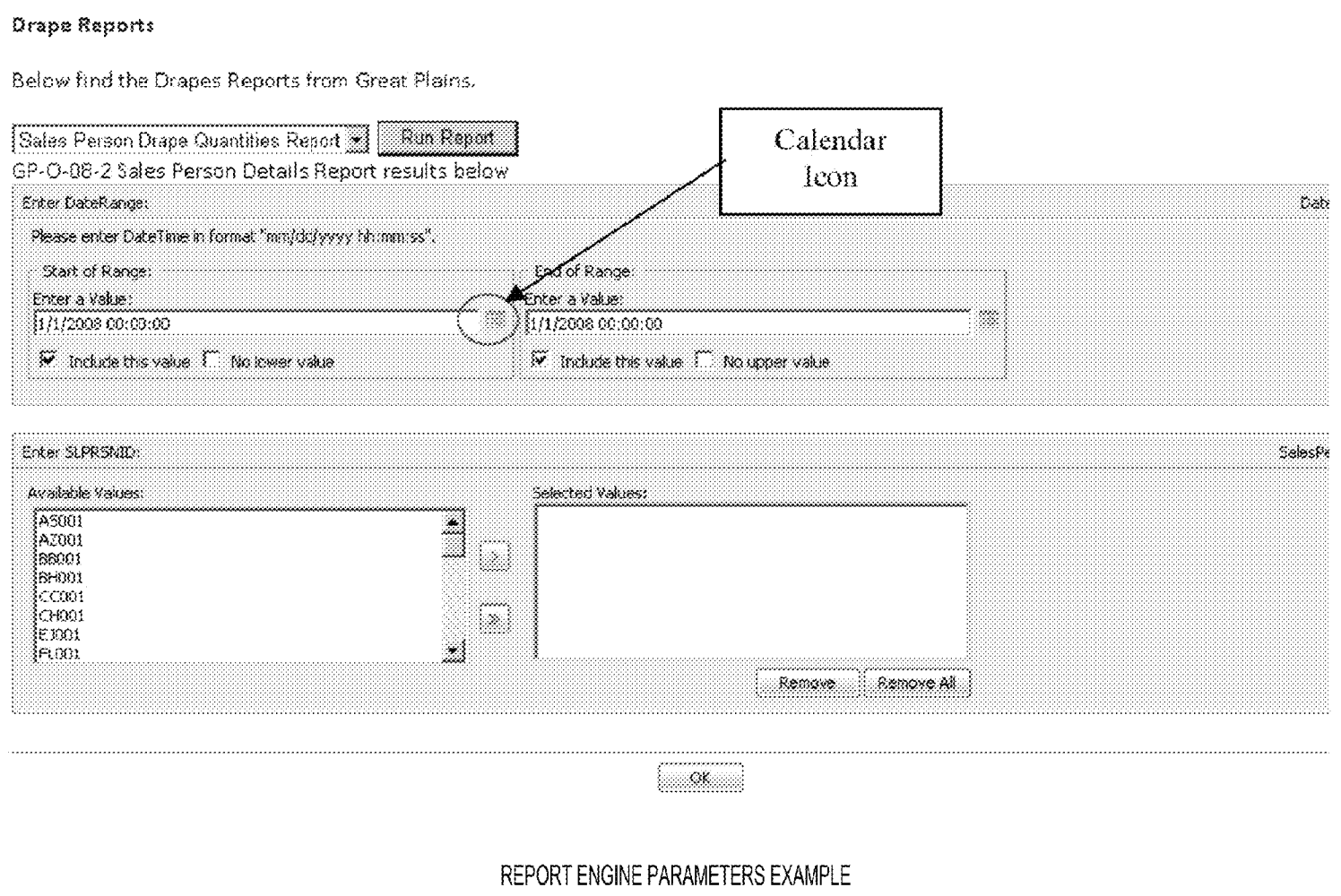

5. The report will display the embedded Report Engine menu bar and information related to the report generation parameters including date ranges (See FIG. 25—Report Engine Parameters Example). All reports function in the same manner, with the Report Engine providing the parameters to build your report.

6. Enter the parameters/search criteria (in this case Date-Times—you can use the calendar icons to simplify data entry). Move appropriate Available Values by highlighting the desired value and clicking on the >.

Figure 26:
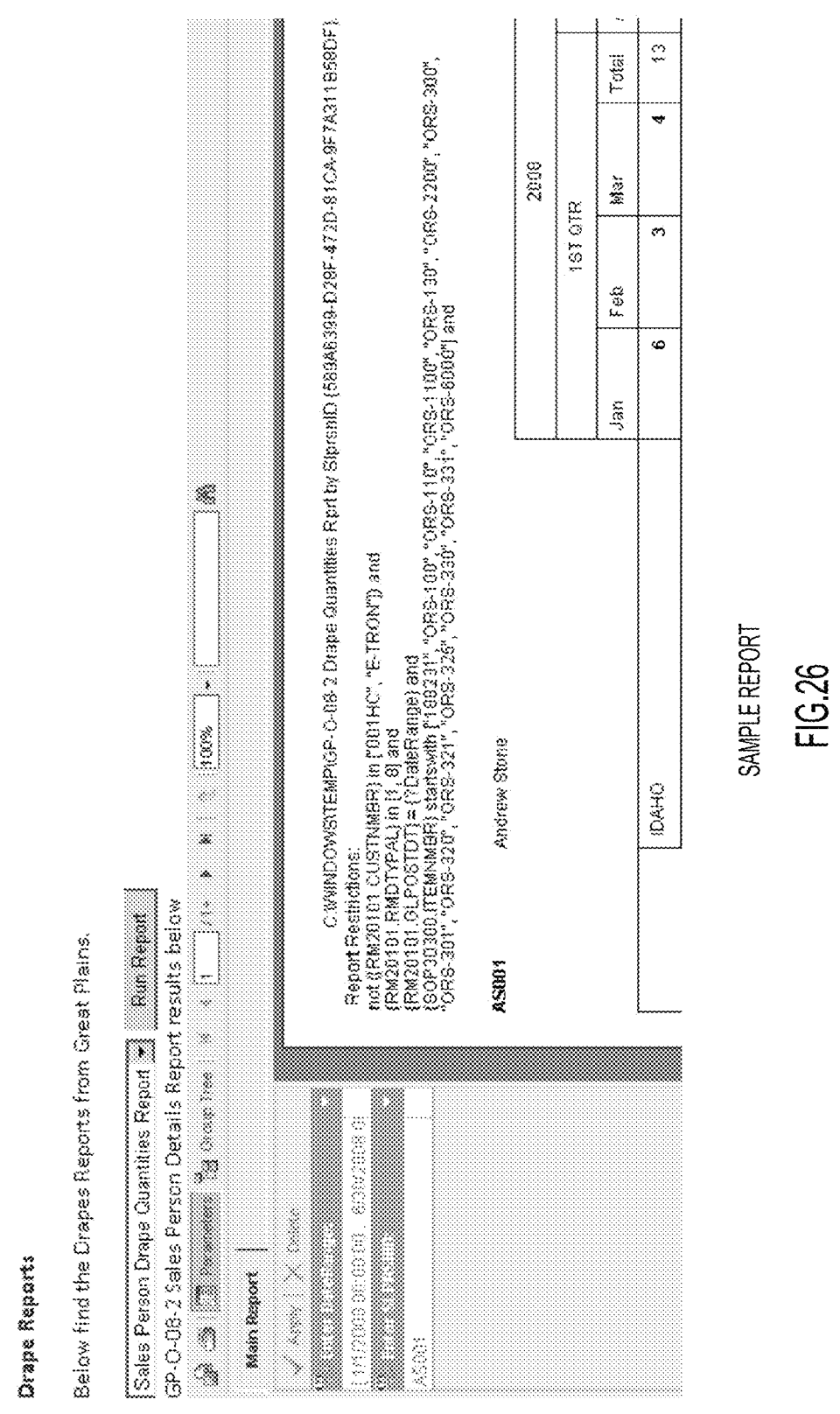

7. Click the "Ok" at the bottom of the Parameters window and the report will generate (See FIG. 26—Sample Report. Only a small portion of this report is shown in the example).

8. The Report engine provides several additional features including the ability to print, export, and jump to the group based on Group Tree. Reports can be modified to prompt for variables and allow filtering.

9. To print the report, click on the printer icon.

10. To export the report, click on the save icon/paper icon. A dialogue box will display, which allows you to select the file format for the export and a page range, if desired.

11. Change the file format from the default Crystal Reports (RPT) to EXCEL or WORD and click the Export button on the Export Dialogue box.

12. The exported report will download, and a window will appear with the option to open or save the exported report. When saving the report you will be prompted for a location and provided the option to name the report. Additional reports can be added.

II. Users With "Writer", "EqT Admin", or Similar Roles

The following description relates to the manner in which users with "Writer", "EqT Admin", or similar roles navigate through the system (e.g., via the Tracking and other modules) and perform functions assigned to those roles.

Creating and Placing Equipment Devices

Creating Equipment Devices relies on the EqT Admin having completed the requisite preliminary data entry (Ex: creating "Model" information). Both Writer and EqT Admin can create Equipment Devices. There are two types of Equipment Devices:

Serial Numbered

Accessories

Input for New Equipment is derived from the Finished Goods Delivery Notice (FGDN) provided via e-mail to the EqT Admin by Manufacturing and confirmed by Receiving. Any discrepancies between the FGDN and Receiving are resolved prior to any entry into the system.

Input for moving Equipment Devices from one Location to another or changing Placement Types comes from the following:

Bill of Lading (Sales Execs placing Equipment Devices into a new Location);

Pick-up Sheets (Sales Execs picking up Equipment Devices from a Location);

Rep-to-Rep Transfer Forms

Shipping Packing List (direct shipment from Stock to a new Location);

Accounting (invoicing indicating current Placement Types have changed)—this can be in combination with a Shipping Packing List.

Creating Serial Numbered Equipment Devices

The following is an example session for creating serial numbered equipment devices.

1. Select "New Equipment" under "Equipment" on the Main Menu Bar.

Figure 27:
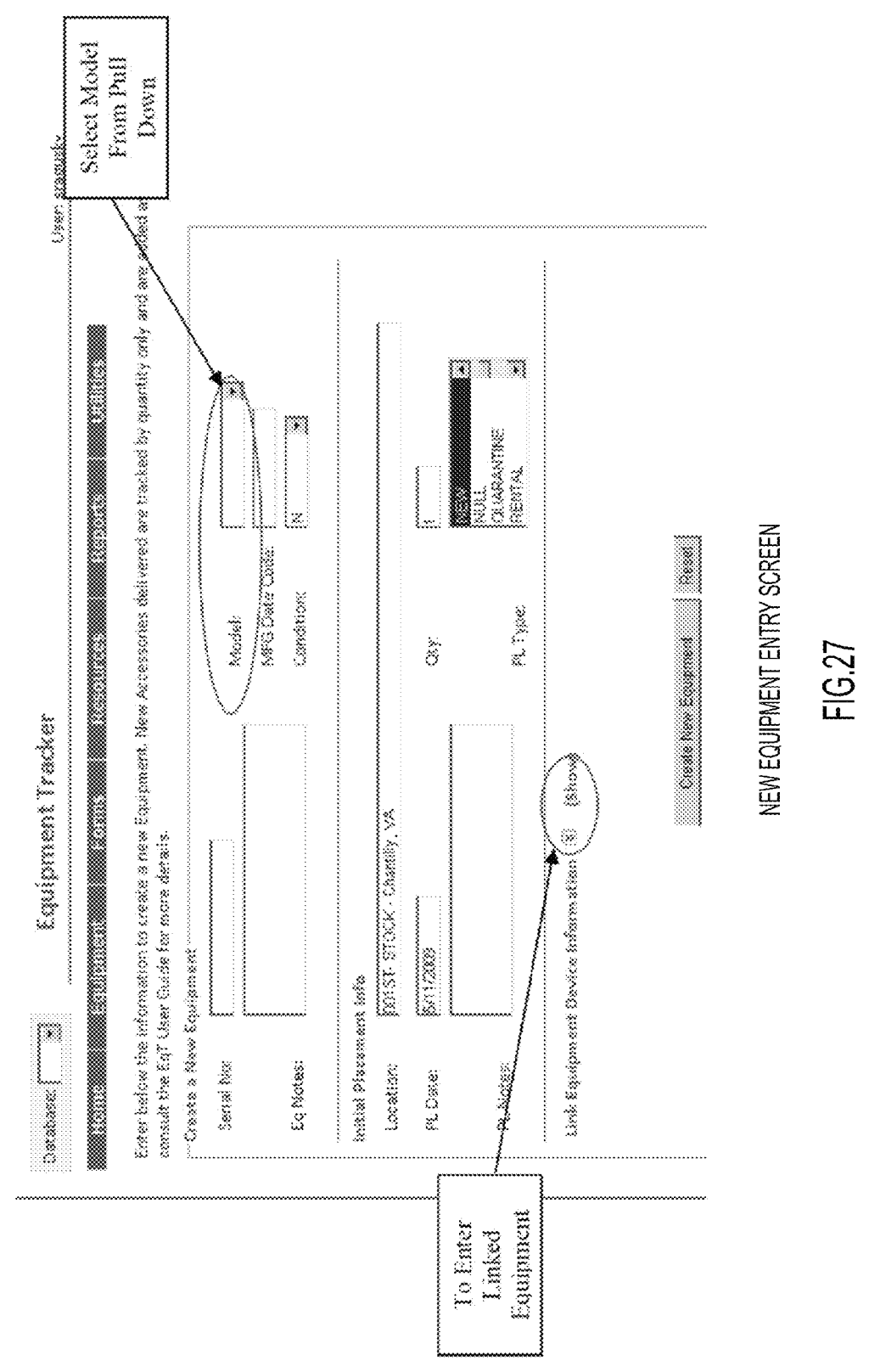

2. Enter required information (See FIG. 27—New Equipment Entry Screen).

3. Enter Serial Number (cut/paste from EXCEL spreadsheet or hand enter).

4. Select the correct Model from the pull down list (confirm Configuration and Product Level are correct).

5. Enter MFG Date Code.

6. Condition, Location, Quantity and Placement Type default to correct settings for NEW EQUIPMENT.

Condition=New

Items that are "Modified" as described below need to have the default changed from "N", for New, to the appropriate Condition Code.

Location=Stock
Quantity=1
Ownership=Company
Placement Type=New
On GL/OffGL=On

For items that are "Modified" the Placement Type needs to be change the default from "New" to "Stock". A second placement record also needs to be created for Modified equipment showing a "New" Placement Type and the initial Placement Date of the original equipment. A "Note" should be added indicating the equipment was modified from a pre-existing model.

7. Ensure Placement Date is correct.

Defaults to the date the entry is created.

8. Click on "Create New Equipment" button.

9. Enter next Serial Number, if Model information is the same and continue with next New Equipment Device.

10. Select Reset for a different Model Equipment Device.

Creating Linked Equipment Devices

Only Serial Numbered Equipment Devices can be linked. The following is an example session.

1. If Equipment has Linked Equipment associated, click on the "Show" link (See FIG. 27—New Equipment Entry Screen).

2. Enter information for current device.

Figure 28:
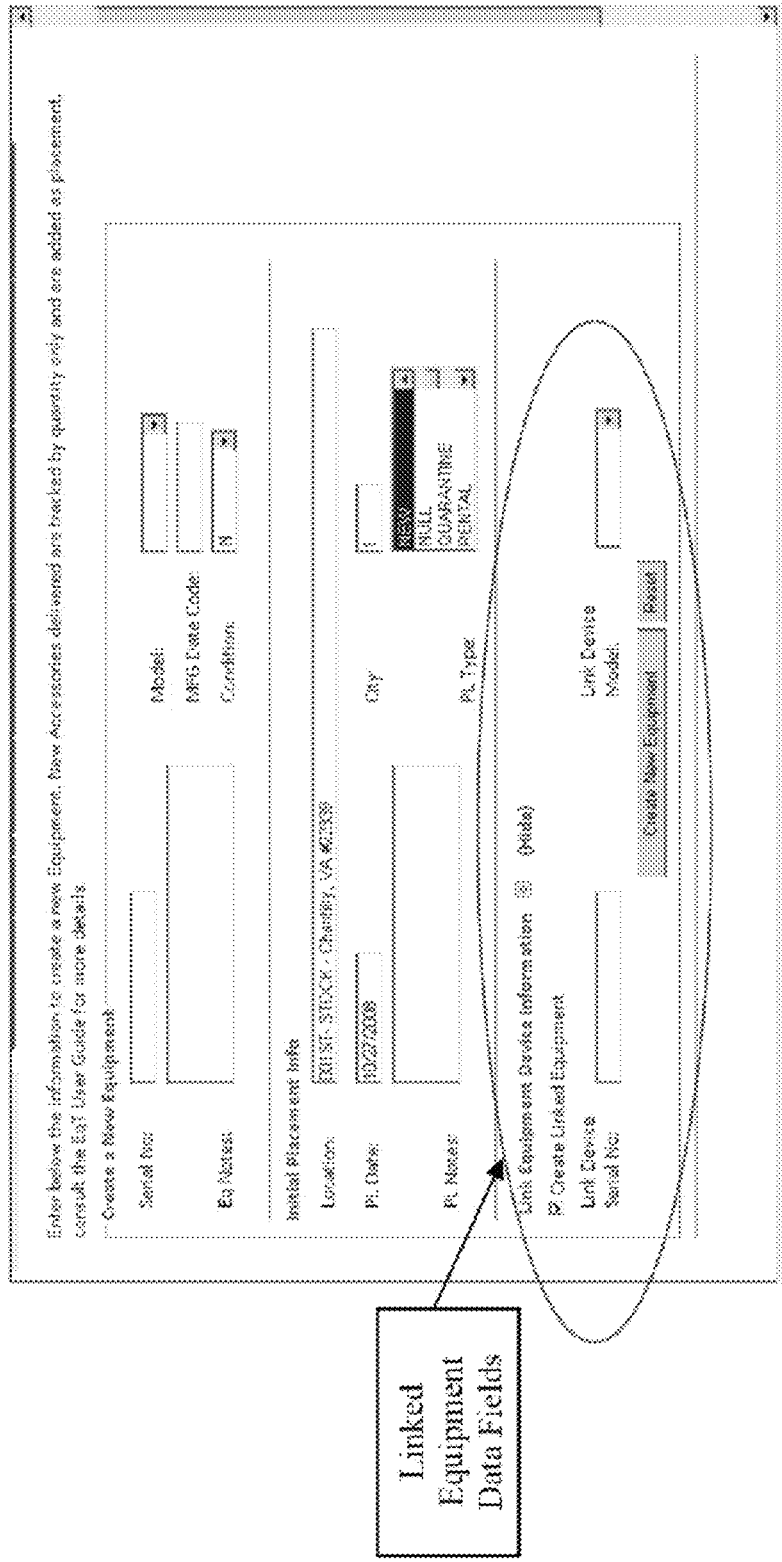
FIG. 28 is a schematic illustration of an example graphical user interface screen for creating linked equipment.

3. Enter information for linked device in the Linked Equipment Area.

a. If the linked device needs to be created check the "Create Linked Equipment" check box. (See FIG. 28—Creating Linked Equipment).

Figure 29:
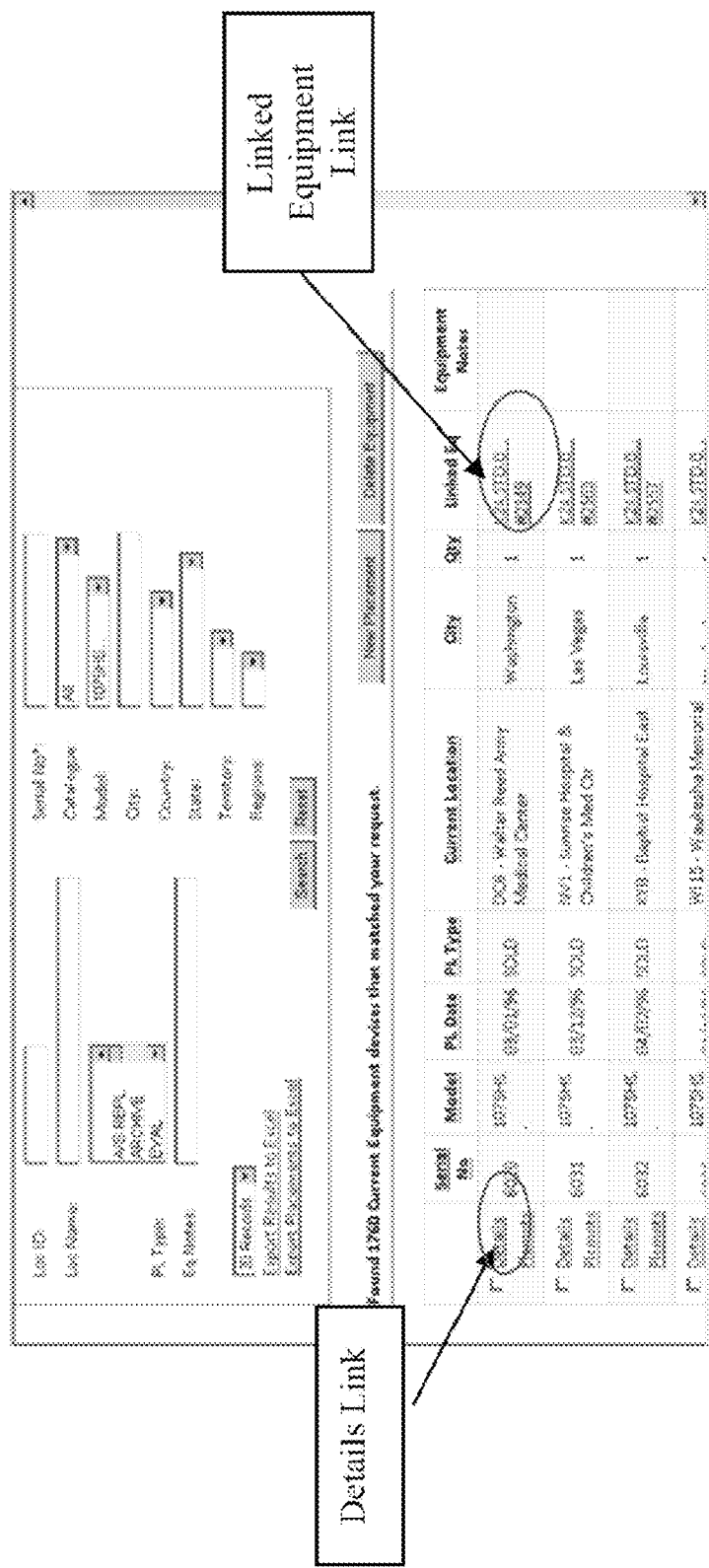
FIG. 29 is a schematic illustration of an example graphical user interface screen for linked equipment.

4. Click Create New Equipment and devices will be linked as shown in FIG. 29—Linked Equipment.

5. Selecting the Details Link will display information on the Equipment Device, including the Linked Equipment. Selecting the link in the Linked Eq column also displays details on the Linked Equipment Devices from the reverse perspective (See FIG. 30—Selecting Details to Review Linked Equipment Information and FIG. 31—Linked Equipment Link). Linked equipment defaults to the same Placement Type and Location as the "parent" Equipment Device.

Editing Linked Equipment

There are cases where the "Parent" Equipment Device will have a different Placement Type than the Linked (Child) Equipment. An example of this is one device that is "Sold", but another device is a Loaned Item. The following is an example session to change the Placement Type of a Linked Equipment Device:

1. Click on the Linked Equipment Device Link.

2. Click on the Pencil to Edit the Linked Equipment Device (See FIG. 31—Linked Equipment Link).

3. Change the Placement Type as appropriate.

Unlinking Equipment

To unlink a "child" Equipment Device, a search for the item is initially performed as described above. The following is an example session for unlinking equipment.

1. Click on the Details Link.

Figure 32:
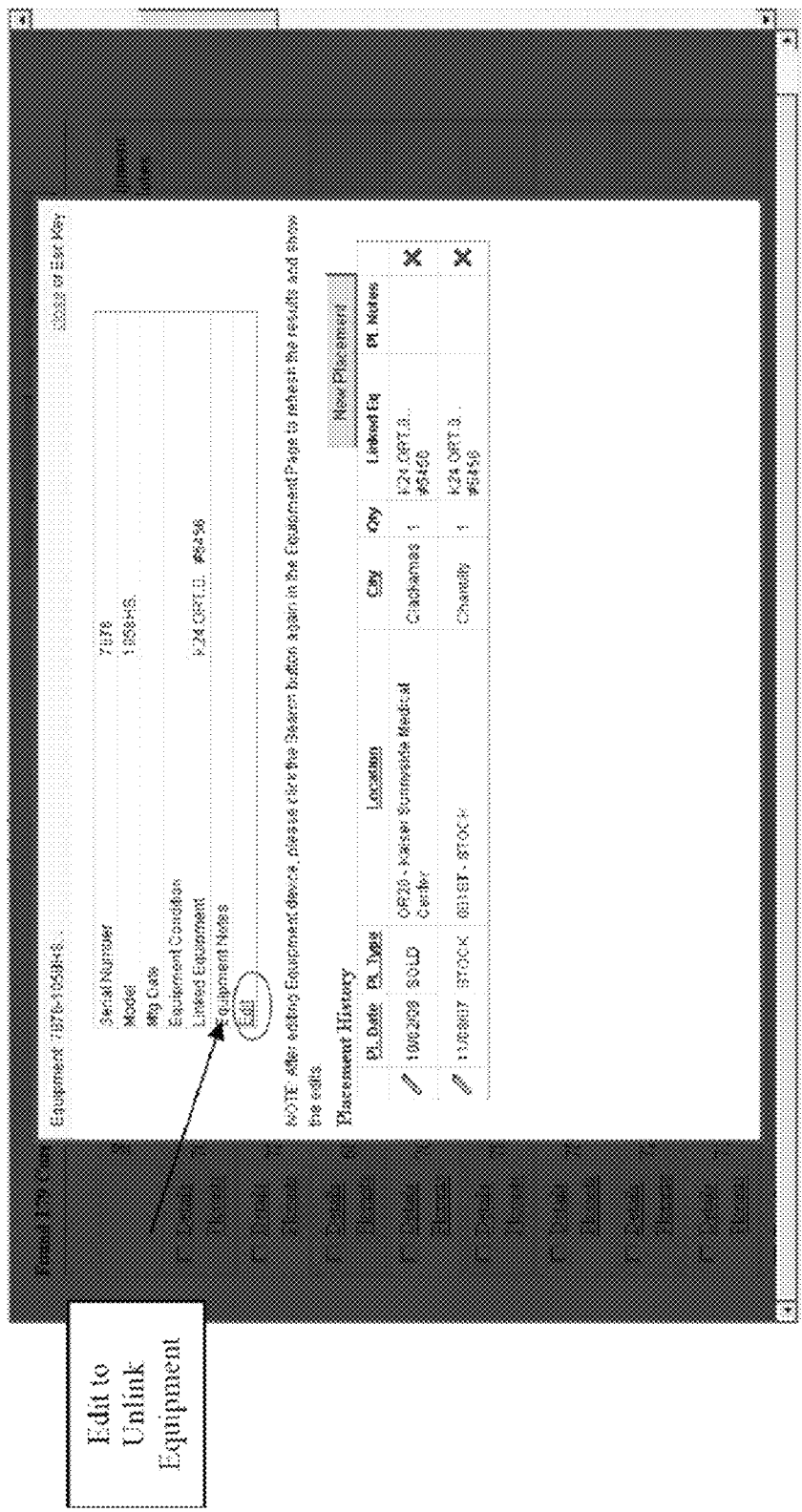
FIG. 32 is a schematic illustration of an example graphical user interface screen for unlinking equipment.

2. Click on Edit within the Details Record (See FIG. 32—Unlinking Equipment).

3. Erase the Linked Equipment serial number.

Figure 33:
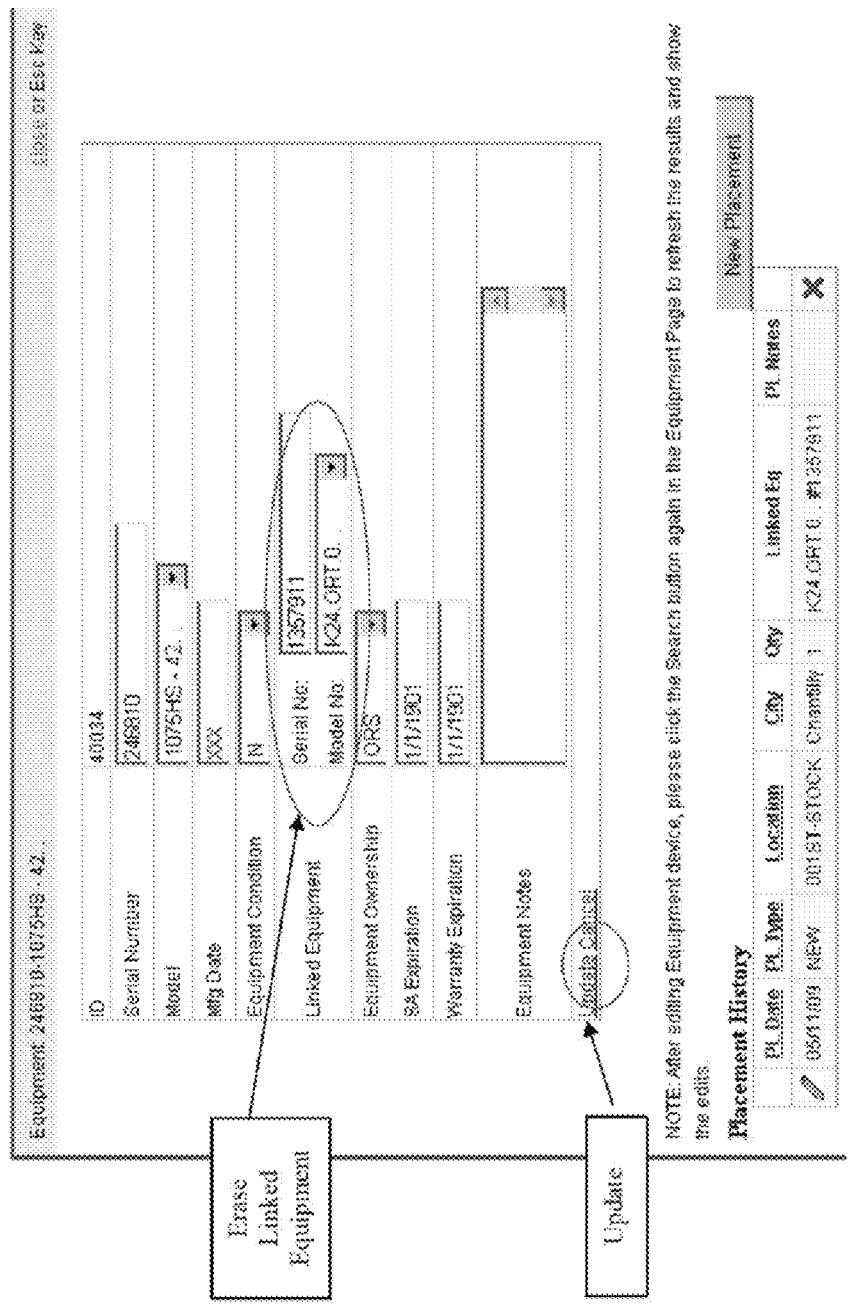
FIG. 33 is a schematic illustration of another example graphical user interface screen for unlinking equipment.

4. Select "Update" (See FIG. 33—Unlinking Equipment Continued).

5. To verify, search for Equipment Device and confirm link no longer exists. This situation leaves a device in place with no associated device. The EqT Admin is responsible for collaborating on the replacement device provided to the customer. Upon identification of the new Equipment Device information, a new Linked Equipment should be created and linked.

Placing Serial Numbered Equipment Devices

The following is an example session to place Equipment Devices in new Locations or change Placement Type:

1. Search for the Location where the Equipment Device is currently located.

Figure 34:
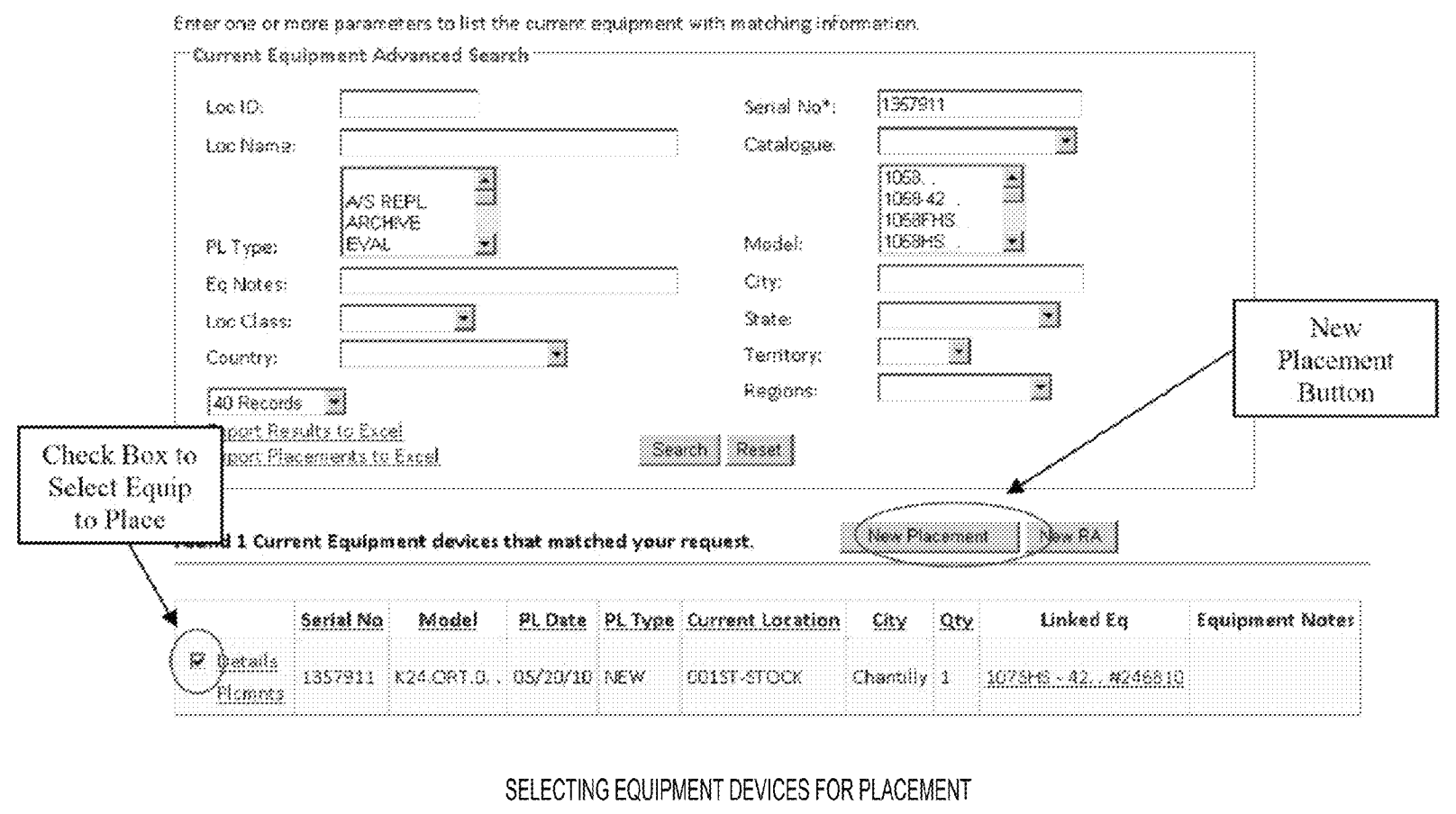

2. Click the check box for the Equipment Device to be moved (See FIG. 34—Selecting Equipment Devices for Placement). You can check one or more devices if they share the same Location/Placement Type.

3. Click on the New Placement Button.

Figure 35:
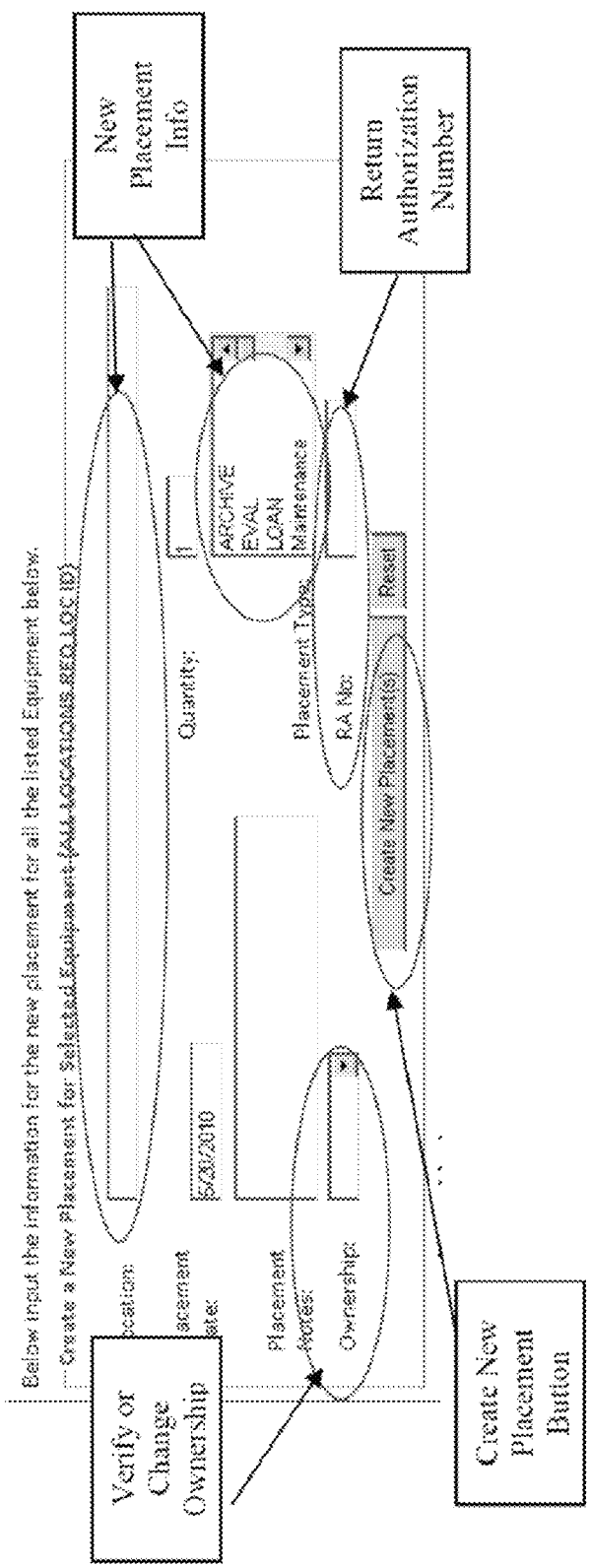
FIG. 35 is a schematic illustration of an example graphical user interface screen for entering new placement information.

4. The Placement screen will display (See FIG. 35—Entering New Placement Information). Complete placement information including selecting new Location, new Placement Type and confirming Placement Date (default is the date data entry is completed).

5. Update Ownership field per rules. Rules for appropriate Placement Types based on Ownership and Location are in place. If there is an error message when applying a new Placement Type, verify that the Ownership and Location Class are correct.

6. If Equipment is associated with an RA, enter the RA (auto-populate field) in the RA Number Field. Equipment placements associated with an RA, either as REPLACEMENT EQUIPMENT or as the Equipment returned using an RA, must be completed using this method. Alternative Placement Methods described below (from the Placement History Link or from Equipment Details) can not be used with Equipment associated with an RA. Accessories/Stands are also returned using RAs. The RA form should be passed by EqT Admin or Writer to the QA Department for the QA Director/QA Writer to note the return of Accessories and Stands in the RA.

7. Click on the "Create New Placement" Button. The Equipment Device and any Linked Equipment will be moved to the new Location. Whenever Linked Equipment has a new Placement, the linked device will have an identical placement created. Where this is not appropriate, the Writer or EqT Admin must manually change the Placement Type on Linked Equipment.

Figure 36:
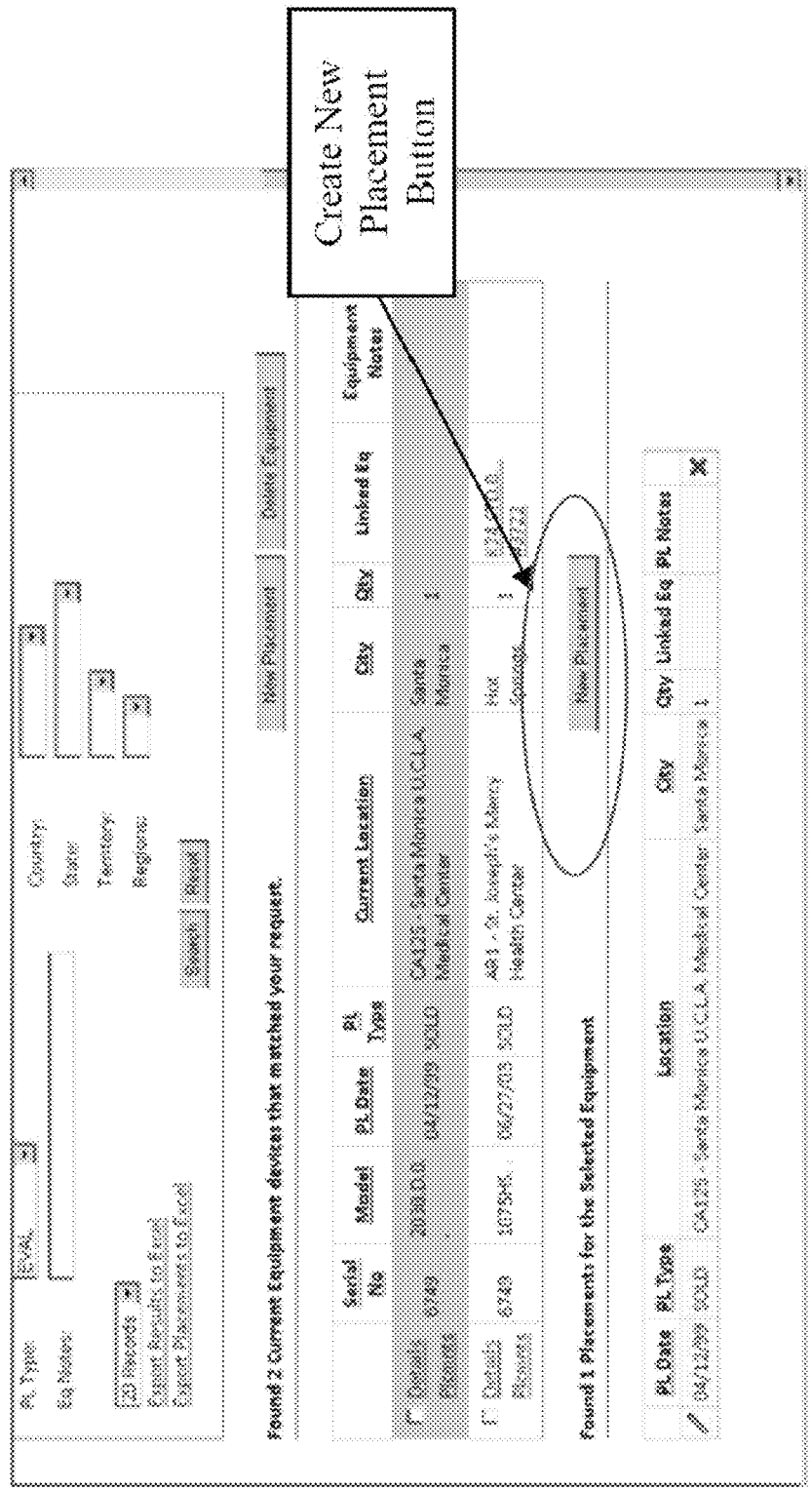
FIG. 36 is a schematic illustration of an example graphical user interface screen for alternative placement functionality.

8. Check the new Location to verify the new Placement. Placements can also be created by clicking on the "Plcmnts" link, which reveal the history of placements for that Equipment Device and click on the "New Placements" button. (See FIG. 36—Alternate Placements Functionality).

Editing Existing Placement Records

Existing Placement Records can be edited to correct inaccurate information. When an edit to a Placement Record is required, the system will capture the UserID and Update Date automatically. The system will also force the EqT Admin/Writer to enter a Placement Note explaining the reason for the edit. This functionality does not apply to non-serialized equipment.

Placement Records can also be deleted, when appropriate (e.g. duplicate entry, erroneous placement). The system requires a minimum of one placement record per piece of equipment. An error message will be displayed if EqT Admin attempts to delete the Placement Record if it is the only one existing for the Equipment.

Rules for Ownership, Placement Type, and Location

Rules exist for Ownership, Placement Type and Location Relationships. Appropriate Ownership values for a given Placement Type and appropriate Placement Types to be used at specific Location Classes may be specified.

Deleting Equipment Devices

"Deleting Equipment" does not actually delete the record from the database. This function is used to "deactivate" or change the status of an incorrect entry of an Equipment Device in the database. Both Writer and EqT Admin have this capability. The following is an example session to deactivate (change status from "1" to "0") a specific Equipment Device.

Figure 37:
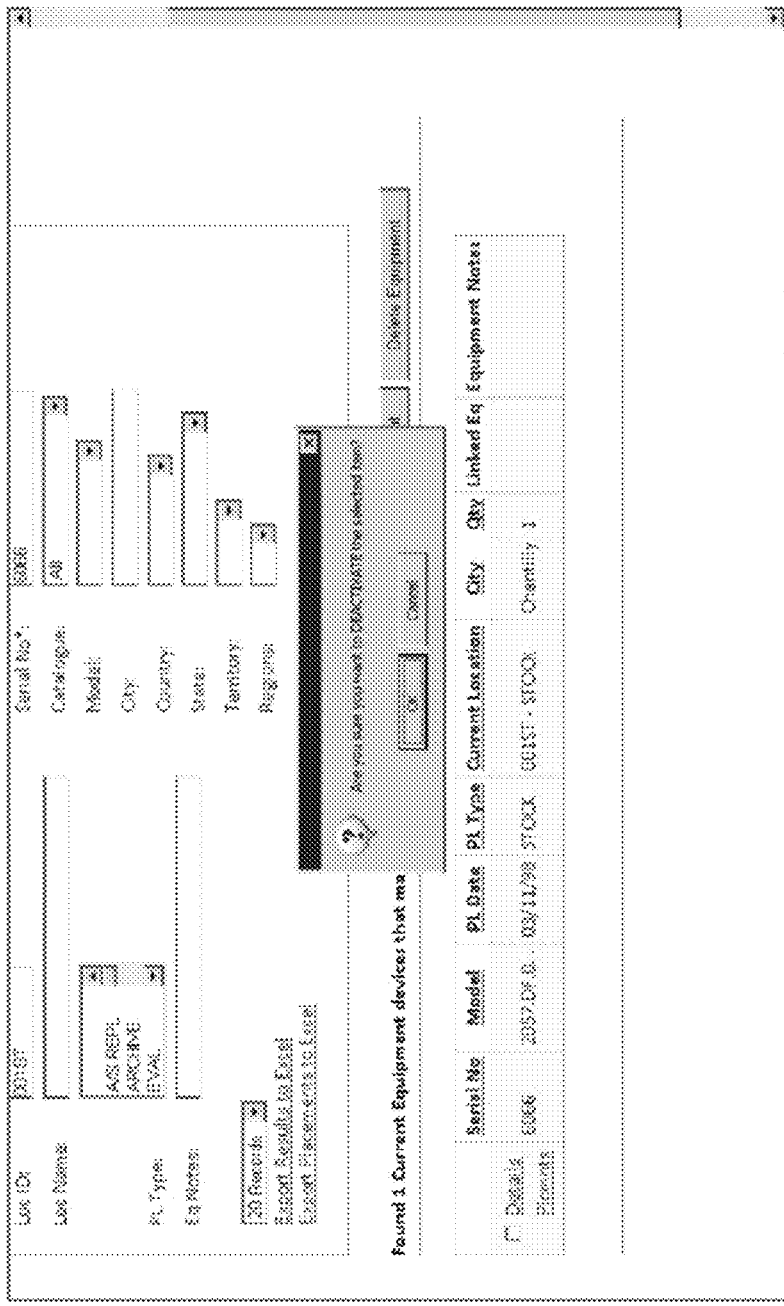
FIG. 37 is a schematic illustration of an example graphical user interface screen for deleting equipment.

1. Search for the Equipment Device using Equipment Search from the Menu Bar.
2. Click on the "Delete Equipment" button.
3. A dialogue box will appear (See FIG. 37—"Deleting" Equipment Devices).
4. Select OK.

To retrieve deactivated equipment please e-mail the System Administrator with the equipment details.

Modifying Equipment (Model Number Change)

Improvements are developed that can be applied to existing Equipment Devices built as one Model, creating a new Model. The Serial Number of the device remains the same. This is actually handled by creating a new "virtual" Location described below.

Scrapping Equipment

A process is followed for the scrapping of Equipment Devices. At the end of this process a Scrapping Report is distributed to the EqT Admin (Inventory Specialist), among others. The following is an example session in which the EqT Admin or Writer can change the status of the Equipment Device to Scrapped.

1. Search for the Equipment.
2. Select Details.
3. Select Edit on the Details Window and change Ownership to "None".
4. Create a new Placement Type with date of the Scrapping report and choosing a Placement Type=SCRAP and Location=SCRAPPED. The guidance provided above with respect to Placing Serial Numbered Equipment Devices should be followed dependent on the type of Equipment Device being scrapped. Changing the Ownership field to "None" automatically changes the "On GL/Off GL" field to "Off". There is no other authority to move Equipment Devices to the virtual Location of SCRAPPED.

Returned Equipment

Equipment Devices returned by Sales Executives or Customers are always associated with a RA issued by the Shipping/Receiving Department or Quality Assurance (QA). Receiving provides EqT Admin with the validated RA form. EqT Admin or Writer places those validated Equipment Devices according to the information on the RA form following instructions provided above with respect to Placing Serial Numbered Equipment Devices as appropriate. The RA# for both Returning equipment and Replacement Equipment is automatically populated in Equipment Details in the Current RA Field.

Inventory Procedures

EqT Admin also is the Inventory Specialist. This individual is responsible for reconciling physical inventory of devices against the information stored in the system.

Department/Organizational Inventory Processes

Physical inventories are reconciled monthly for Sales Executives, Stock, Research and Development, Training, and Manufacturing.

Sales Executives

Sales Executives are required to provide a spreadsheet indicating Model and Serial Number for Serial Numbered equipment, and Model and quantity for Non-Serial Numbered equipment for everything in their inventory. The date the inventory is conducted is determined by the company(s). Photographs displaying the product label (both box and on the equipment device) may also be required.

EqT Admin runs a report for the Sales Exec and manually compares it to the listing provided by the Sales Executive. This action is completed for each Sales Executive in the company.

Any discrepancies are noted and sent via e-mail to the Sales Executive and their manager with a request for clarification. Sales Support may also be copied. The Sales Executive is expected to provide the Bill of Lading (BOL) to identify what location the equipment has been placed (in the event there is "missing" product from the Sales Exec's inventory) or the appropriate Pick-Up Sheet if there is additional product in the sales exec's inventory.

If the Sales Exec can not locate the missing equipment, the EqT Admin sends an e-mail to the Sales Exec and manager indicating that the equipment is "Lost". The Placement Type for that Equipment Device is updated to "Unknown", under the Sales Exec's Location.

Stock

The Shipping/Receiving Manager is responsible for finished goods (Equipment Devices) stored in Stock and conducts a monthly inventory of all Models and Serial Numbers, and Models and quantities for non-serial numbered equipment devices. A report is provided to EqT Admin on the designated inventory date for reconciliation. EqT Admin runs a report for the Stock Location and manually compares to the spreadsheet provided by the Shipping Manager. Any discrepancies are e-mailed to the Shipping Manager for correction.

If the Equipment Device is not found, EqT Admin updates the Placement Type to "Unknown", under the Stock Location.

R&D

R&D follows the same process as Stock, with the R&D Admin providing a report on inventory items to EqT Admin.

Training

A responsible Sales Manager or Sales Support Admin is designated to conduct physical inventory of Equipment Devices assigned for Training purposes. These individuals provide a report on inventory to EqT Admin and the same process used for Stock is followed.

Manufacturing

The EqT Admin provides a report on Equipment Devices to the Manufacturing Admin. This is used to locate all Equipment Devices under the Manufacturing Location. Discrepancies are identified and noted on the report.

EqT Admin researches missing and extra Equipment Devices as reported by the Manufacturing Admin and updates the Placement Type to "Unknown" for those items not found. For "extra" Equipment Devices, the Placement Type is updated to "MFG One".

Lost Equipment

Equipment Devices with an "Unknown" Placement Type are periodically reviewed by the EqT Admin. The EqT Admin will request updated information or specific searches of likely Locations based on a review of Placement History, Sales Executive activity for the time period in which the Equipment Device was lost, validation of existing BOLs, Scrapping Reports, etc.

Every effort is made to identify the location of missing equipment. After a period of time (To Be Determined), Unknown Placement Types are moved from the Locations from which they were "lost" and moved to a Location "Unknown" with the Placement Type "Unknown". The following is an example session.

1. Search for the Equipment.
2. Select Details.
3. Select Edit on the Details Window and change Ownership to "None".
4. Create a new Placement Type with date the Equipment is determined to be lost and choose a Placement Type=UNKNOWN and Location=UNKNOWN.

Upon discretion, Equipment Devices with Placement Type "Unknown" and Location "Unknown" are considered disposed and are dispositioned appropriately in Accounting Inventory and Fixed Assets Systems. The "On GL/Off GL" field is automatically updated to "Off" for equipment with an Ownership of "None".

Managing Resources

The EqT Admin is the only role that has permission to make changes in the Resources area.

Managing Locations

EqT Admin can add new Locations and edit existing Locations, including changing the status of a Location from Active (new Placements can be made for this Location) to Inactive.

Manage Locations is accessed by hovering over Resources Menu on the Menu Bar and selecting Locations.

Searches can be conducted using the Locations page.

Editing Locations

The following is an example session to edit locations.

Figure 38:
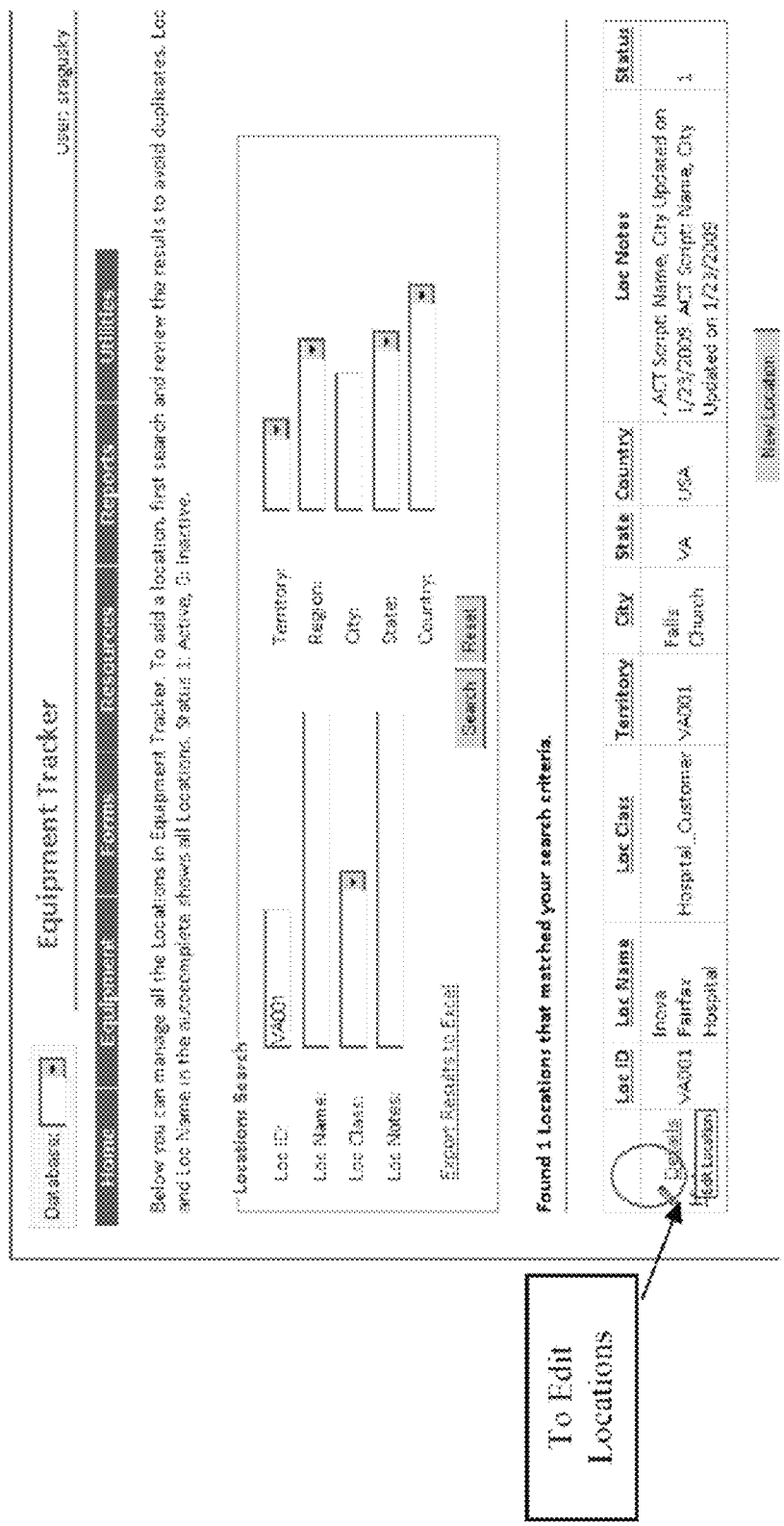
FIG. 38 is a schematic illustration of an example graphical user interface screen for managing locations.
Figure 39:
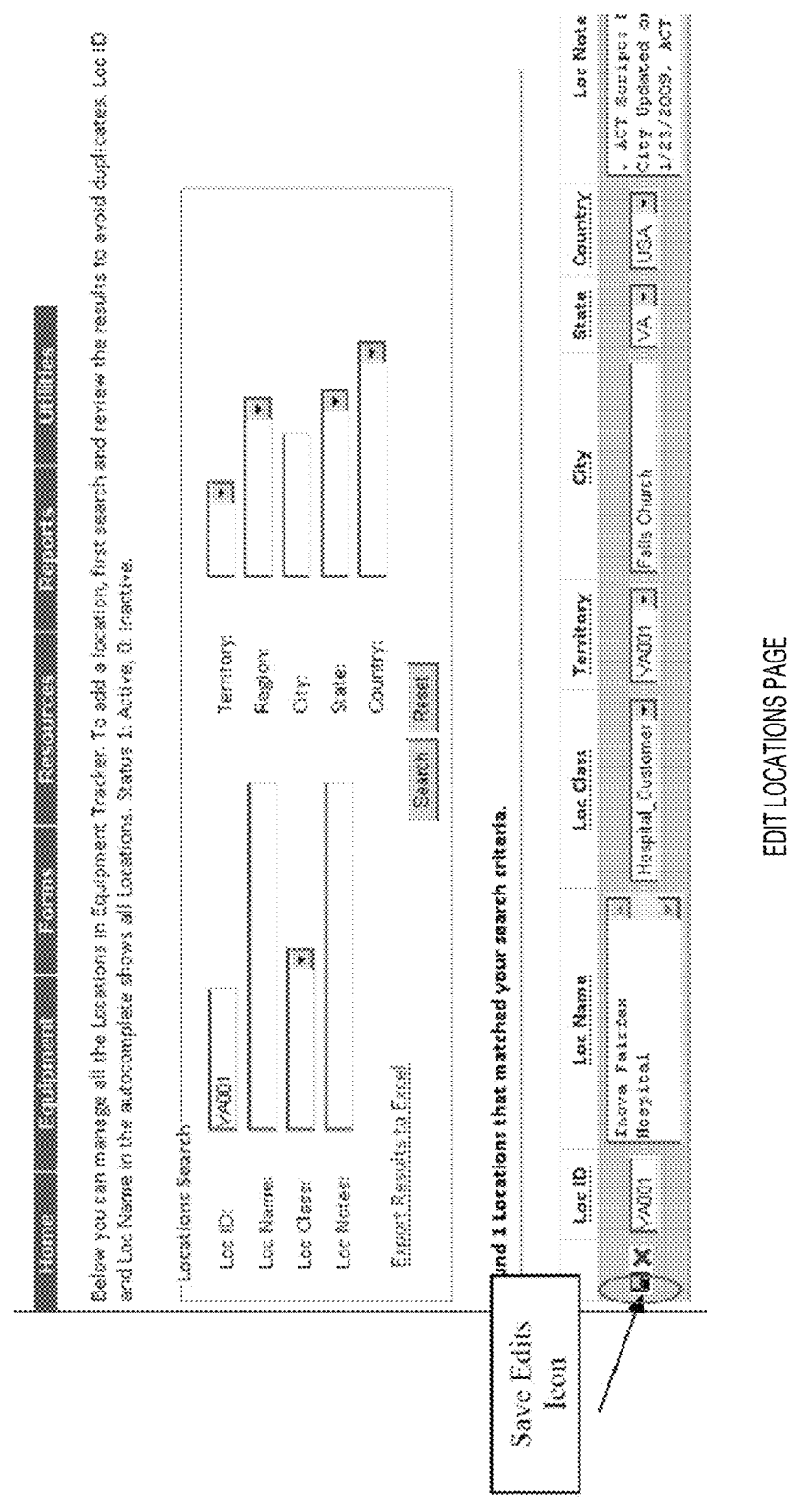

1. To edit, search for the Location you want to edit and click on the "pencil" icon in the left column of the Results Grid (See FIG. 38—Managing Locations).
2. The Row will change to edit format and you can change any of the fields as required (See FIG. 39—Edit Locations Page).
3. Make changes in the data entry boxes as appropriate and click on the save icon.

To cancel an edit click on the X.

New Locations

Locations are created when a Bill Of Lading (BOL) is received for an Equipment Device that is placed into a hospital/customer location for which there is no record. The EqT Admin must check ACT for verification of Location ID, Hospital/Customer Location Name, City, State and Country to validate the information on the BOL prior to setting up the new Location. The following is an example session to create a new Location.

Figure 40:
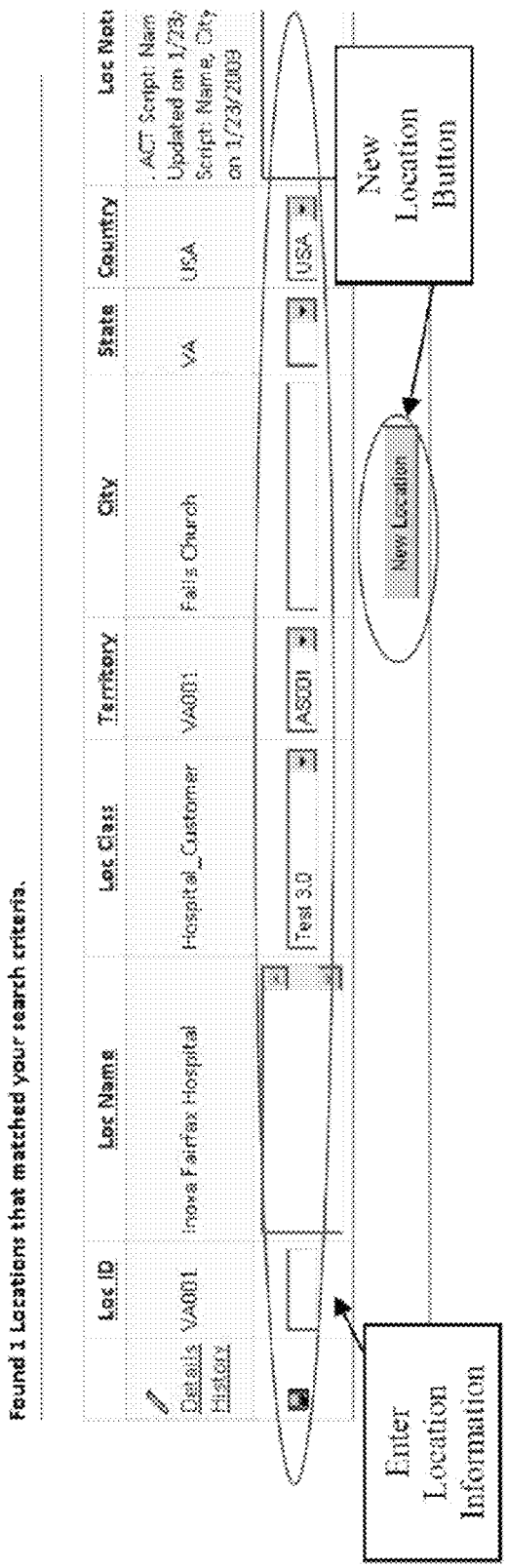
FIG. 40 is a schematic illustration of an example graphical user interface screen for creating new locations.

1. Scroll over Resources on the Main Menu Bar, selecting Locations.
2. Complete a SEARCH for the Location you want to create. The system forces a search prior to record creation to minimize duplicate entries. The system will prevent Locations with the same Account ID to be entered. You should first validate the information with ACT to minimize errors.
3. Search should result in No Hits, and the page will display the "New Location" button.
4. In order to create a new Location, there needs to be results in the Results Grid. Try searching on the state to generate results, and then click the New Location button.
5. A dialogue box will appear requesting confirmation that you want to create a New Location. Click Yes.
6. A blank Location entry row will appear at the bottom of the Results Grid. (See FIG. 40—Create New Location).
7. Enter the Location information; make sure to not enter spaces before or after the Location Name.
8. Click on the Save icon. Territory defaults to the first Territory in the pull down list.

Equipment Agreements

Equipment Agreements (EAs) are used for Loaned Equipment. All, some or none of the equipment at a Location may be under an EA. This is indicated by the system analyzing the number and type of equipment devices under an EA and comparing to the Equipment placed in Equipment Tracker. When looking at a Results Grid for a location search, the status of the EA equipment as compared to placed equipment is indicated by the COLOR of the Location ID (See FIG. 41—EA Status Indicator in Location). By way of example:

Green=EA exists and quantities in EA matches ET
Orange=EA exists but quantities do not match
Red=no EA exists Creating EAs EqT Admin and Writer can add new EAs and edit existing EAs. EAs are accessed by selecting the "Details" link within a Location Results Grid. The following is an example session.

Figure 42:
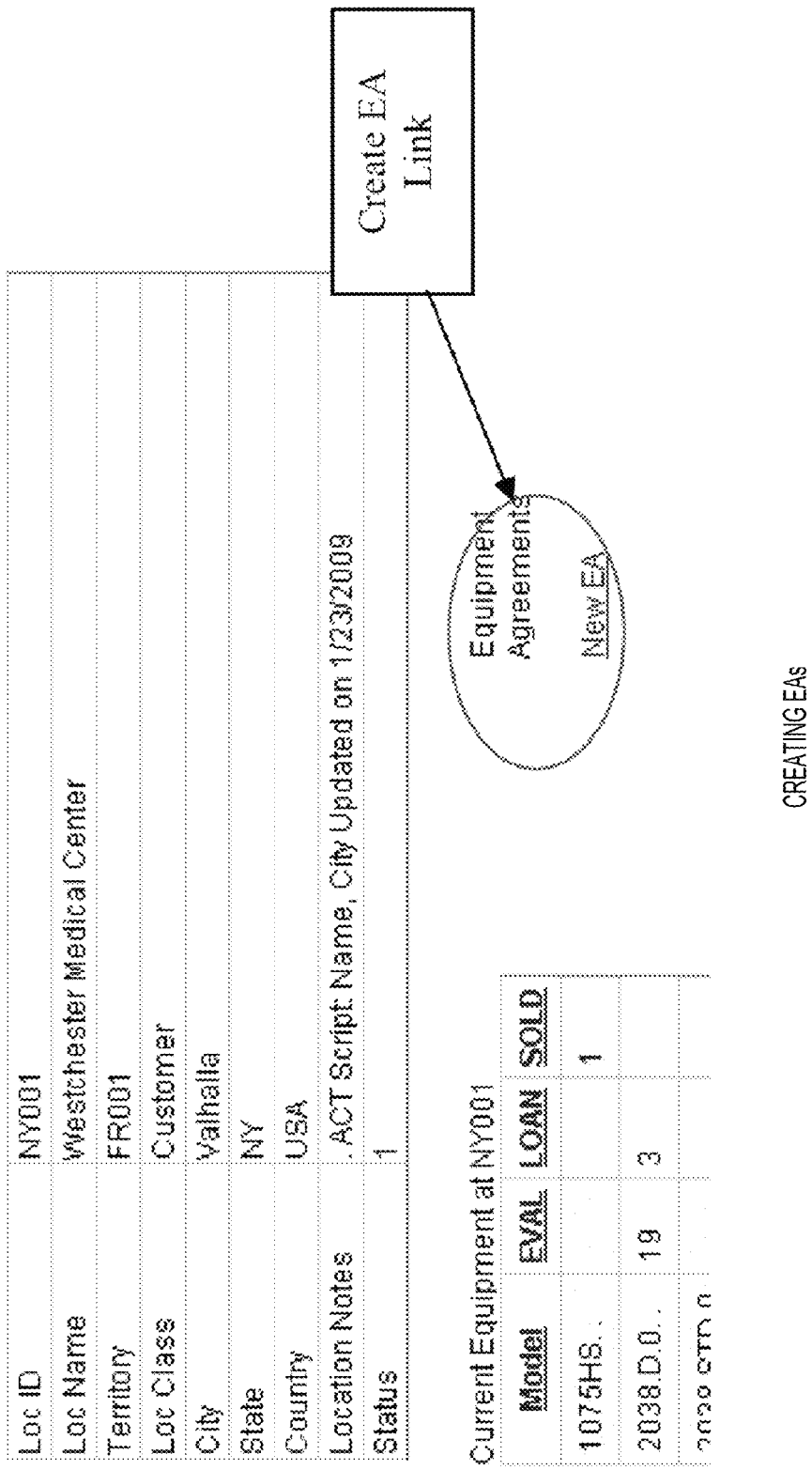
FIG. 42 is a schematic illustration of an example graphical user interface screen for creating equipment agreements.
Figure 43:
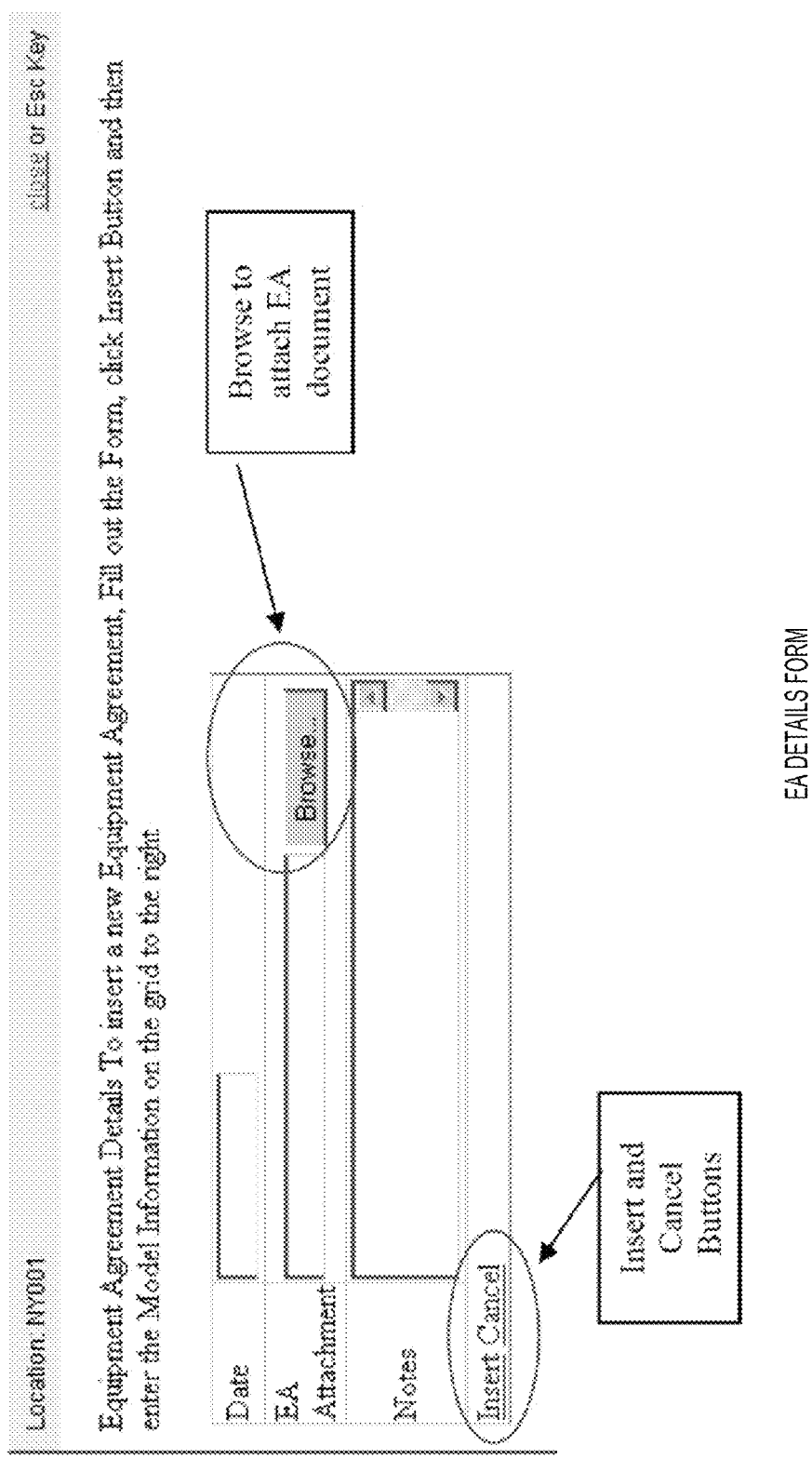
FIG. 43 is a schematic illustration of an example graphical user interface screen of an equipment agreement details form.
Figure 44:
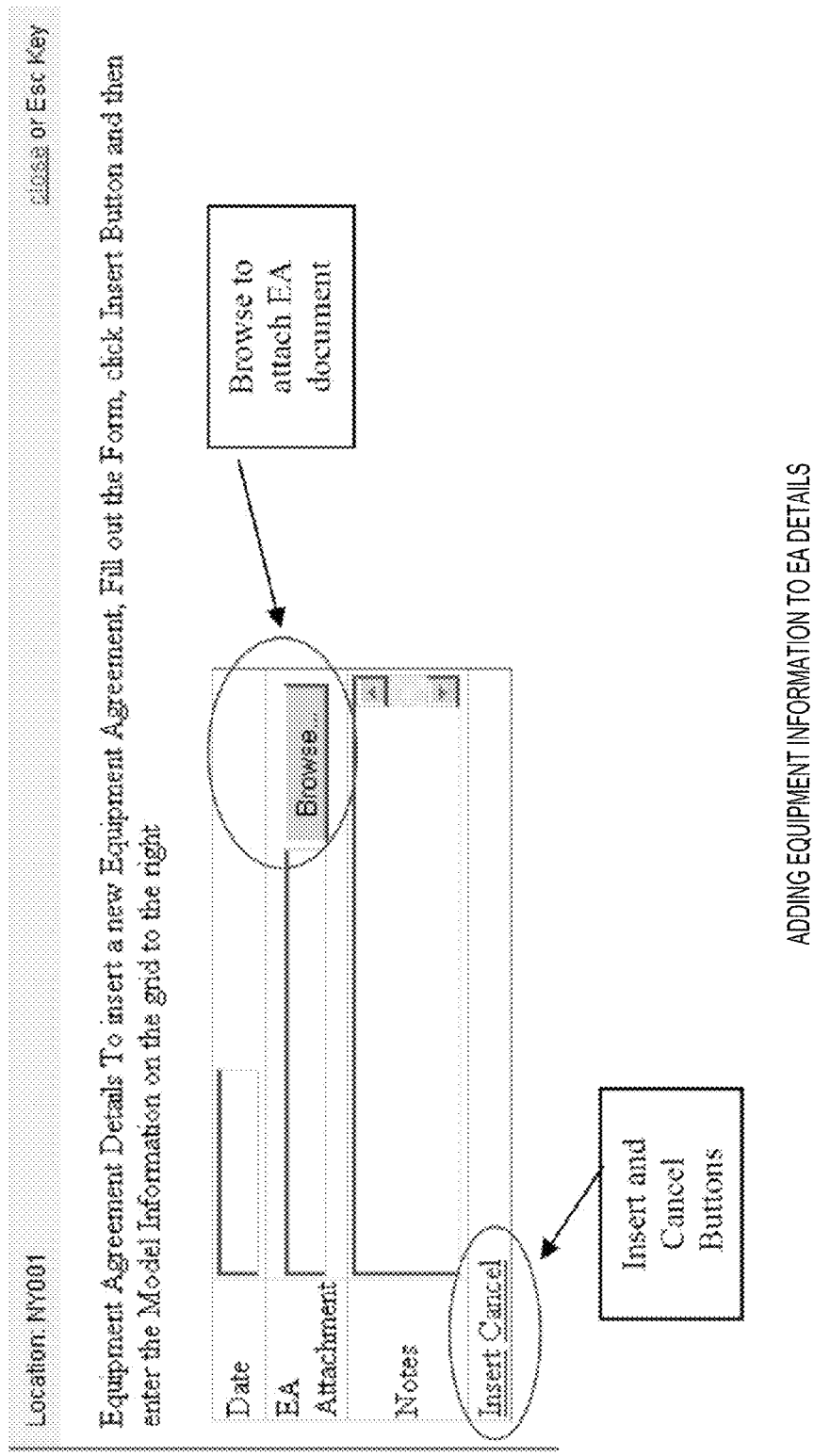
FIG. 44 is a schematic illustration of an example graphical user interface screen for adding equipment information to equipment agreement details.
Figure 45:
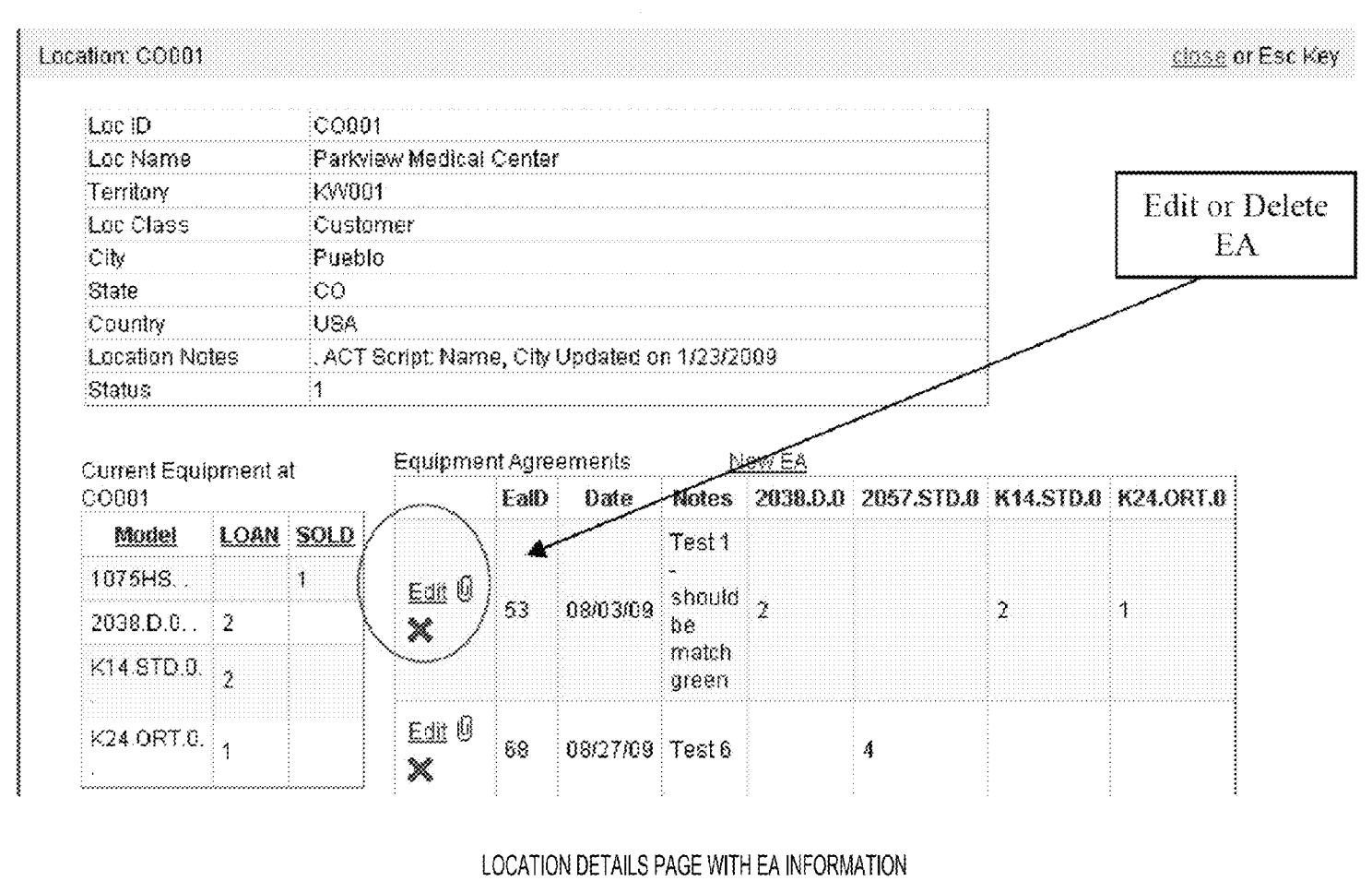

1. Scan the signed EA and re-name the file using format Account Number (Location ID)_EA_EADate. Ensure that the file is removed from the Scan Drive after uploading.
NY001_EA_8.28.09
2. Search for the Location ID.
3. Select Details in the Location Results Grid and the Location Details window will display (See FIG. 42—Creating EAs).
4. Select "New EA" on the Location Details window.
5. The EA Details Form will display (See FIG. 43—EA Details Form).
6. Fill in the EA Date using the calendar.
7. Use the Browse button to locate the EA Form created in step 1.
8. Add the EA attachment.
9. Add any appropriate notes.
10. Select insert. The title of the EA Attachment can not be changed once selected. To change the name you must cancel or delete the EA Details record and re-enter.
11. The EA Details window will update with the information and display a grid to add the model number and quantity of Equipment referenced in the EA (See FIG. 44—Adding Equipment Information to EA Details).
12. Select Model Number from the pull down box, enter quantity, and click the "Save" icon. Continue until all models covered by the EA are entered.
13. Click on the "Back to Location Details" button to return to the Location Detail page.
14. The Location Details page will be updated to show the new EA information (See FIG. 45—Location Details Page with EA Information).
15. Provide hardcopy EA to Inventory Control to update Placement Types from EVAL to LOAN.

16. The system analyses EA quantities against ET Placements overnight. Evaluate the Location/EA status by searching for the Location the day after Inventory Control has completed their update.

17. Multiple EAs can be added, if appropriate, to a single Location. Repeat steps 1-12 to add a second EA. The system will add total quantities covered by multiple EAs to conduct status analysis.

Editing EAs

EA Attachment Titles can not be edited once added to the Details window. You must delete the EA and recreate after naming the attachment correctly by selecting the X for the incorrect EA on the Location Details Page, EA Information. The following is an example session to edit existing EAs to correct quantities or change models.

1. Select "Edit" from the Location Details Page, EA Information for the EA to be updated.

2. The EA Details Page will display. Notes can be added, EA date can be changed, models can be deleted or added and quantities can be changed.

3. If an EA is replaced by a newer version, the original version(s) should not be deleted.

4. Add the new EA per steps in Creating EAs.

5. Edit the existing EAs by adding a model with the quantity set to "0" to the now obsolete EA.

6. Delete all other models in the obsolete EA by clicking on the X. Steps 5 and 6 ensure that it is clear there is no equipment under these historical EAs and that there is no missing data entry.

7. Click the save icon or the X to cancel the edit.

8. Select the "Back to Location Details" button.

9. The Location Status (color code) will update the next day.

Managing Placement Types

Sys Admin can add new Placement Types and edit existing Placement Types, including changing the status of a Placement Type from Active to Inactive. EqT Admin can also change Status from Active to Inactive.

Manage Placement Types is accessed by scrolling over Resources on the Main Menu Bar and selecting Placement Type.

Editing Placement Type

Typically, editing Placement Types is done to change Status from Active to Inactive or to correct a typographical error. The following is an example session.

1. To edit a Placement Type, scroll over Resources on the Main Menu Bar and select Placement Types.

Figure 46:
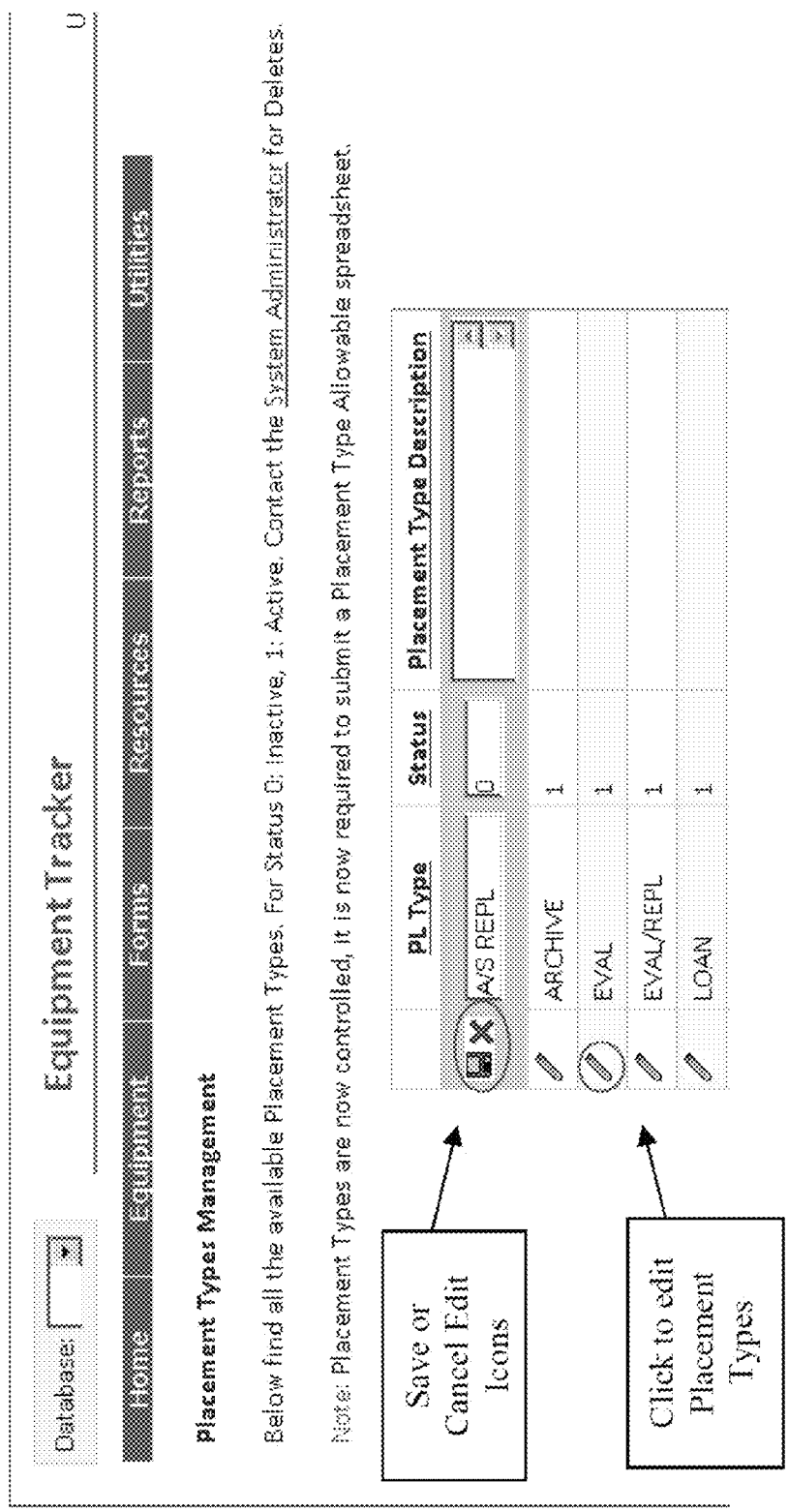
FIG. 46 is a schematic illustration of an example graphical user interface screen for editing placement types.

2. The Results Grid for Placement types will display (See FIG. 46—Editing Placement Types).

3. Click on the "pencil" icon for the Placement Type you want to edit.

4. Change the text in the PL Type box or Status field as appropriate.

5. Click on the save icon to save or the X to cancel the edit. The PL Type Name has to be unique or the update will fail.

Creating Placement Types

The Sys Admin creates new Placement Types based on operational requirements and in coordination with the Sales Department. The following is an example session to create a new Placement Type.

1. Scroll over Resources on the Main Menu Bar and select Placement Types.

2. Review the Placement Types list to ensure the new Placement Type does not already exist.

Figure 47:
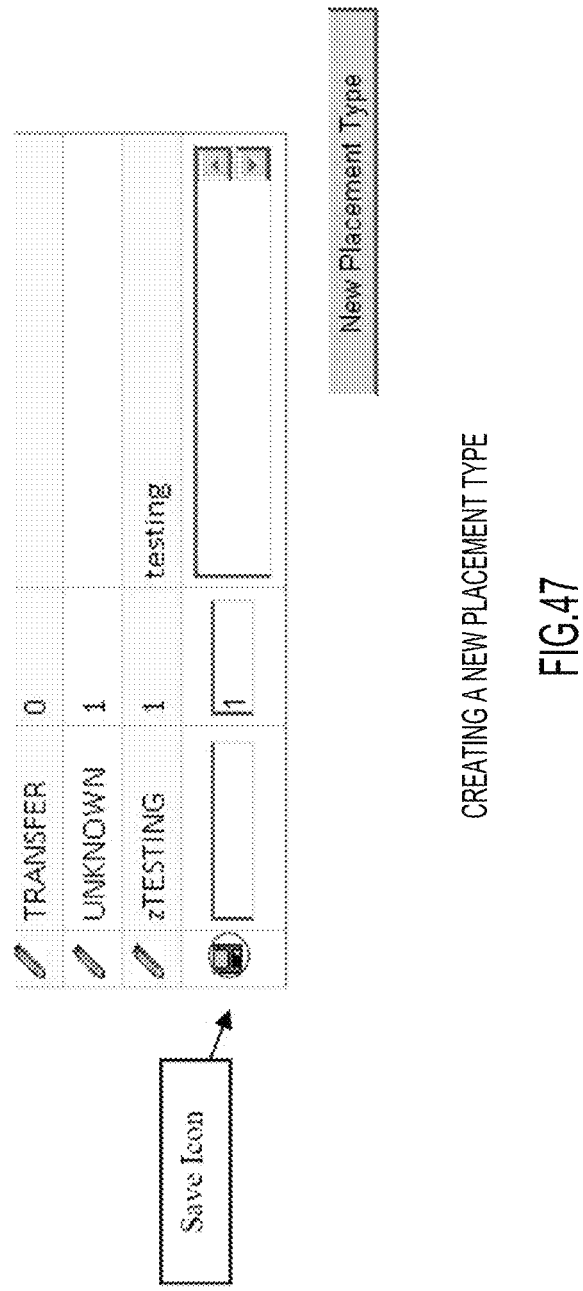
FIG. 47 is a schematic illustration of an example graphical user interface screen for creating a new placement type.

3. Scroll down to the bottom of the Placement Type Results Grid and click on the "New Placement Type" button. (See FIG. 47—Creating a New Placement Type).

4. Enter the new Placement Type. Status automatically defaults to "1" or Active.

5. Click the save icon. The System Administrator is the only user who can delete Placement Types.

Managing Models

The EqT Admin can edit and create Model information. Model information is provided on Finished Goods Delivery Notices (FGDN) for New Equipment and for Repaired Equipment. Additional details are provided by QA and confirmation on Model information should be obtained from QA prior to editing or adding Model information.

Editing Models

The following is an example session.

1. Scroll over Resources on the Main Menu bar and select Models.

2. The Models Results Grid will display (See FIG. 48—Editing Models).

3. Click the Edit icon (pencil) to edit fields as appropriate. Status field values:
 1=Active serial numbered equipment,
 2=Active accessories or non-serial number equipment
 0=Inactive cannot be used to create new Equipment Devices Creating Models The EqT Admin creates new Models based on operational requirements and in coordination with Manufacturing and QA. The following is an example session to create a new Model.

1. Scroll over Resources on the Main Menu Bar and select Model.

2. Review the Models list to ensure the new Model does not already exist.

Figure 49:
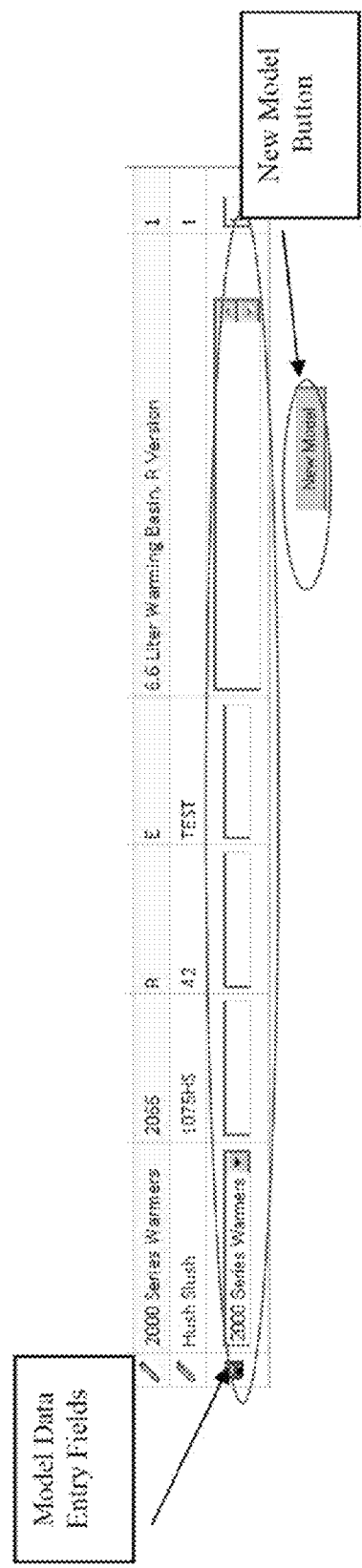
FIG. 49 is a schematic illustration of an example graphical user interface screen for creating models.

3. Using the right hand scroll bar, move to the bottom of the Models Results Grid and click on the "New Model" button. (See FIG. 49—Creating Models).

4. Complete the information in the data entry fields that appear at the bottom of the Models Results Grid.
 a. The Model Number, Configuration, and Product Level combination must be unique. Catalogue defaults to the first item in the Catalogue Results Grid. Status defaults to "1", which is Active Serial Numbered Equipment.

5. Click the save icon. Incorrect entries can be removed by the System Administrator.

Modifying Models

Periodically existing Equipment Devices may be upgraded from one Model to another (examples are new Product Levels and new Configurations). The following is an example session for this type of activity.

1. Create new Model as described above.

2. Create a Location as described above and enter Location Name as "Modified to XXX", where XXX identifies the new Model information. Locations of this type are "COMPANY" locations and numbers should be assigned as NNNMO, where NNN is the next sequential number available for the Location MO or "Modified".

3. Search for Equipment Devices affected by the upgrade as described above.

4. Create a Placement with a Placement Type of "MODIFIED" and place at Location "Modified to XXX". FIG. 50—Examples of Modified Equipment Devices displays Modified Equipment devices.

5. Create a new Equipment Device under the New Model created in Step 1 using the same Serial Number of the Equipment Device.

6. Create a new Placement (typically STOCK as these types of changes are delivered via a Repair Finished Goods Delivery Notice).

7. Verify Condition Code is correct. Default is "N" for New.

8. Create a new Placement that documents the Placement Date of the original equipment model and ensure the Placement Type is New. This ensures the correct age of the equipment is reflected when depreciating Fixed Assets or determining the value of inventory.

Managing Catalogues

Only the EqT Admin can add new Catalogues and edit existing Catalogues, including changing the status of a Catalogue from Active to Inactive. Catalogues are logical groupings of Models and are determined by QA in coordination with the respective Sales Department.

Manage Catalogues is accessed by scrolling over Resources on the Main Menu Bar and selecting Catalogue.

Editing Catalogues

The following is an example session.

Figure 51:
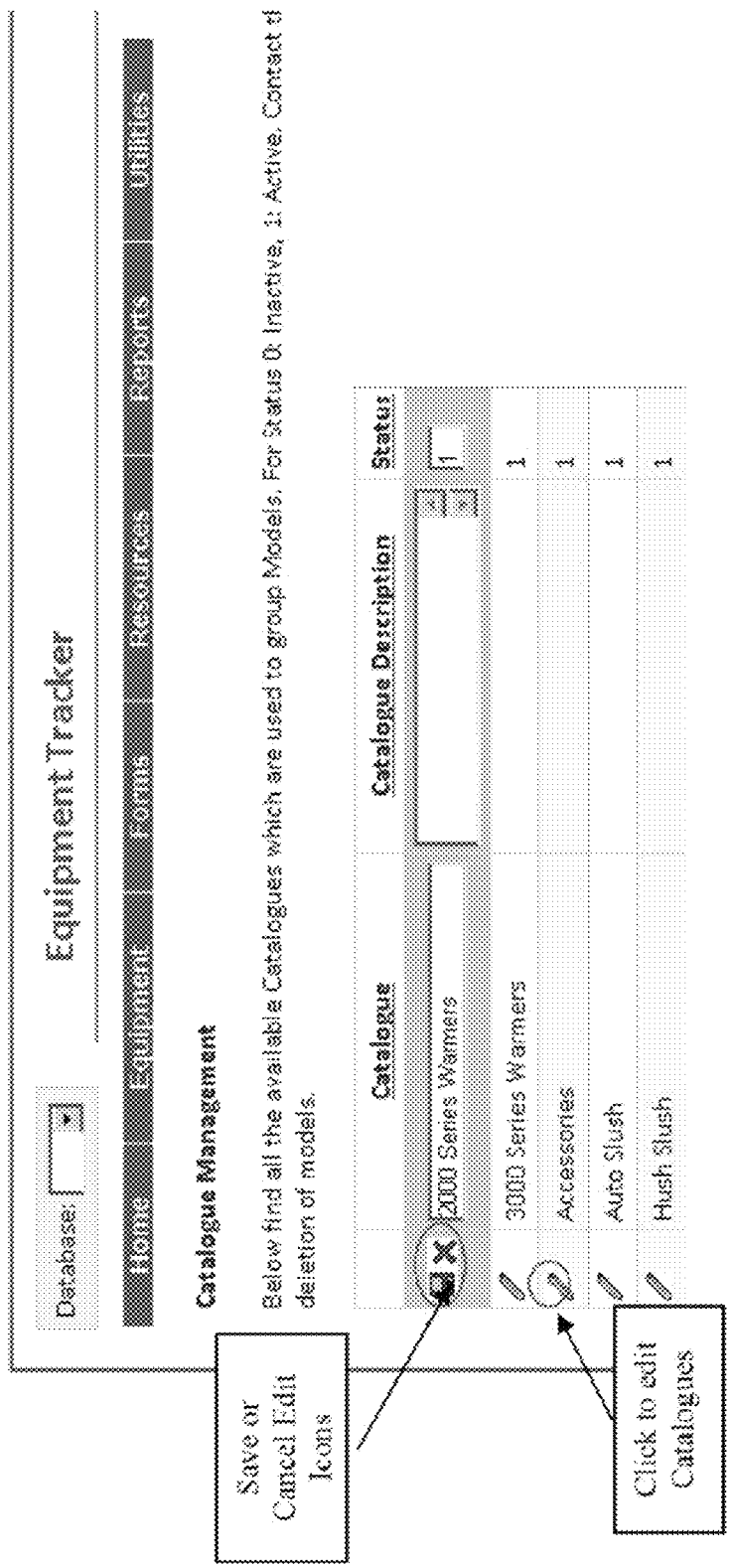
FIG. 51 is a schematic illustration of an example graphical user interface screen for editing catalogues.

1. To edit, click on the "Edit" icon in the left column of the Results Grid (See FIG. 51—Editing Catalogues).

2. Complete the appropriate edits using the fields presented.

3. Click the save icon to save or the X to cancel the edit. Incorrect entries can be removed by the System Administrator.

Creating Catalogues

The EqT Admin can create Catalogues. The following is an example session.

1. Scroll over Resources on the Main Menu Bar and select Catalogues.

2. Review the Catalogues list to ensure the new Catalogue does not already exist.

Figure 52:
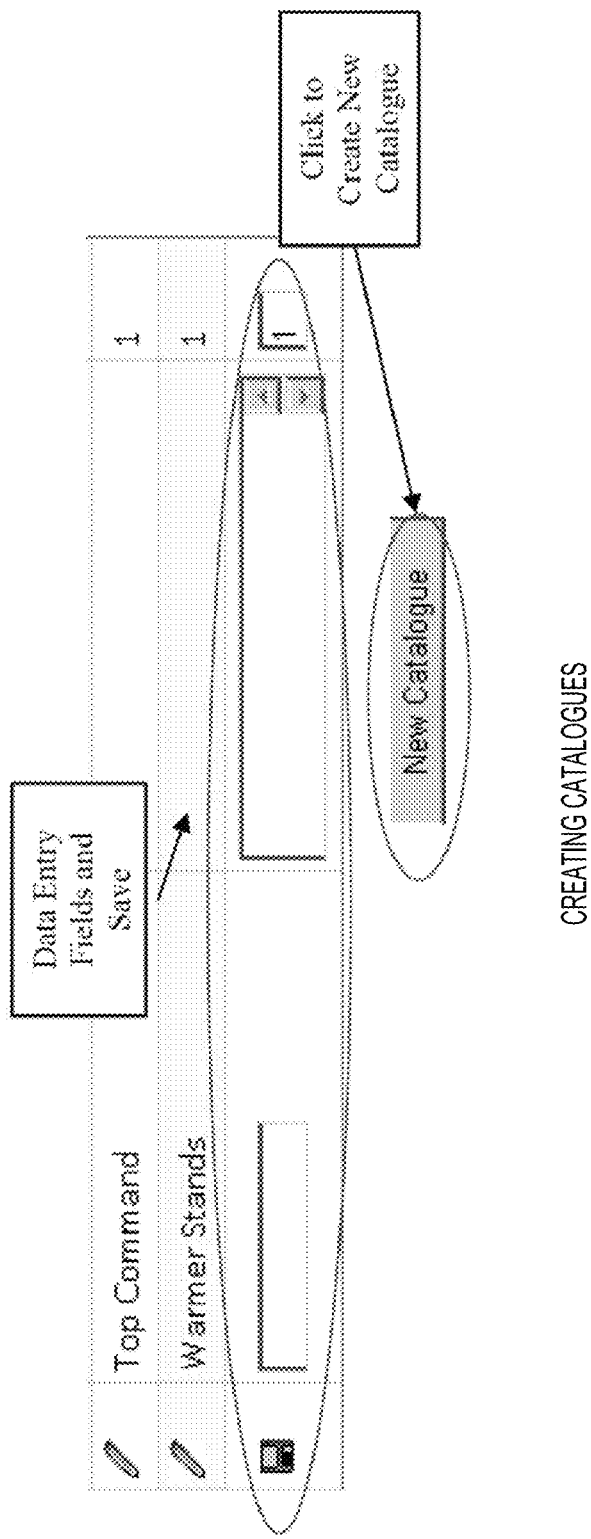
FIG. 52 is a schematic illustration of an example graphical user interface screen for creating catalogues.

3. Using the right hand scroll bar, move to the bottom of the Catalogues Results Grid and click on the "New Catalogue" button. (See FIG. 52—Creating Catalogues). Catalogue Name must be unique.

4. Complete the data entry fields and click the Save icon to save the entry. Incorrect entries can be deleted by the System Administrator.

Managing Territories

EqT Admin can add new Territories and edit existing Territories. Territories are assigned to individual Sales Executives and have an identifier. Description in Catalogues will be populated by the EqT Admin to describe the geographic area making up the Sales Territory. Each Hospital_Customer Location will be populated with their associated Territory. Territories also map to Regions described below.

Manage Territories is accessed by scrolling over Resources on the Main Menu Bar and selecting Territories.

Editing Territories

The following is an example session.

Figure 53:
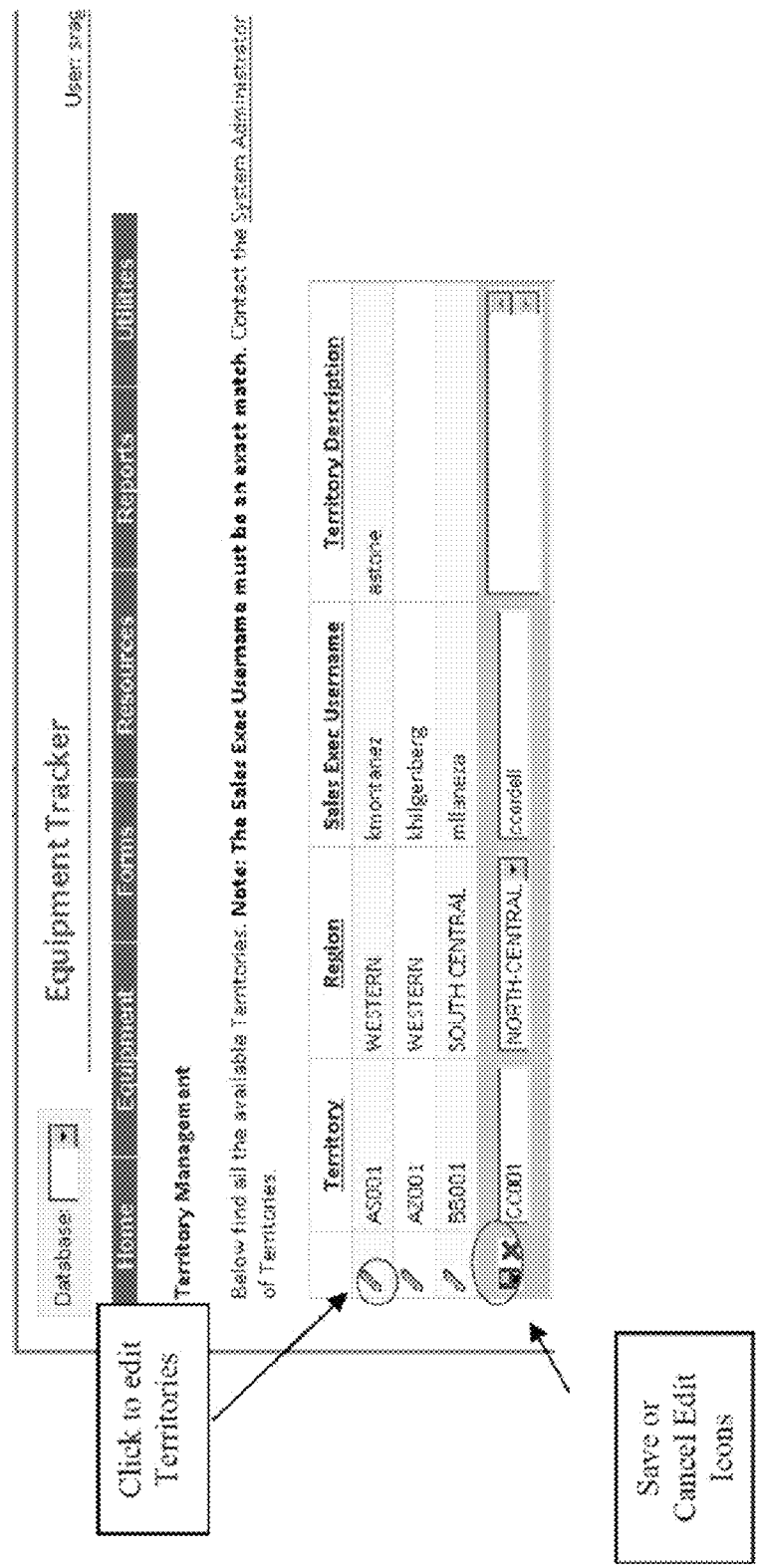
FIG. 53 is a schematic illustration of an example graphical user interface screen for editing territories.

1. To edit click on the "Edit" icon in the left column of the Results Grid (See FIG. 53—Editing Territories).

2. Complete the appropriate edits using the fields presented.

3. Click the save icon or the X to cancel the edit. Incorrect entries can be removed by the System Administrator.

Creating Territories

The EqT Admin can create Territories. The following is an example session.

1. Scroll over Resources on the Main Menu Bar and select Territories.

2. Review the Territories list to ensure the new Territory does not already exist.

Figure 54:
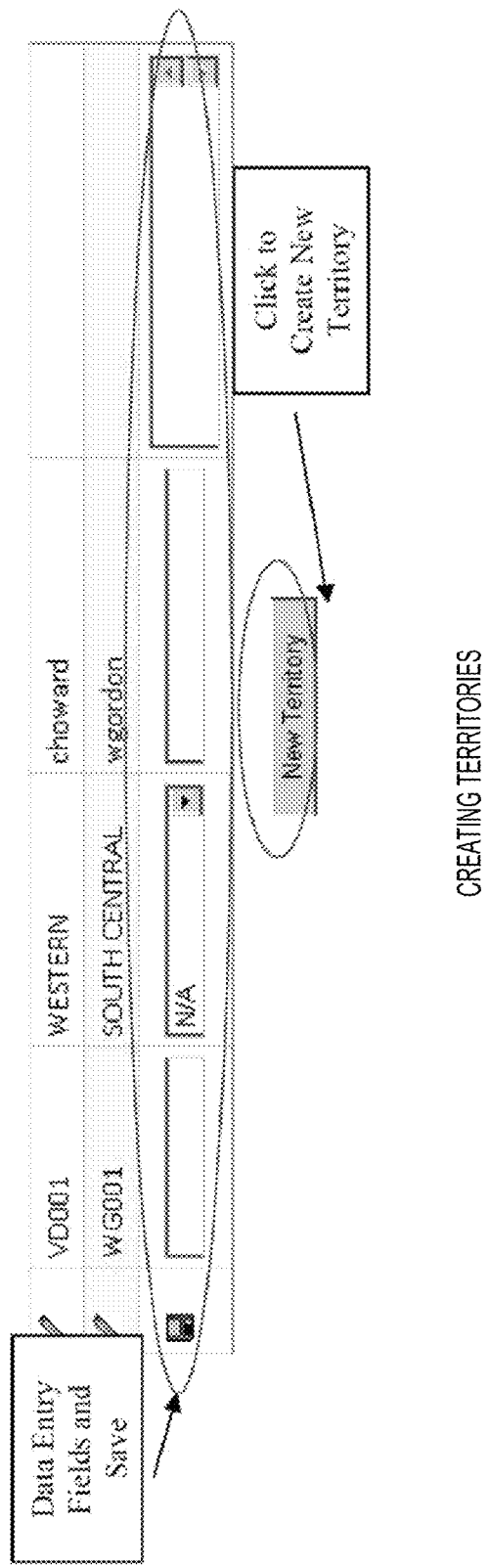
FIG. 54 is a schematic illustration of an example graphical user interface screen for creating territories.

3. Using the right hand scroll bar, move to the bottom of the Territories Results Grid and click on the "New Territory" button. (See FIG. 54—Creating Territories).

4. Complete the data entry fields and click the save icon. Incorrect entries can be deleted by the System Administrator. Territory Names must be unique.

Managing Regions

EqT Admin can add new Regions and edit existing Regions. Regions are assigned to Sales Managers and are comprised of Territories. The Description Field in Regions will be populated by the EqT Admin to describe the geographic area making up the Region. Each Hospital_Customer Location will be populated with their associated Region.

Manage Regions is accessed by scrolling over Resources on the Main Menu Bar and selecting Territories.

Editing Regions

The following is an example session.

Figure 55:
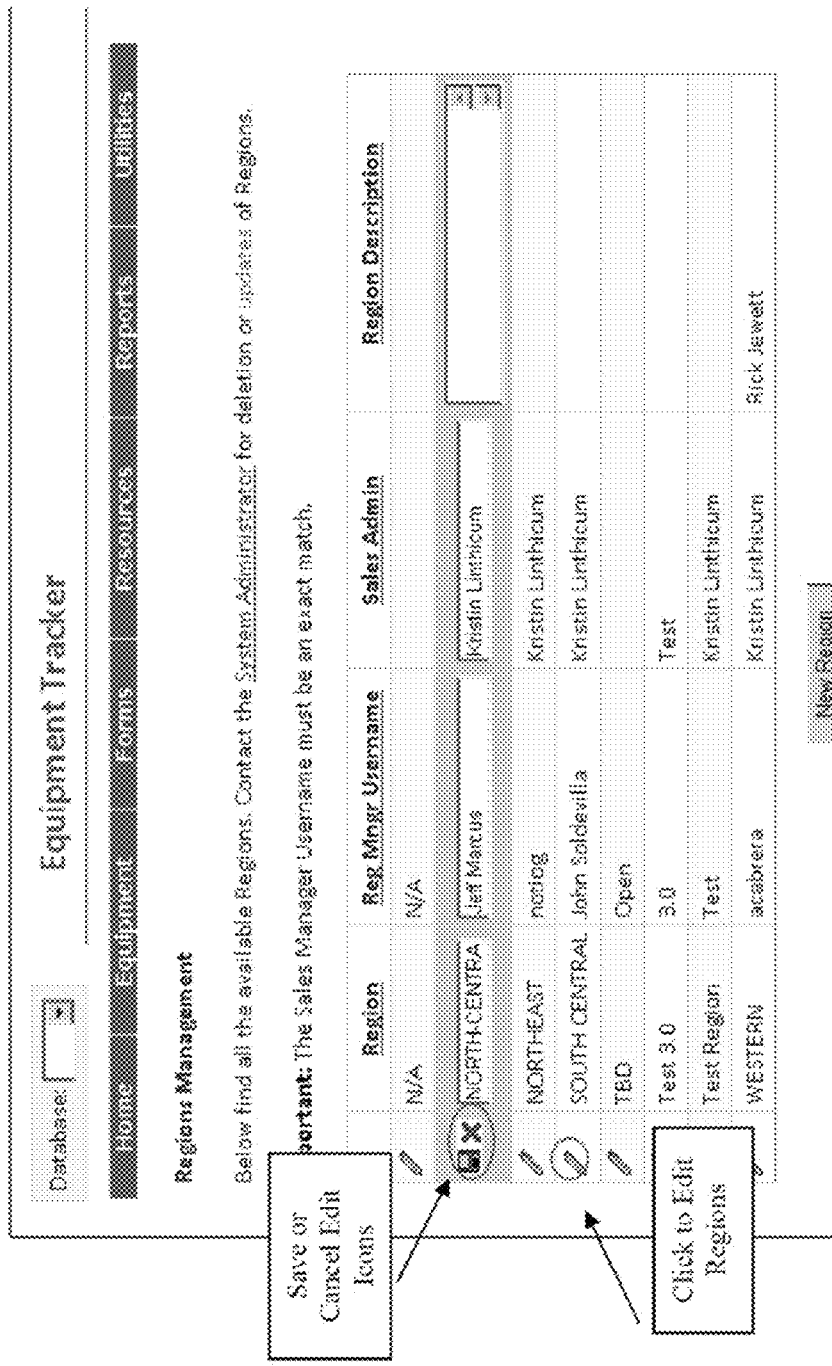
FIG. 55 is a schematic illustration of an example graphical user interface screen for editing regions.

1. To edit, click on the "pencil" icon in the left column of the Results Grid (See FIG. 55—Editing Regions).

2. Complete the appropriate edits using the fields presented.

3. Click the save icon or the X to cancel the edit. Incorrect entries can be removed by the System Administrator.

Creating Regions

The EqT Admin can create Regions. The following is an example session.

1. Scroll over Resources on the Main Menu Bar and select Regions.

2. Review the Regions list to ensure the new Region does not already exist.

Figure 56:
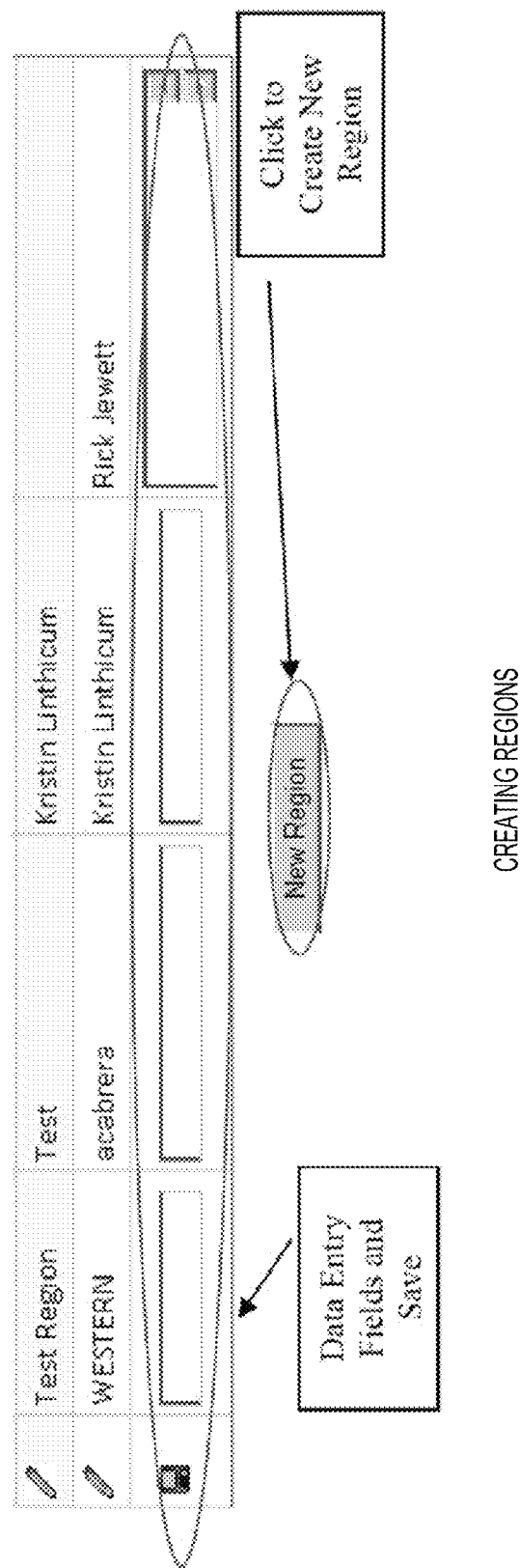
FIG. 56 is a schematic illustration of an example graphical user interface screen for creating regions.

3. Using the right hand scroll bar, move to the bottom of the Regions Results Grid and click on the "New Region" button. (See FIG. 56—Creating Regions).

4. Complete the data entry fields and click the Save icon to save the entry. Incorrect entries can be deleted by the System Administrator.

Managing Location Classes

Sys Admin can add new Location Classes and edit existing Location Classes, including changing the status of a Location Class from Active to Inactive. Manage Location Classes is accessed by scrolling over Resources on the Main Menu Bar and selecting Location Class.

Editing Location Classes

Typically, editing Location Class is done to correct a typographical error. The following is an example session.

1. To edit a Location Class, scroll over Resources on the Main Menu Bar and select Location Classes.

Figure 57:
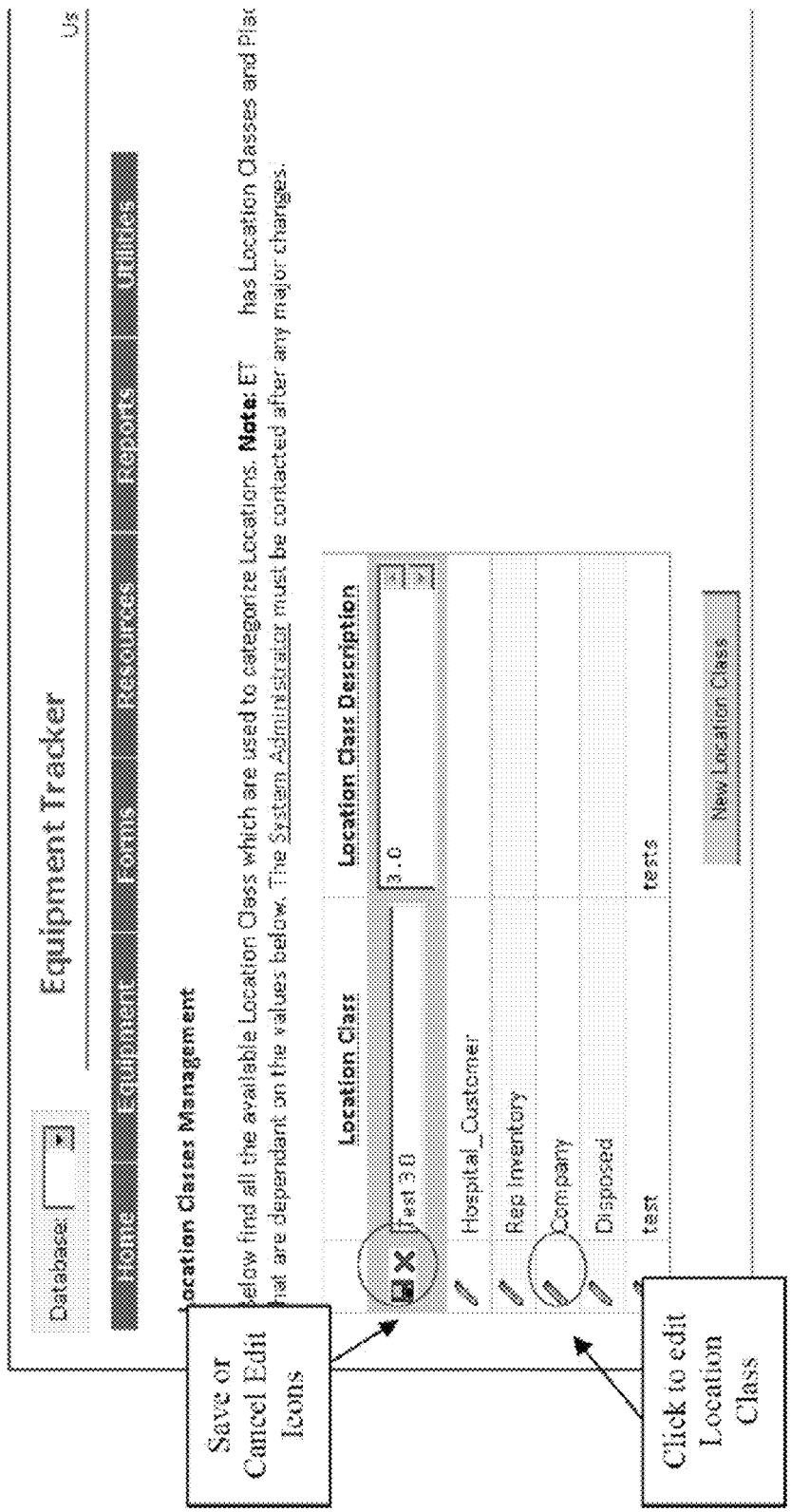
FIG. 57 is a schematic illustration of an example graphical user interface screen for editing location classes.

2. The Results Grid for Location Classes will display (See FIG. 57—Editing Location Classes).

3. Click on the "pencil" icon for the Location Class you want to edit.

4. Change the text in the Location Class box or Location Class Description field as appropriate.

5. Click on the save icon or the X to cancel the edit. The Location Class name has to be unique or the update will fail.

Creating Location Classes

The Sys Admin creates new Location Classes based on operational requirements and in coordination with the Sales Department. The following is an example session to create a new Location Class.

1. Scroll over Resources on the Main Menu Bar and select Location Class.

2. Review the Location Class list to ensure the new Location Class does not already exist.

Figure 58:
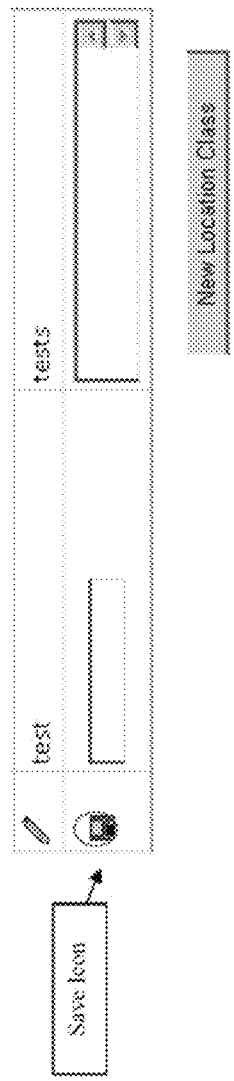
FIG. 58 is a schematic illustration of an example graphical user interface screen for creating a new location class.

3. Scroll down to the bottom of the Location Class Results Grid and click on the "New Location Class" button. (See FIG. 58—Creating a New Location Class).
4. Enter the new Location Class.
5. Click the save icon. The System Administrator is the only user who can delete a Location Class.

III. Users With "RA Writer", "QA Writer", "QA Director" or Similar Roles

Creating RAs

RA Writer, QA Writer and QA Director can create RAs. There are various types of RAs.
  Equipment RAs=created from the Equipment Search page.
  Drape RAs=created from Quality on the Main Menu Bar.
  Parts RAs=created from Quality on the Main Menu Bar.
Standard Operating Procedures for RAs are:
  Equipment RAs are generated by a Customer Location (Hospital), Sales Executive or internal department such as Research and Development, contacting the Shipping Department via telephone or email. The RA Writer role is the primary role used to create Equipment RAs. QA Writer and QA Director can create Equipment RAs, and Parts RAs, but typically only create an RA in association with a Complaint. RAs are required for moving equipment from any location back into Stock. RAs automatically update status and information as Equipment moves through the Return and Replacement Process.
    Customer Locations will be directed to QA based on the assumption that there is some issue requiring technical support.
    Sales Executives and internal departments not requiring Replacement Equipment will contact Shipping/Receiving for RA generation.
  Drape and Parts RAs are generated by a Customer Location contacting Customer Service.
  Equipment RAs can be generated by a Customer Location contacting the Quality Assurance Department and reporting a Complaint for a piece of Equipment. The RA is generated as part of the Immediate Corrective Action within the Complaint process.

Creating Equipment RAs—Non-Complaint

Figure 59:
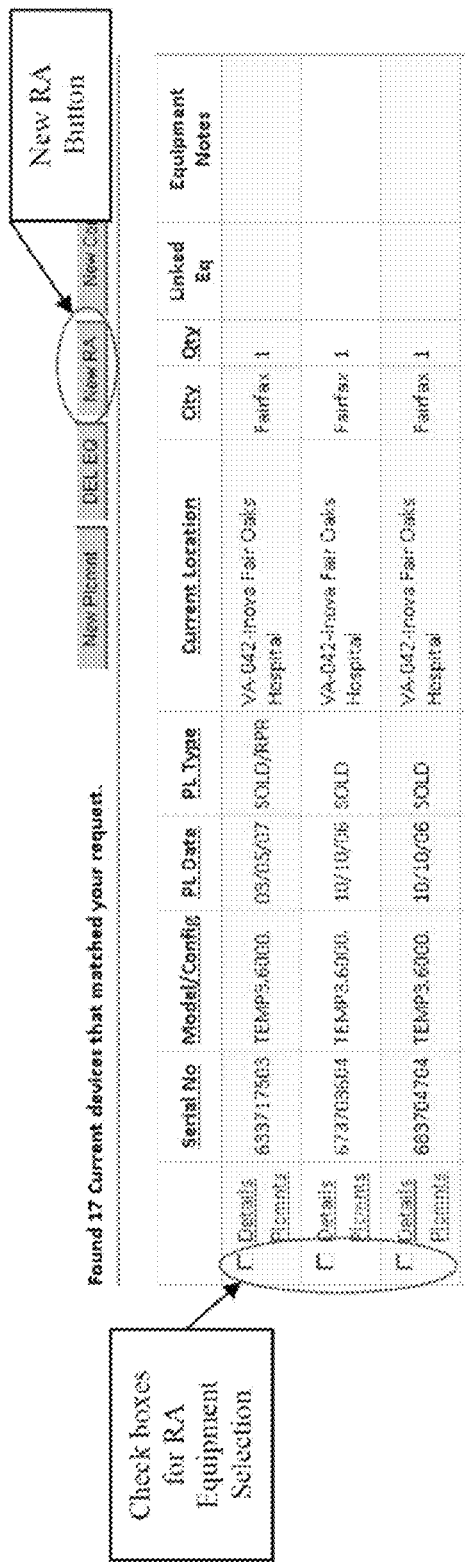
FIG. 59 is a schematic illustration of an example graphical user interface screen for creating a return authorization (RA).
Figure 60:
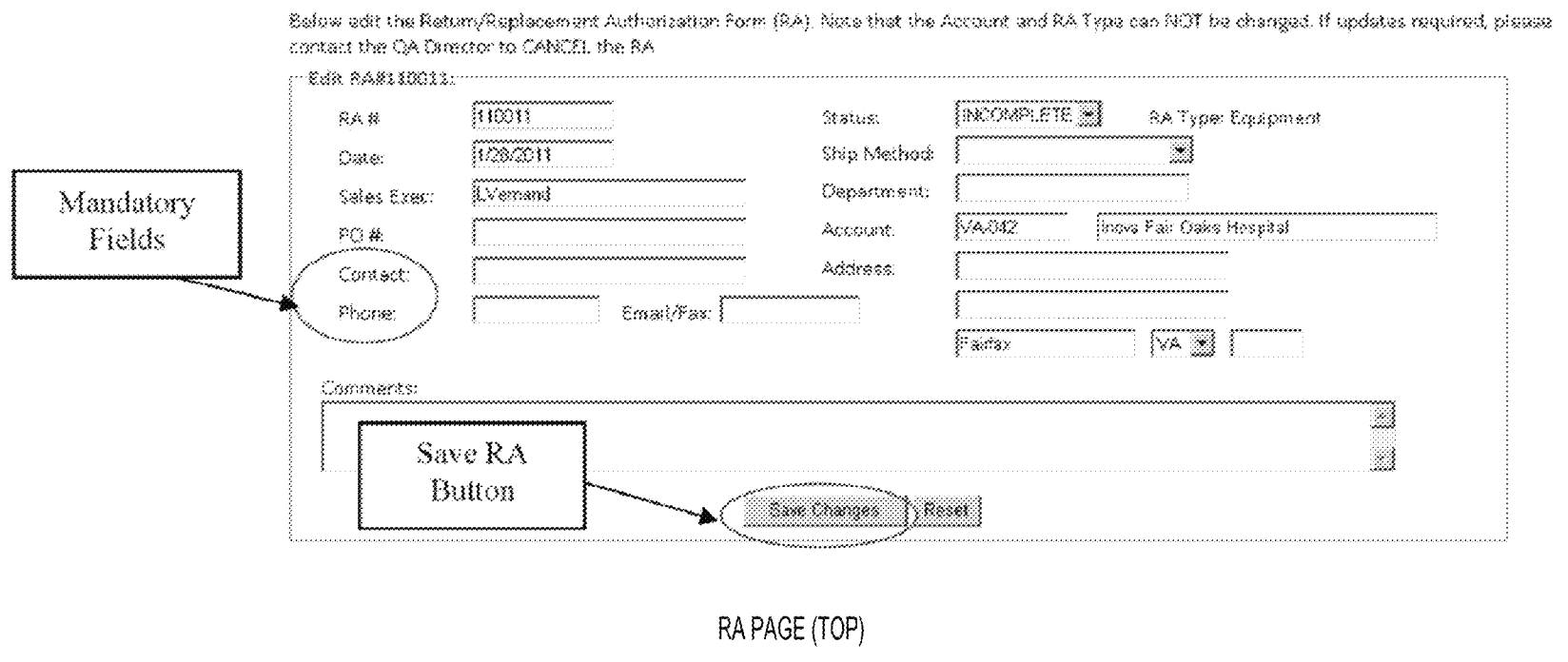

The following is an example session.
1. Select "Search" under "Equipment" on the Main Menu Bar.
2. Enter required information to find the equipment being returned. If a single item is being returned, a search by Serial Number may be the most effective method. If multiple items from a location are being returned, a search by Location ID or Location Name will be most effective.
3. Click the check box(es) by the equipment to be returned.
4. Click the "New RA" button (See FIG. 59—Creating a RA). Equipment being returned on an RA must meet two requirements.
  Equipment must have the same ownership (the exception is when certain equipment is owned by a Customer. Details for handling are provided below).
  Equipment must be returned from the SAME location.
5. RA Page will display (See FIG. 60—RA Page (Top)).
  RA Number is automatically assigned.
  RA Date is filled in with the date the record is created.
  Sales Executive name is filled in (if applicable).
  RA Type is Equipment.
  Account ID (or Location ID), Location Name, City and State are completed.
  Status defaults to Incomplete.

Figure 61:
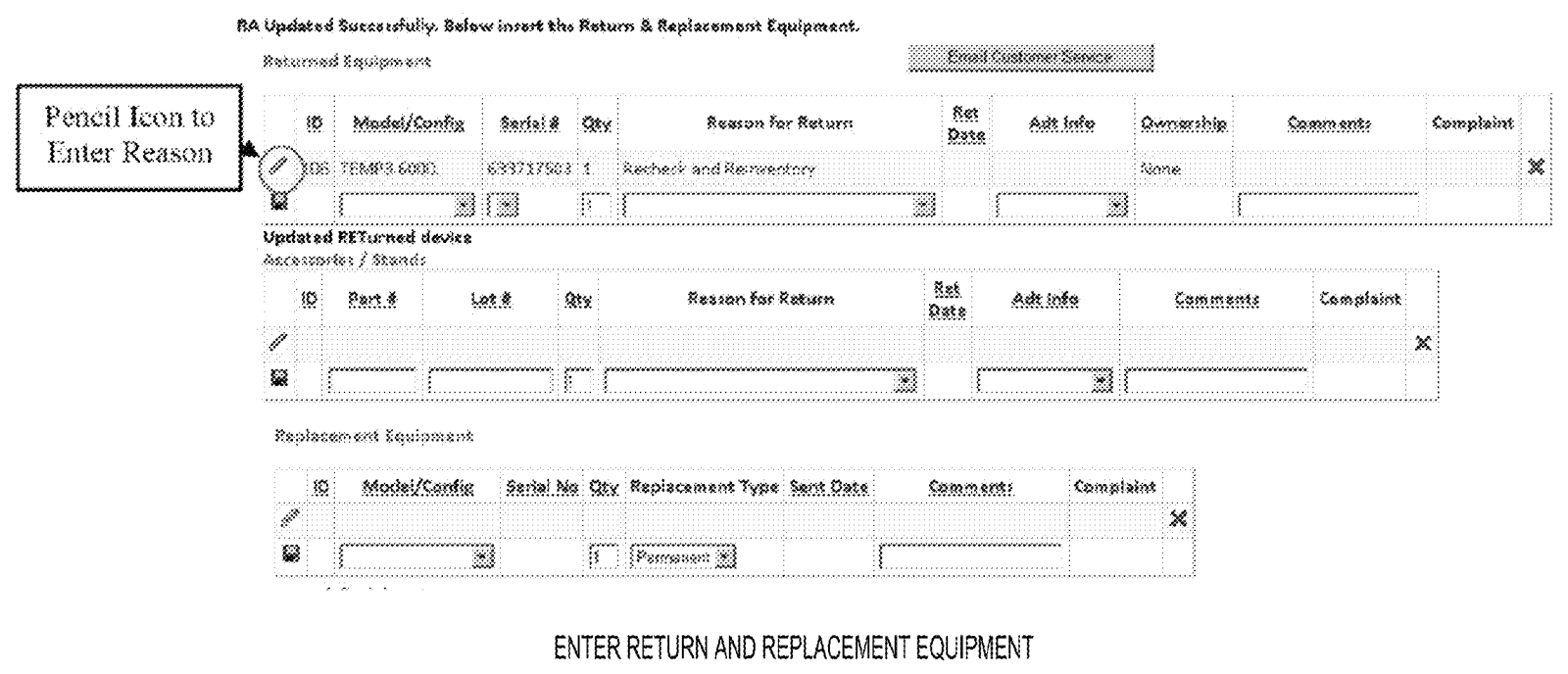
Figure 62:
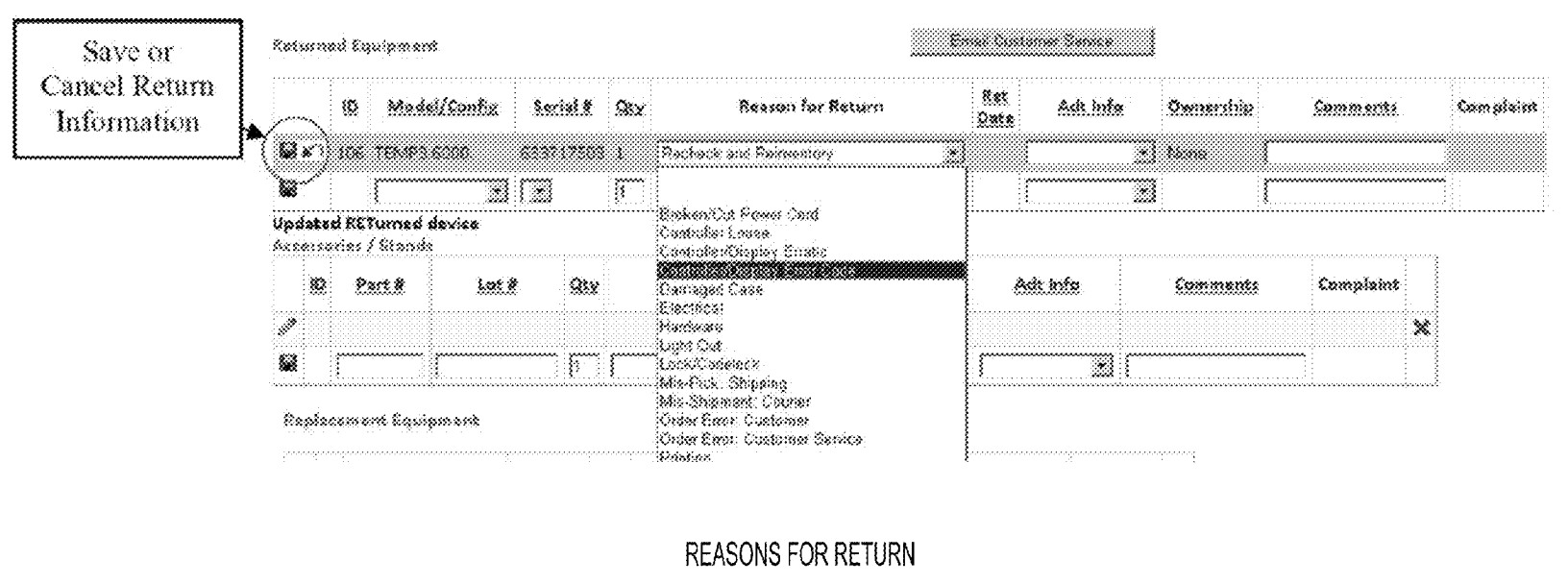
Figure 63:
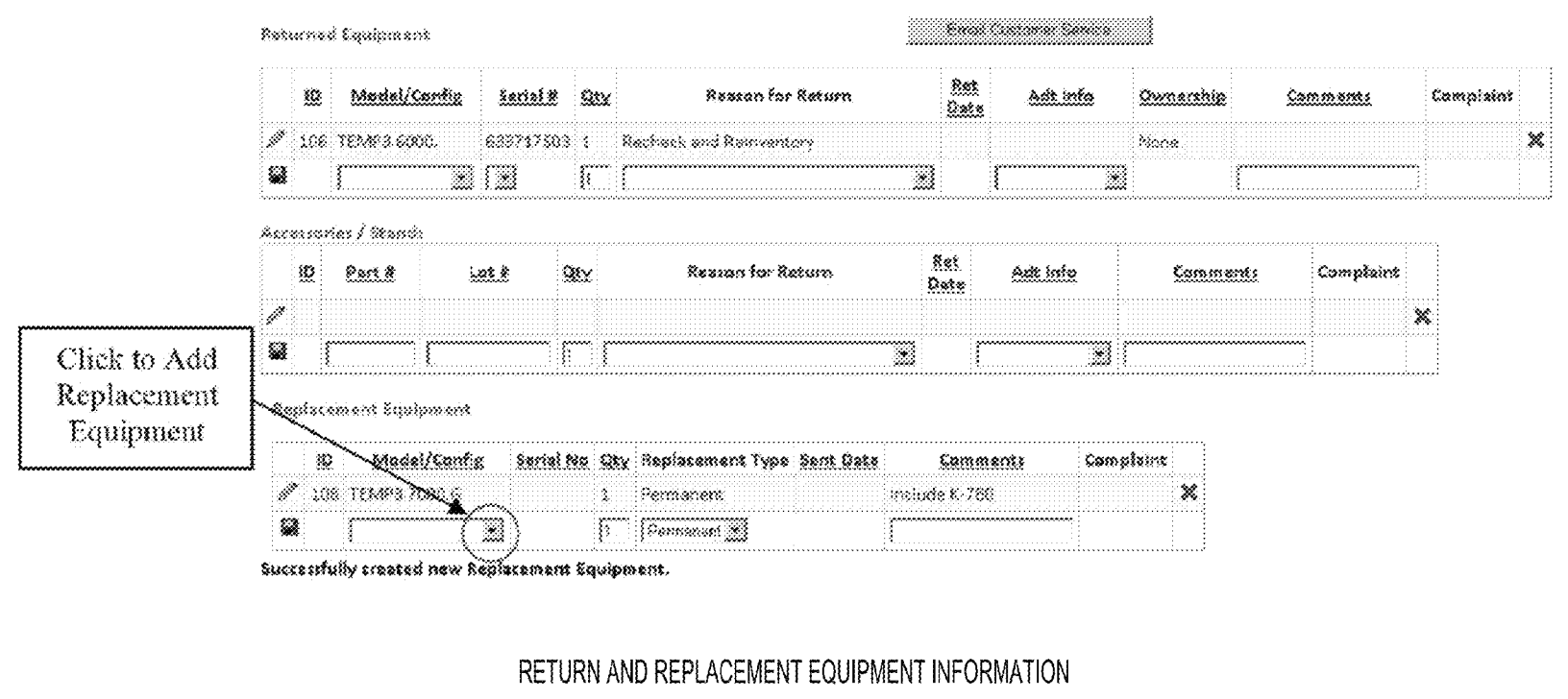

6. Enter Contact Name and Phone Number (Mandatory Fields). The Account and RA Type can NOT be changed. The RA must be canceled if an error is made at this stage. If the Location the equipment is being returned from is a Sales Executive's Inventory Location, the Contact Name, Phone Number and Email will automatically be filled in.
7. If Replacement Equipment is being sent, select the Shipping Method and enter the address information.
8. Click on "Save Changes" button.
9. Message will be returned the "RA Updated Successfully. Below insert the Return & Replacement Equipment". (See FIG. 61—Enter Return and Replacement Equipment).
10. Confirm Model and Serial Number for Returned Equipment are correct.
11. Click on "Pencil Icon" for first piece of Returned Equipment and select Reason for Return. (See FIG. 62—Reasons for Return). The shipping department usually selects 'Recheck and Re-Inventory' or 'Return to Inventory' as any other Reason for Return would indicate a Complaint is required. Reason for Return is a Mandatory Field. List options are managed by the QA Director per instructions as described below.
12. Add Comment and/or select Additional Information if appropriate. Comments can also be added at the RA level, in addition to adding a comment for a specific piece of equipment. Text beginning and ending with '' (e.g., Sample Text**) will be displayed in the header area of a printed RA form, preferably in RED, to provide lifecycle support for processing the returned equipment. This feature is normally used to identify if the equipment should be directed to QA or MFG QA rather than standard return processing.
13. Click Save Icon. The Curve Arrow Icon cancels the edit of the Returned Equipment.
14. Click Pencil Icon and repeat steps for each remaining piece of equipment.
15. Confirm data is correct and Status of RA has updated from Incomplete to Active.
16. To delete a piece of equipment from the RA, click the X on the right of the Equipment Grid.
17. To enter Stands, use the Accessories/Stands Tables. Accessories and Stands are tracked differently.
18. Enter Part Number (e.g., K-780), enter '0' in the Lot Number, select the appropriate quantity, select Reason For Return.
19. Click the Save icon to save the Accessory/Stand information.
20. To enter Replacement Equipment, click on the Model arrow in the Replacement Equipment Table. (See FIG. 63—Return and Replacement Equipment Information). Replacement Equipment models listed are models available for shipment from Inventory.
21. Select the Model by clicking on the arrow and selecting from the pull down menu. Replacement Type defaults to Permanent. Change to Temporary if appropriate. Add comments, if applicable (for example, include K-780). Temporary Replacement equipment is sent for Customer owned equipment or equipment with an Ownership of Rental. Temporary can not be selected for Company owned equipment.
22. Click on the Save Icon to save Replacement Equipment information.
23. Receive message that Replacement Equipment created.
24. Click on Email Customer Service Button.
25. Message that Customer Service Department is notified to create packing slip for Replacement Equipment is displayed and e-mail is sent to Customer Service. See FIG.

64—E-mail to Customer Service Replacement Equipment. The e-mail to Customer Service contains the information required to create the Packing List for the Replacement Equipment. A link to the RA is also provided in the e-mail. The link allows Customer Service to obtain reference information to add to the Packing List (reminders on returning equipment).

26. The Shipping Department receives an e-mail noting Update of the RA with a link provided when the RA is created as a result of a Complaint.

Adding Equipment to RAs

Figure 65A:
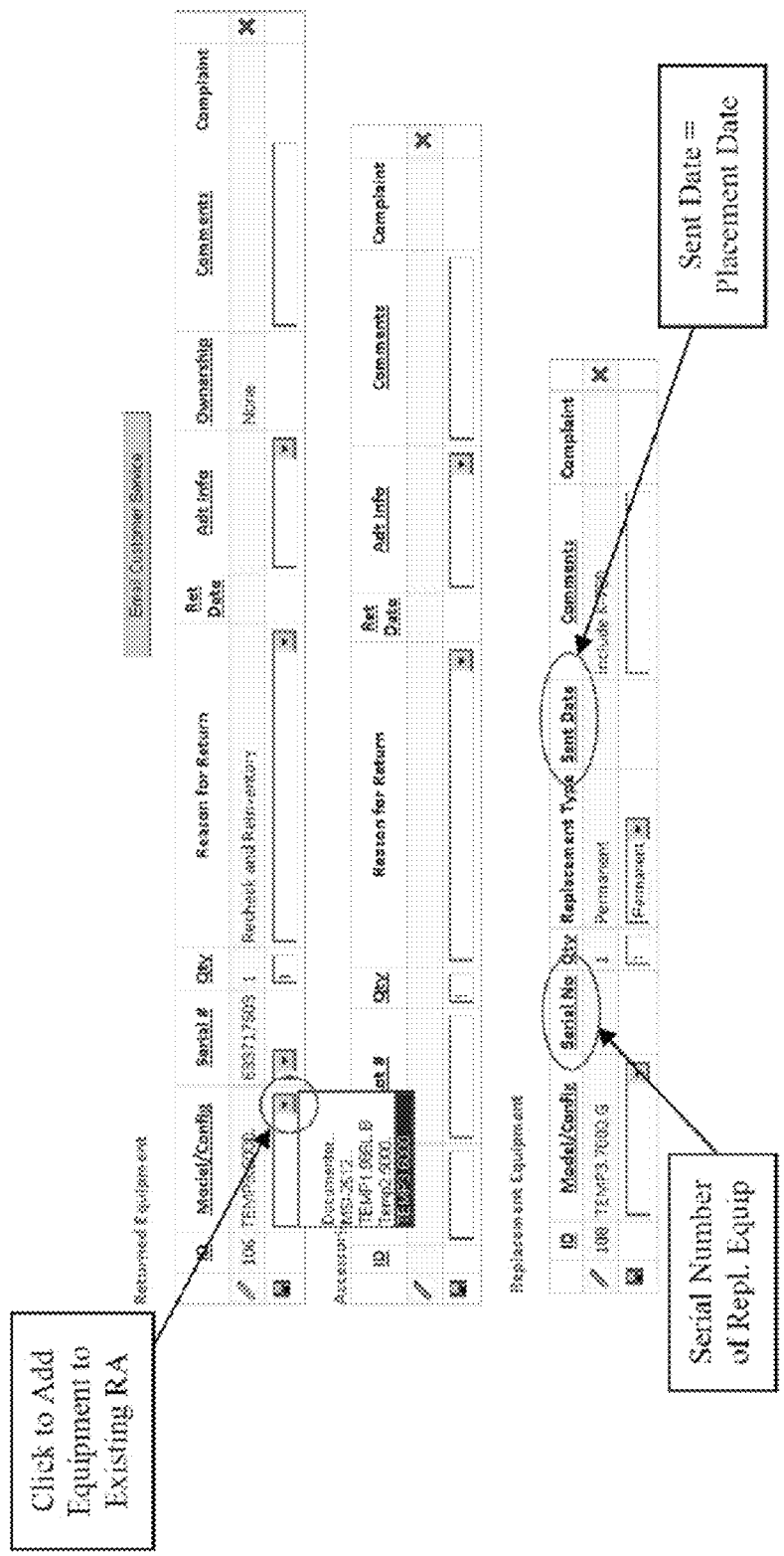
FIG. 65A is a schematic illustration of an example graphical user interface screen for adding equipment to an RA.

Equipment can be added to the RA by selecting the arrow as indicated in FIG. 65A—Adding Equipment to RA. Only those models and serial numbers at the location identified in the RA will display in the pull down menu. Shipping Department personnel should use their judgment on adding both Return and Replacement equipment to a RA. It is suggested that any equipment added to the RA should be completed within 24 hours of RA origination, or a separate RA should be issued. Replacement equipment should NOT be added without coordinating with the Customer Service Department first.

RA Status and Process Updates

RAs automatically update as Equipment moves through the Return and Replacement Process. Customer Locations returning equipment and requesting Replacement Equipment have this information documented on the RA form. The Shipping/Receiving Department enters the required information for Replacement Equipment. Customer Service is notified via an e-mail that captures the details necessary for creating a Packing List (e.g., See FIG. 64—E-mail to Customer Service Replacement Equipment). A link to the RA is also provided in the e-mail. The link allows Customer Service to obtain reference information to add to the Packing List (reminders on returning equipment). The following is an example session for Replacement Equipment shipped to a location that is returning equipment.

1. The EqT Admin, following standard process, will update information using the completed Packing List from the Shipping Department.

Figure 65B:
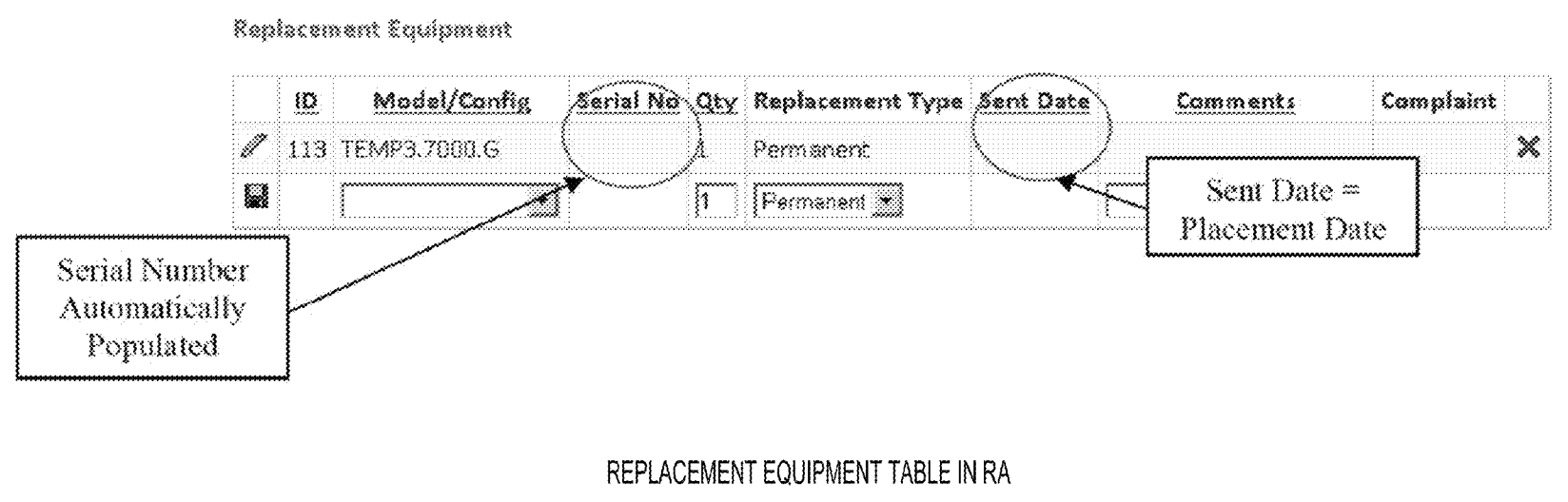

2. When the EqT Admin creates the new placement for the Replacement Equipment (e.g., moving equipment from Stock to a Customer Location), the Placement Date is automatically populated as the Sent Date in the Replacement Equipment Table in the RA. The Serial Number of the Replacement Equipment is also populated automatically (e.g., See FIG. 65B—Replacement Equipment Table in RA). If Replacement Equipment is "TEMPORARY" versus Permanent, the Status of the RA will update to "Pending" upon receipt of the Returned Equipment. The QA Department manually "Closes" the RA based on their assessment of the parameters required for closure. For example, the RA is not closed until the Temporary Replacement equipment is returned to Stock.

Returned Equipment also follows standard Equipment Tracking procedures. The RA Number is identified by the Shipping/Receiving Department when notifying EqT Admin of movement of Inventory into Stock. The following is an example session.

Figure 66:
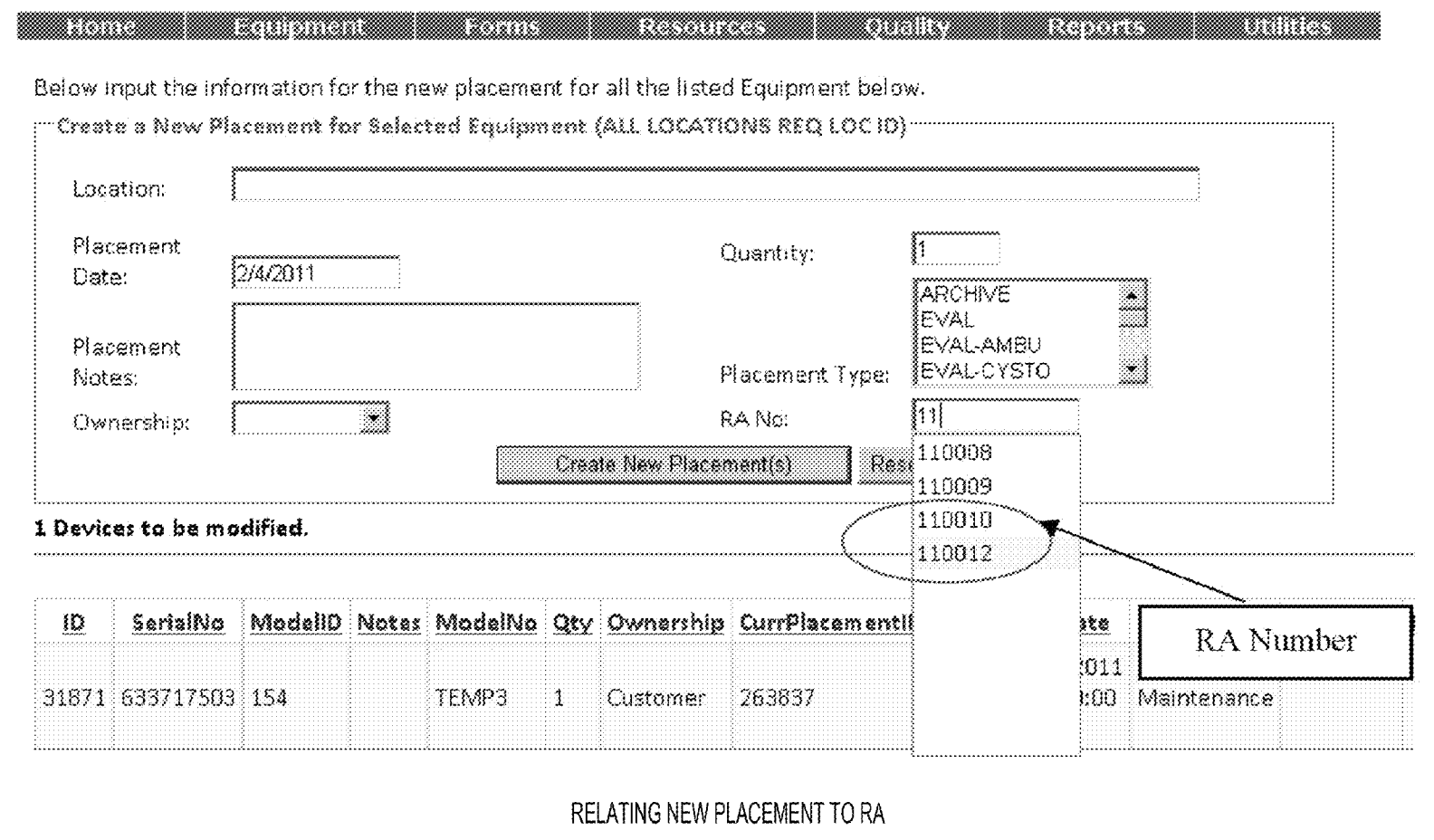

1. EqT Admin changes the Placement of the Equipment (e.g. Stock Location and Stock Placement Type) entering the RA Number to link the equipment movement to the RA. (See FIG. 66—Relating New Placement to RA).

2. The RA is automatically updated with the Status of the RA updated to "Partial Return" (since more than one piece of equipment is associated with the example RA).

Figure 67:
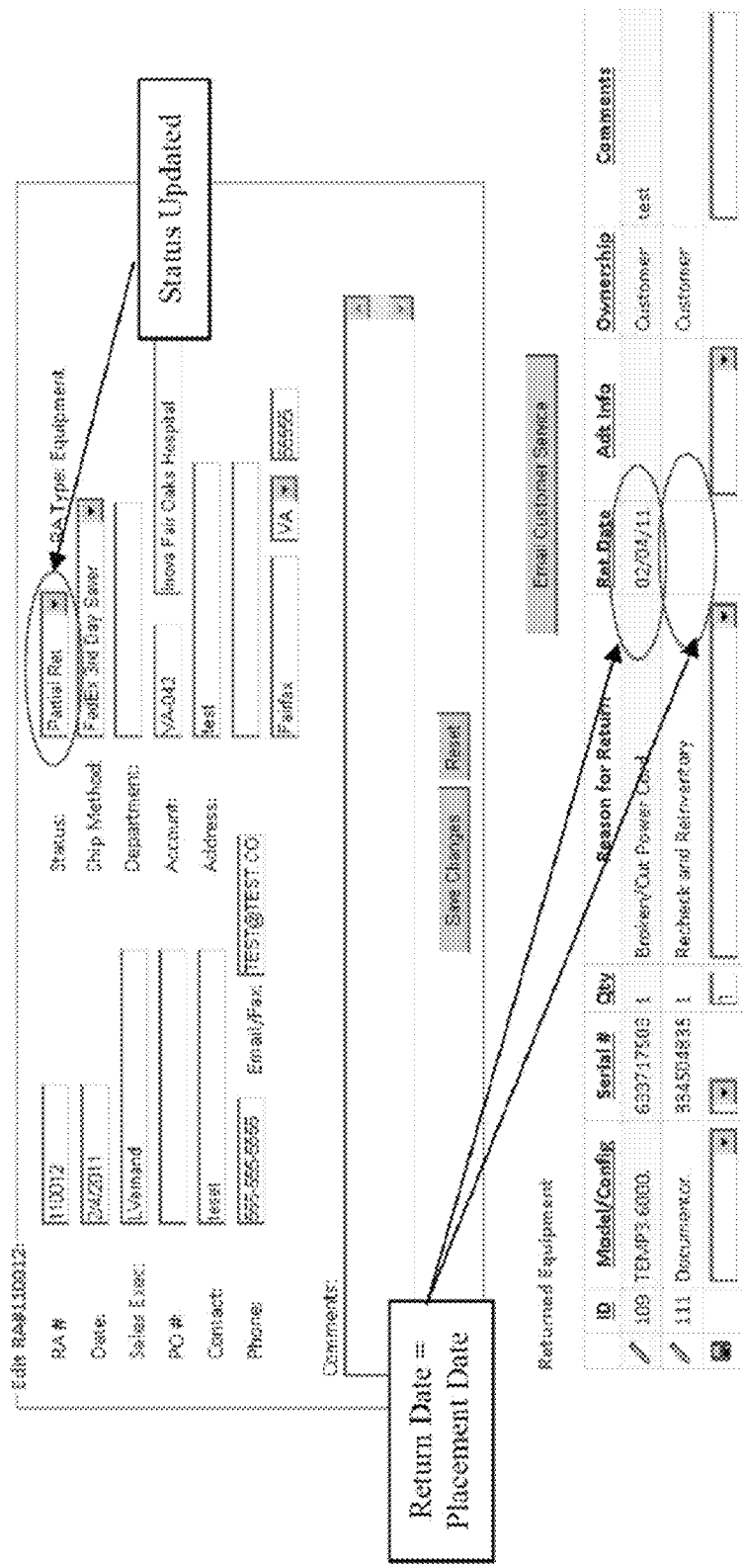
FIG. 67 is a schematic illustration of an example graphical user interface screen showing automated RA status updates.

3. The Returned Equipment Table is updated with the "Return Date" filled in. The Return Date is the same as the Placement Date. (See FIG. 67—RA Status Updates).

4. When both pieces of equipment are returned, the status changes to Closed automatically.

5. If Stands/Accessories are part of the Returned items, they do not affect the status of the RA. Changes to handling procedures mean this information is not updated as being returned, but is noted on the RA for advanced notification to the Receiving Department.

6. Equipment can be "Returned" to Stock, Maintenance, Quarantine and Testing Placement Types. If Equipment to be returned under an RA moves from the "returning location" to any other placement type than Stock, Maintenance, Quarantine or Testing, the Shipping and QA Department will be sent a notification e-mail by the application.

If Replacement Equipment is "TEMPORARY" versus Permanent, the Status of the RA will update to "Pending" upon receipt of the returned equipment. The Returned equipment will be handled according to the requirements associated with the "Reason for Return". Temporary Replacement equipment is generally always associated with a Complaint. The Shipping Department will be notified via e-mail (automatically generated) when the Equipment moves from Maintenance to Stock.

The Quality Assurance Department (or the Shipping Department, upon coordination with the Quality Assurance Dept) manually "Close" the RA based on their assessment of the parameters required for closure. (See FIG. 68—Manual Update of RA Status). For example, the RA is not closed until the Temporary Replacement equipment is returned to Stock.

Drape RAs

RAs for Drapes are created from the Main Menu Bar, Quality, New RA. (See FIG. 69—Main Menu Bar Quality Menu Items). The following is an example session.

Figure 70:
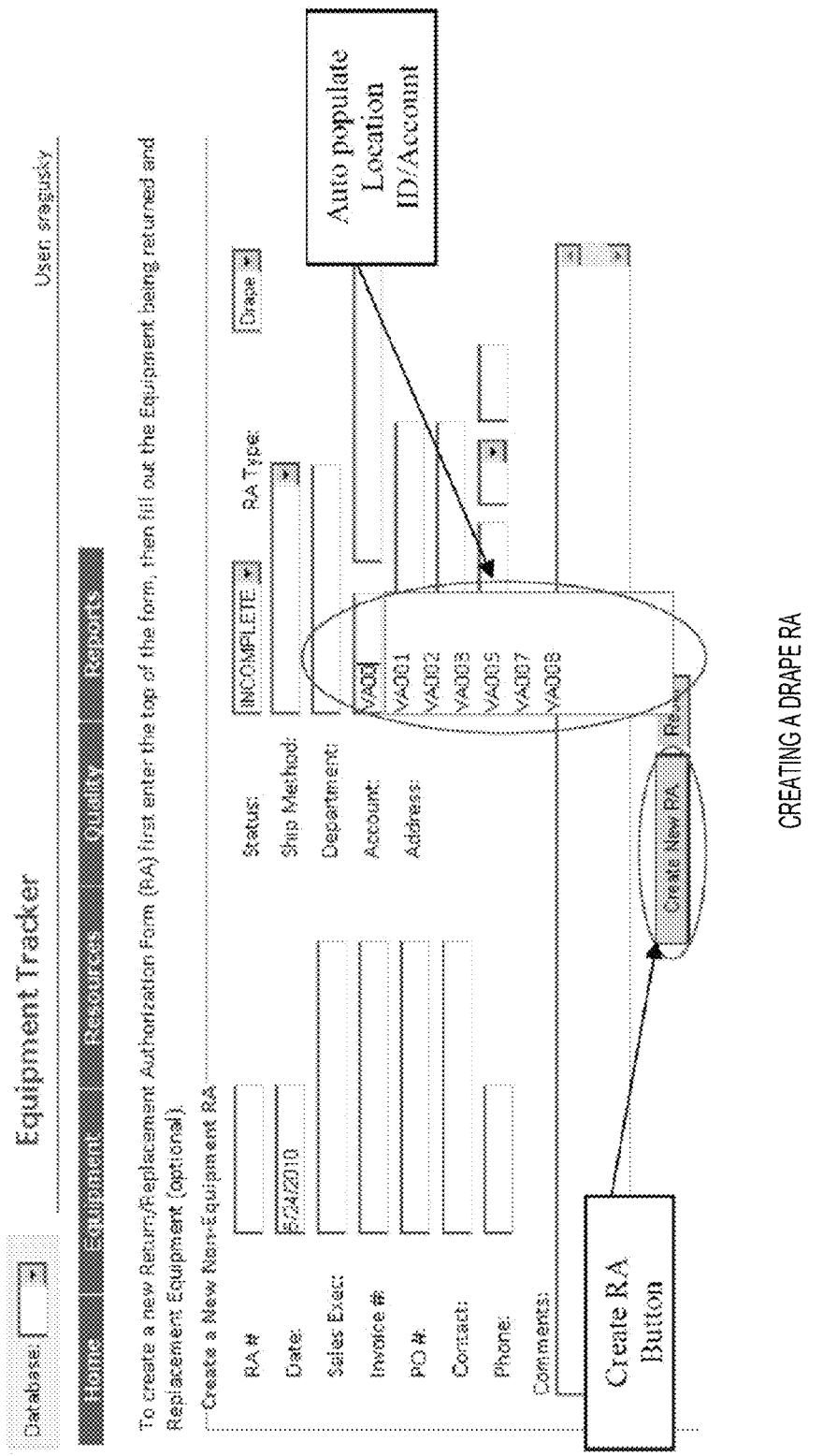
FIG. 70 is a schematic illustration of an example graphical user interface screen for creating a drape RA.
Figure 71:
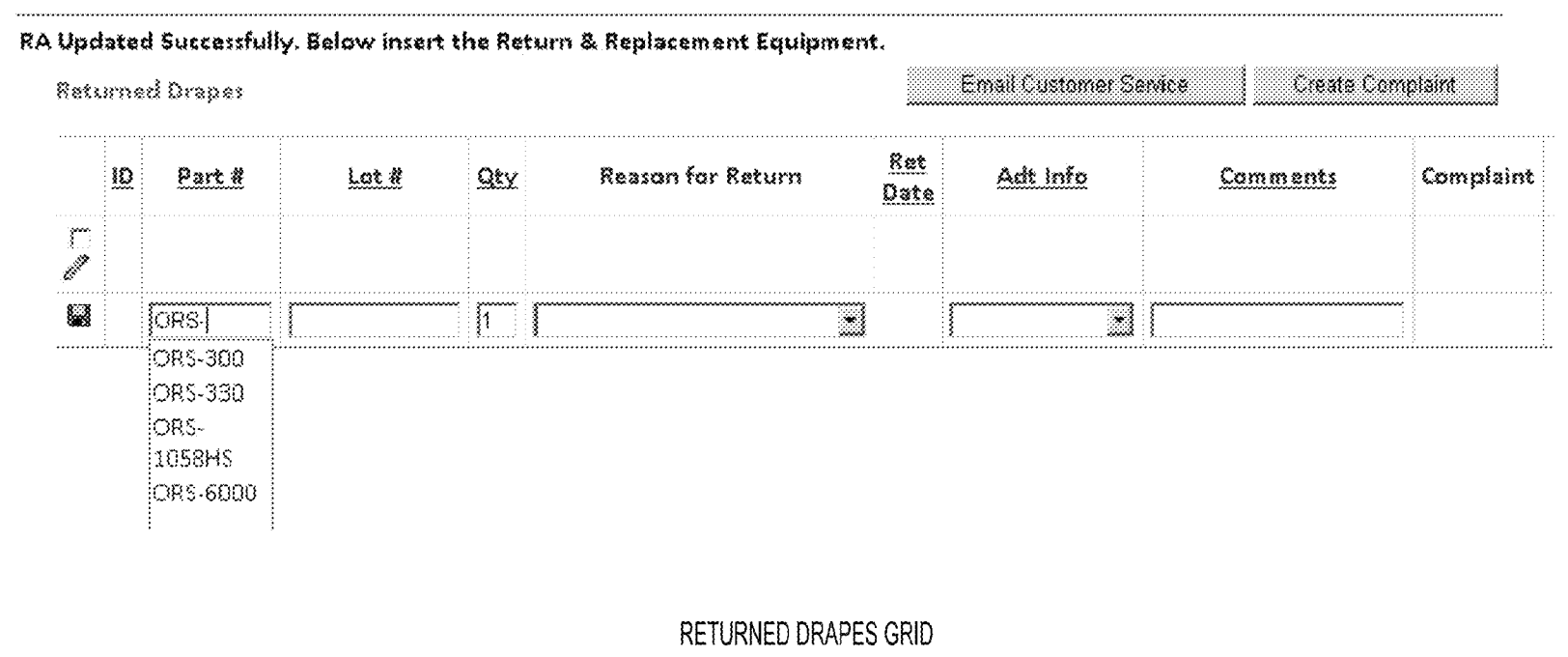

1. Select New RA.
2. The RA Page will display with the following defaults:
   a. Status=Incomplete.
   b. Type=Drape.
   c. Date=Date of Creation.
3. Enter Location ID/Account (select from auto populate menu) (See FIG. 70—Creating a Drape RA).
4. Location Name, Sales Executive (if applicable), City and State auto-fill.
5. Enter Contact Name and Phone Number (mandatory fields).
6. Enter Invoice Number and PO Number, if applicable.
7. Click "Create New RA Button".
8. Returned Drapes Grid displays. (See FIG. 71—Returned Drapes Grid).
9. Enter Product Number/select the product in the Part # field in the Returned Drapes Grid.
10. Enter Lot Number/select Lot in the Lot #field. Part # and Lot # are auto-populate fields based on what has been SOLD according to the accounting system.
11. Select a Reason from Return by clicking on the arrow in the field and selecting.
12. Add a Comment if applicable.
13. Click the Save icon to Save.
14. The RA Status will update from Incomplete to Active.
15. When the product is returned, search for the RA.
16. Click Edit Link to edit the RA.
17. Click the pencil icon and enter the Return Date for the item returned.
18. Status will change from Active to Closed.

Parts RAs

RAs for Parts functions in the same manner as Drape RAs. Parts RAs are used for Parts, and can also be used for Equipment where the serial number is not clear or available, or when the returning location states they have a product that is not documented as being in that location by the system. The following is an example session.

Figure 72A:
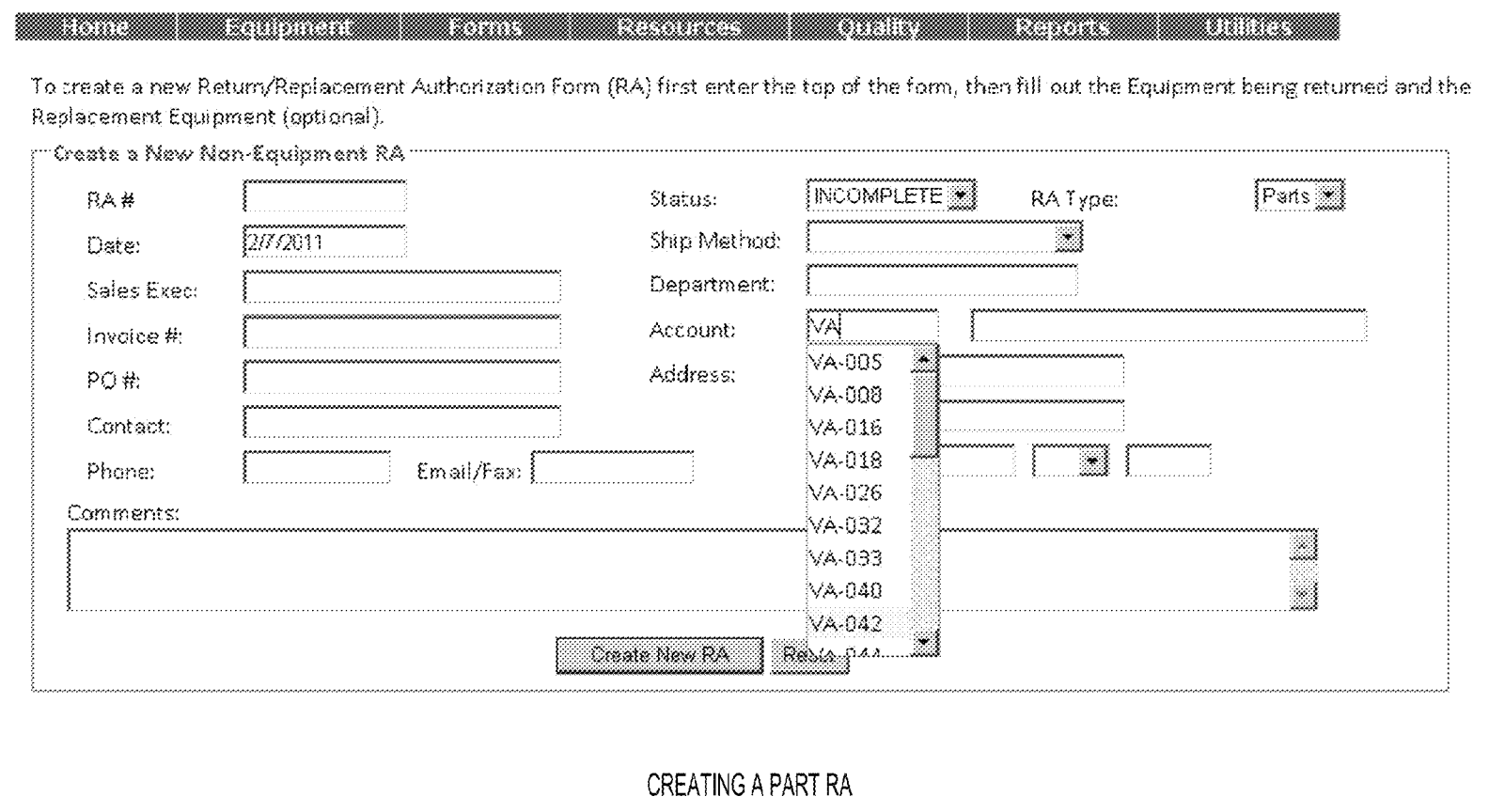

1. Select New RA from the Main Menu Quality Bar (e.g., See FIG. 69—Main Menu Bar Quality Menu Items).
2. The RA Page will display with the following defaults:
   d. Status=Incomplete
   e. Type=Part
   f. Date=Date of Creation
3. Enter Location ID/Account (select from auto populate menu) (See FIG. 72A—Creating a Part RA).
4. Location Name, Sales Executive (if applicable), City and State auto-fill.
5. Enter Contact Name and Phone Number (mandatory fields).
6. Enter Invoice Number and PO Number, if applicable.
7. Click "Create New RA Button".
8. Returned Parts Grid displays. (See FIG. 72B—. Return and Replacement Parts Grid).
9. Enter Part Number, enter "0" for Lot Number, and enter Reason for Return.
10. Click Save Icon to save.
11. Complete Replacement Equipment, if applicable.
12. Click Save Icon.
13. Click E-mail Customer Service to generate Packing List.
14. When Replacement Part is shipped, search for RA, and click Edit link.
15. Click Pencil Icon next to Replacement Part shipped, and add Sent Date.
16. When Returned Part is received, search for RA, and click Edit link.
17. Click Pencil Icon next to item returned and add Returned Date.
18. Click Save Icon.
19. RA Status will update from Active to Closed.

Using Parts RAs for Anomaly Equipment

There are situations where equipment needs to be returned, but there are issues associated. For example, the serial number label is illegible or the equipment is documented in the system as being at another location than stated by the RA requestor. Appropriate Reasons for Return are available to track metrics for these situations.

The Part RA is used to return the equipment to the main office, where QA takes responsibility for conducting an initial assessment. QA coordinates with the EqT Admin to update the equipment's placement and make appropriate notes. In the case of equipment being "mis-located" in the system, EqT Admin should note that the equipment was not located as the system indicated and update the placement to QA. Appropriate judgment is required to resolve anomaly equipment issues. QA must generate a new RA to move the equipment from QA to MFG and take whatever appropriate corrective actions are required for disposition of the equipment.

Multiple Returned Items with Complaints

In the event multiple pieces of equipment will be returned from a single location (e.g. a Sales Executives Inventory) and have associated Complaints, the QA Writer should initiate the process from the RA form rather than the Complaint. This is due to an RA being able to accommodate multiple items, but Complaints, by definition, are for single pieces of equipment. To do this:

1. Create the RA by going to the location and selecting the equipment and clicking the Create RA button.
2. Click on check box for specific equipment and select Create Complaint.
3. Edit the Complaint as appropriate and complete all required fields.
4. Repeat for all equipment requiring a Complaint. Replacement equipment can not be assigned in this circumstance.

Search RAs

Figure 69:
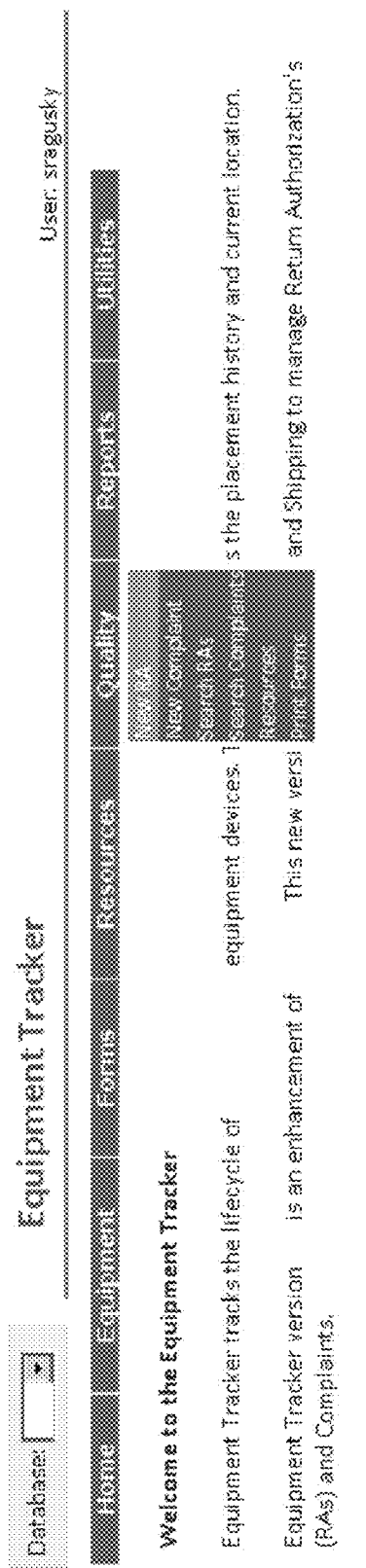
FIG. 69 is a schematic illustration of an example graphical user interface screen for the Quality Menu Items.

The Search RAs function is found on the Main Menu Bar, Quality, Search RAs (See FIG. 69—Main Menu Bar Quality Menu Items). The following is an example session.

Figure 73:
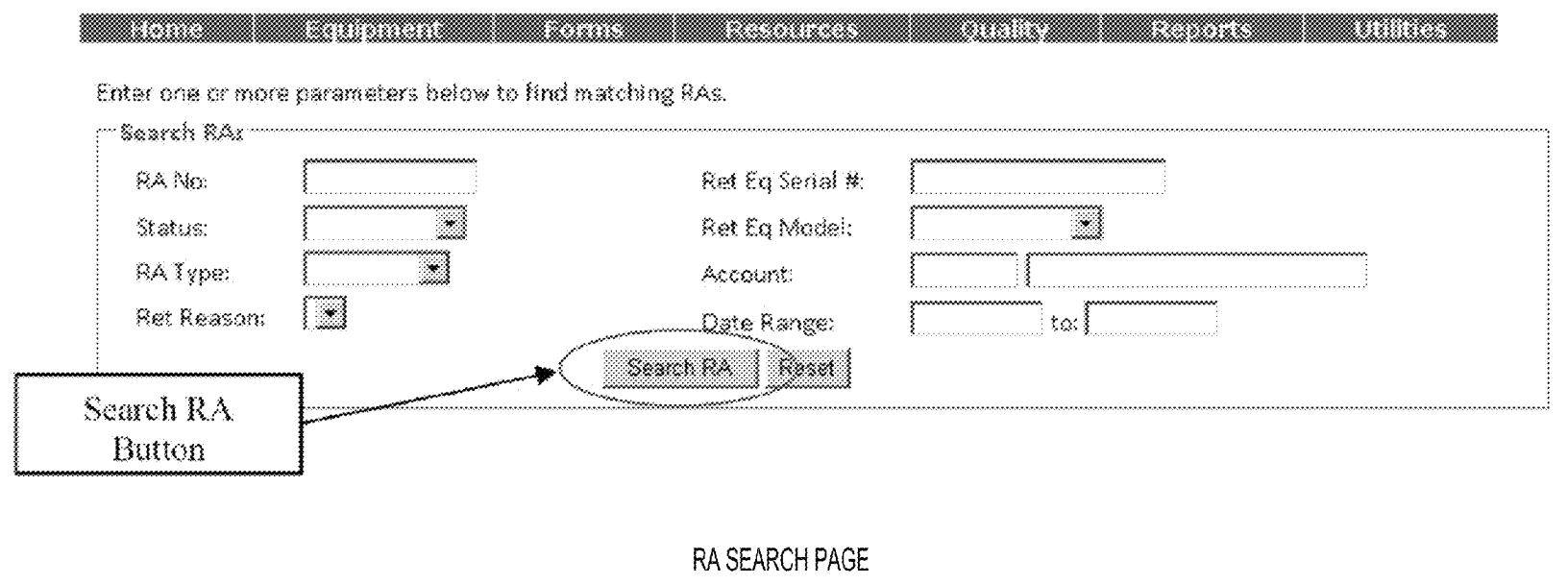
Figure 74:
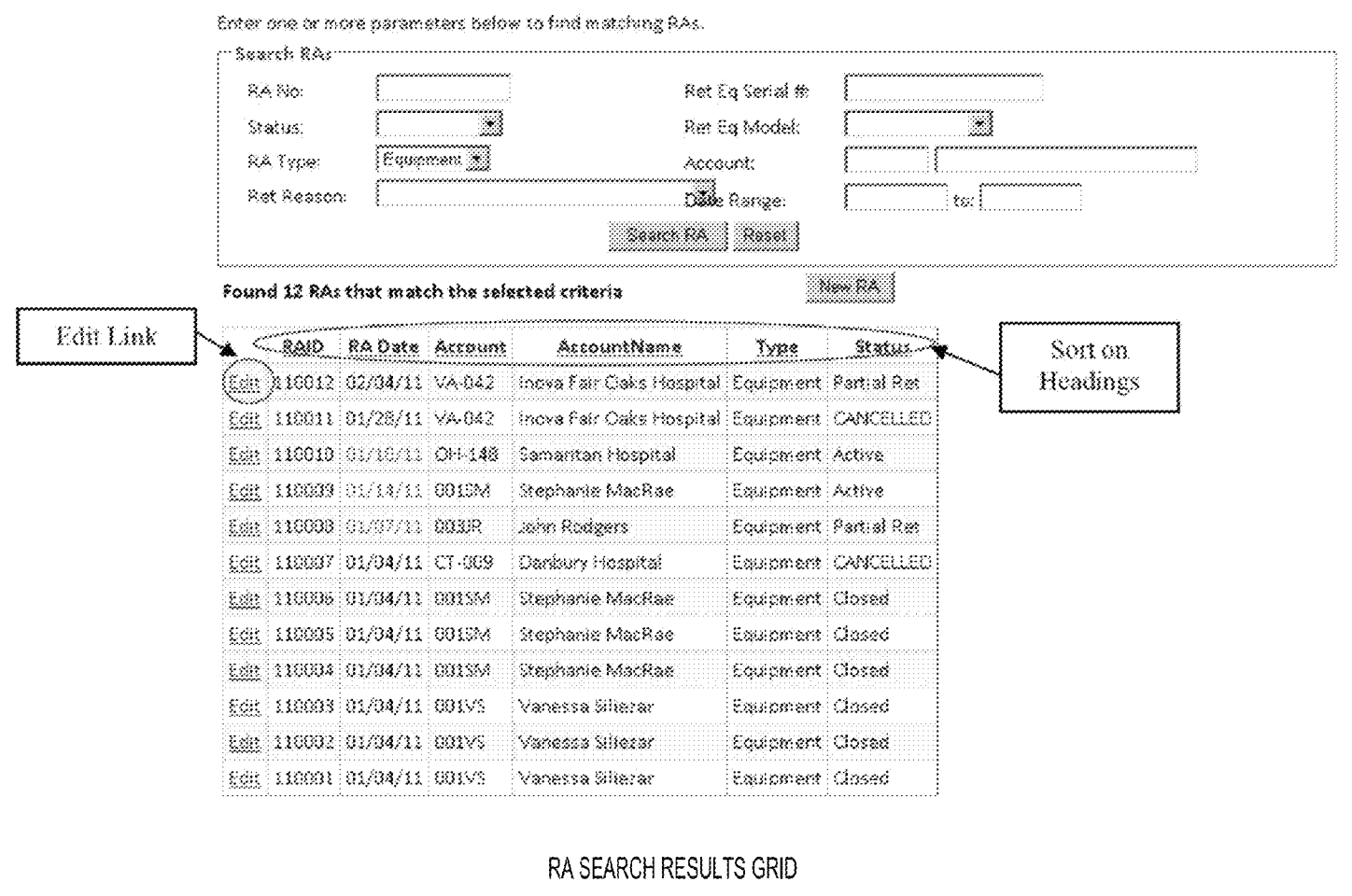
Figure 75:
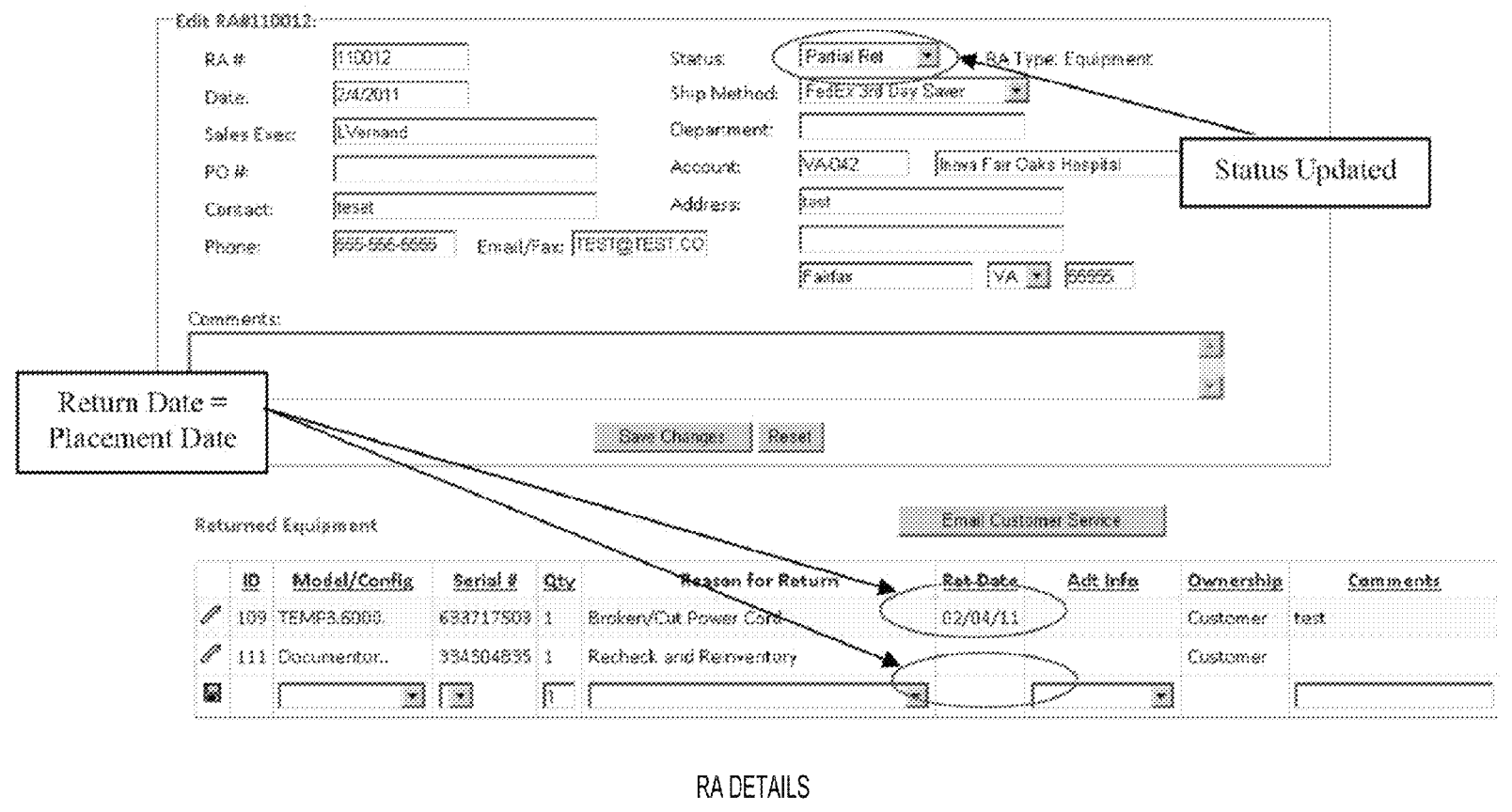

1. Select Search RAs from Main Menu, Quality. The Search Page will display. (See FIG. 73—RA Search Page).
2. Enter information on which to Search for RAs. Please be sure not to enter conflicting information.
3. RAs can be searched on the fields listed in FIG. 73—RA Search Page. Reasons for Return can only be queried once RA Type is selected.
4. The Search Results Grid will display. (See FIG. 74—RA Search Results Grid).
5. Click on the Edit Link to enter an individual RA.
6. The Search Results Grid can be sorted by clicking on the column headers. Click one for ascending and again for descending sorts based on the column header selected. RAs are color coded. For example, RAs color coded ORANGE have a Status of "Active" or "Partial Return" and are older than 14 days. RAs color coded BLUE are older than 14 days and have a Pending Status.
7. The Search Results Grid can be copied and pasted into an excel spreadsheet or word document.
8. Click on the Edit Link to enter an individual RA (e.g., See FIG. 75—RA Details).
9. The RA automatically updates as EqT Admin or Writer notes the movement of equipment. For example, equipment associated with an RA is returned to Stock. The new Placement Date is automatically logged into the RA as the Return Date. The status is updated to Partial Return or Closed depending on some or all of the equipment associated with the RA being returned.
10. Stands being returned are documented in a separate table under the Returned Equipment (e.g., See FIG. 76—Accessories Returns). Return dates are not captured for stands/accessories as part of new equipment handling procedures.

Complaints

Figure 77:
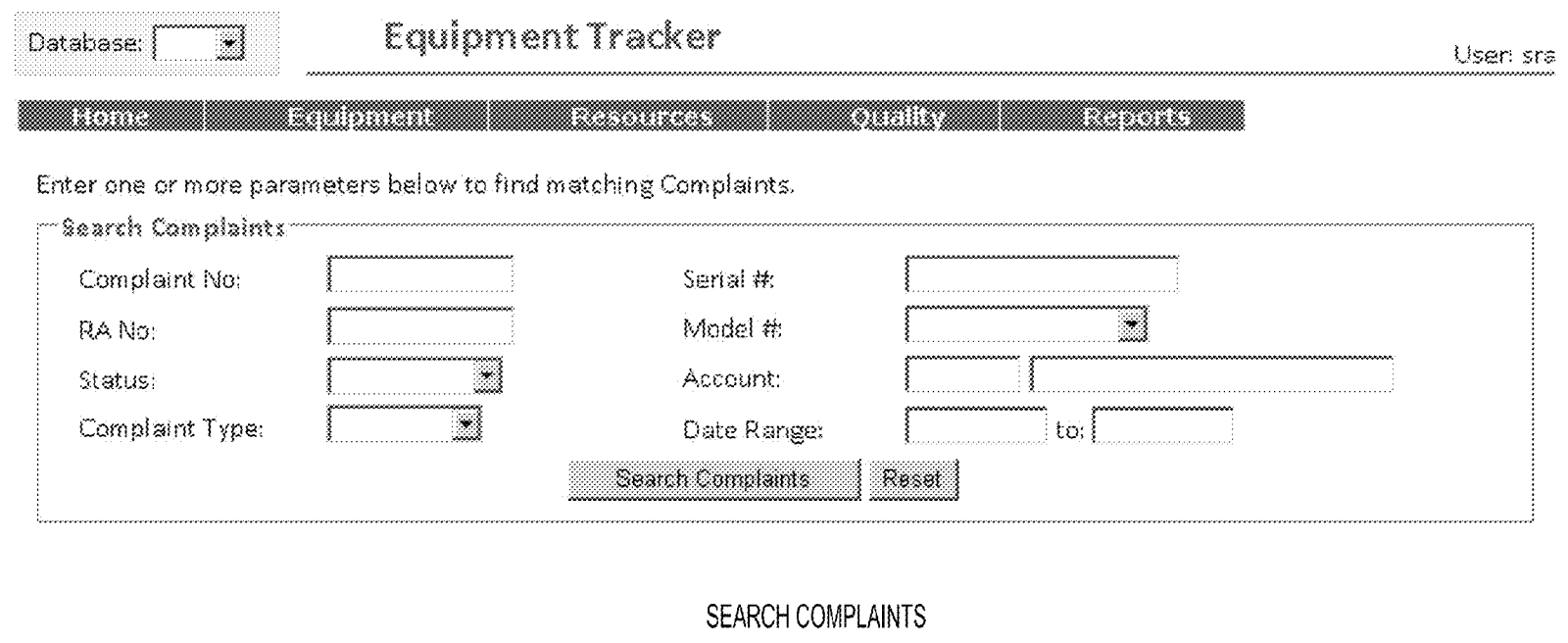
Figure 78:
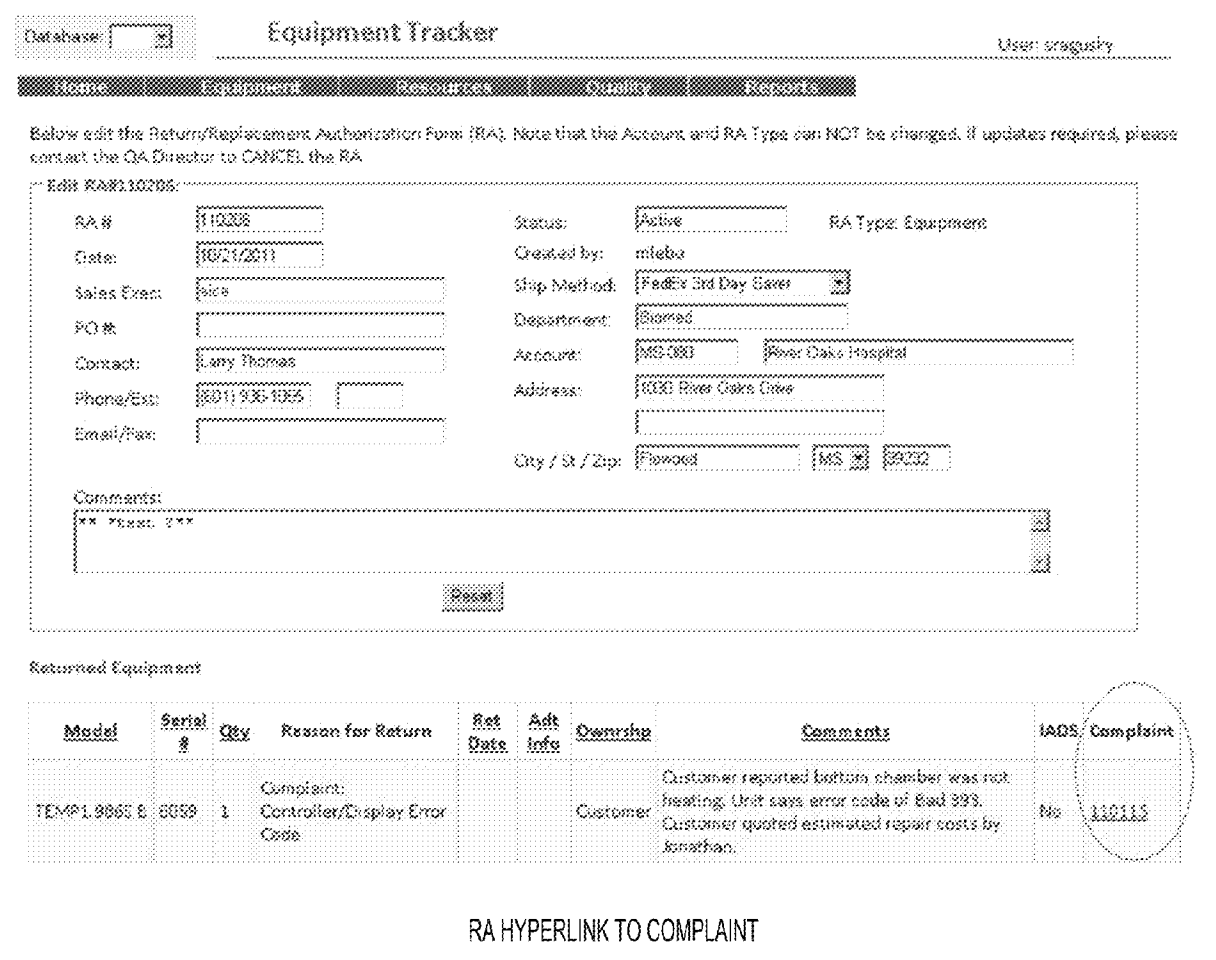

QA Users can review Complaints but can not change or create Complaints. Search Complaints is available from the Main Menu Bar under Quality. The search feature functions identically to the Search RA feature described above (e.g., See FIG. 77—Search Complaints). Complaints can also be accessed from the hyperlink in an associated RA (e.g., See FIG. 78—RA Hyperlink to Complaint).

Creating Complaints

Both QA Director and QA Writer can create Complaints, but fields related to the processing of Complaints are restricted to the QA Director. Complaints are either Internal (identified by someone employed by the Company) or External (identified by someone outside of the Company). The majority of Complaints are External.

Complaints from Main Menu Bar—Drapes and Parts

To create a Drape Complaint go to the Main Menu Bar, Quality, New Complaint. This method should be used for Complaints for Drapes or Parts. The following is an example session.

Figure 79:
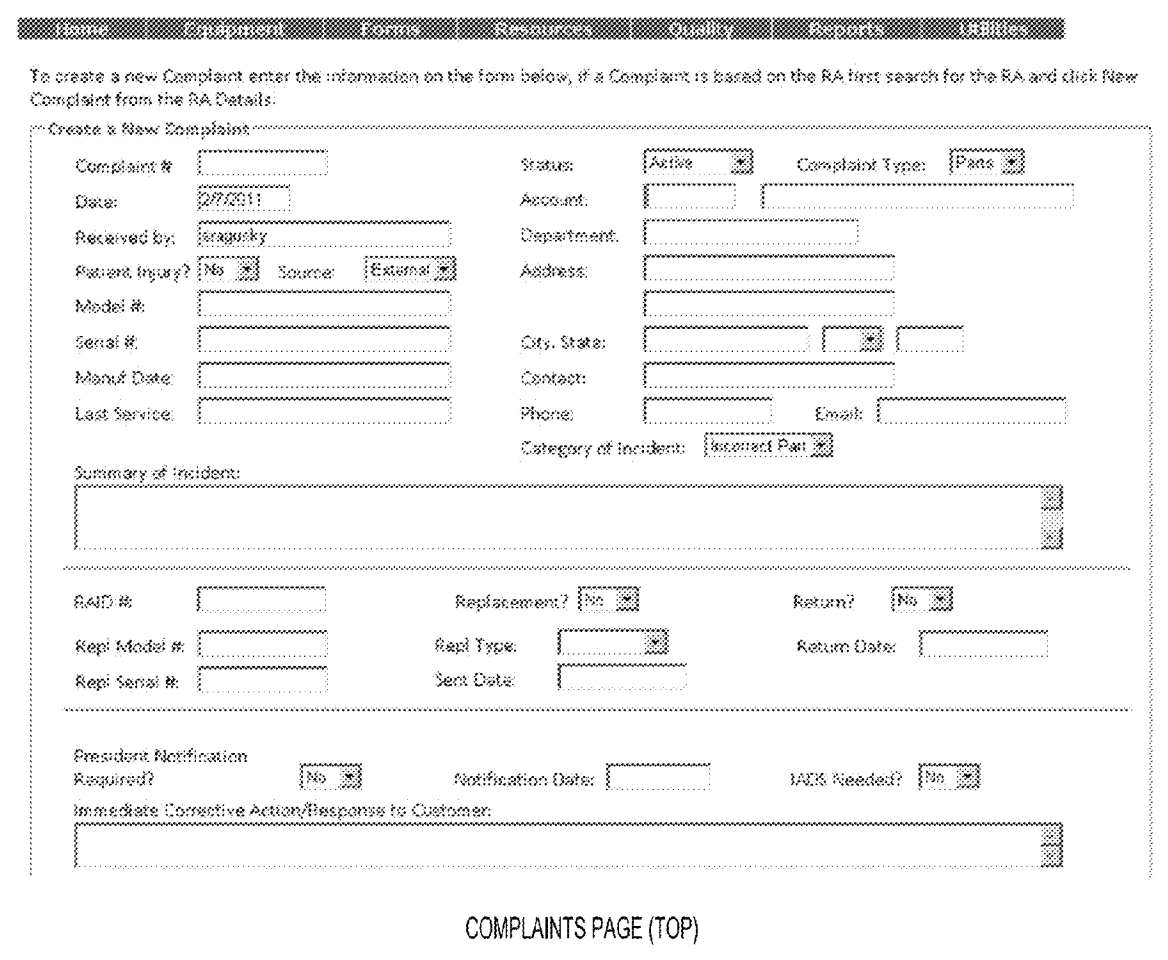

1. The Create Complaints Page will display. (See FIG. 79—Complaint Page (Top)).

2. Received by is populated with the User ID of the individual creating the Complaint. Default values are:
   Status=Active.
   Complaint Source=External.
   Complaint Type=Drape or Part.
   Date=Record creation date.
   Patient Injury=No.
   Replacement=No (refers to any Replacement Equipment that might be sent as part of the Immediate Corrective Action).
   Return=No (refers to Equipment being returned).
   IADS=No.
   Complaint Justified=No.
   Presidential Notification=No.
   CAPA=No.

3. Complete Model (or Product), Contact and Phone Number and select Account Number from Auto-populate list (Mandatory fields).

4. Account Name, City and State auto-fill.

5. Select Category of Incident.

6. Add details to Summary of Incident to describe complaint.

7. Fill in Immediate Corrective Action, if applicable.

Figure 80:
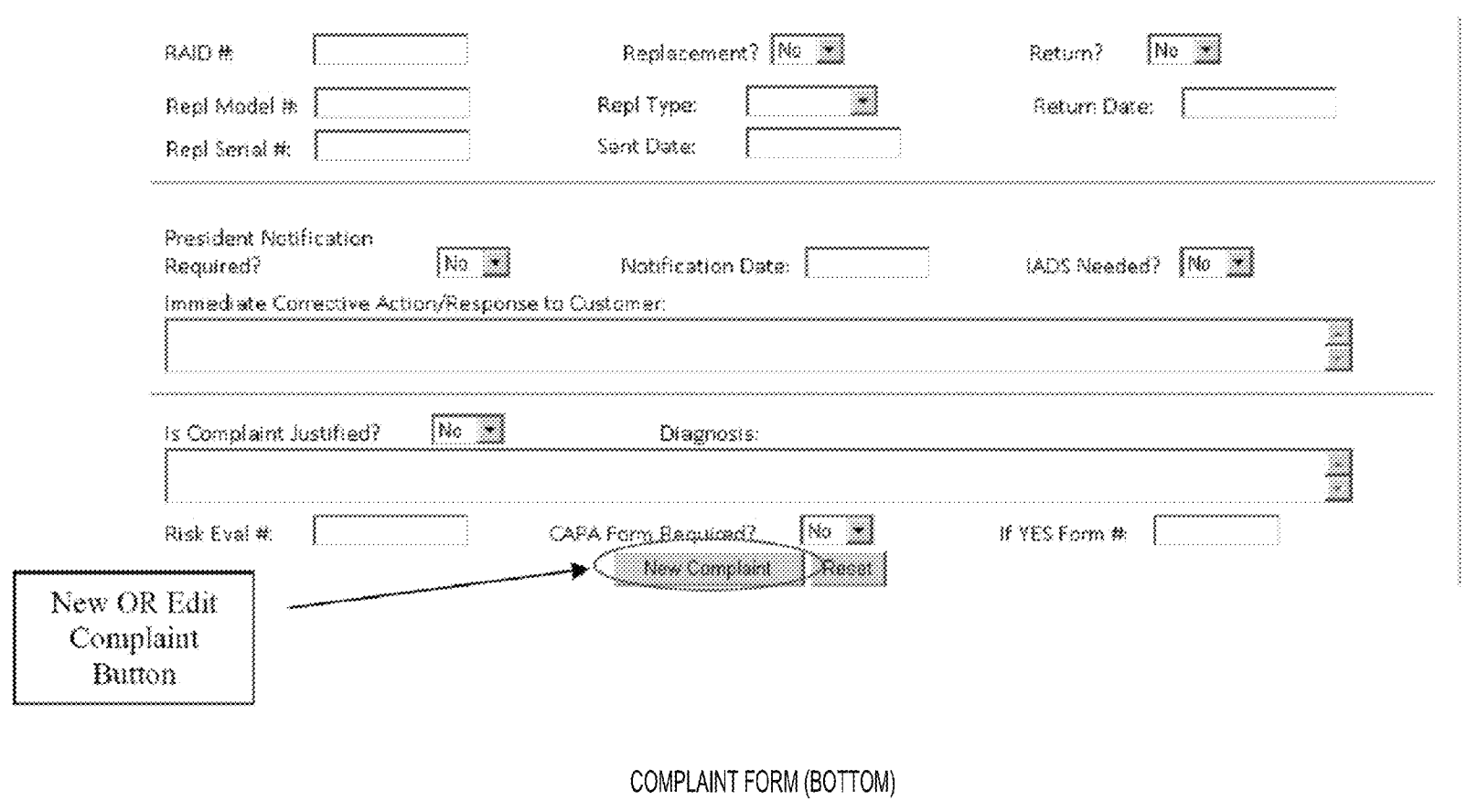

8. Click on "New Complaint" Button. (See FIG. 80—Complaint Form (Bottom)).

9. Complaint Number Auto-fills.

10. The QA Director is responsible for completing the remaining open fields of the Complaint as appropriate.

11. Provide rationale for Complaint Justification.

12. Update defaults as appropriate.

13. Enter Risk Eval Number and CAPA Form Number if applicable.

14. Update Status from Active to Closed.

15. Click on "Edit Complaint" button.

Create Complaint—Equipment

Complaints are typically for ONE piece of Equipment or Product. Only one Complaint can typically be open for a piece of equipment. The following is an example session.

1. Conduct Equipment Search for the Complaint Equipment.

2. Click Check Box for Complaint and Equipment.

Figure 81:
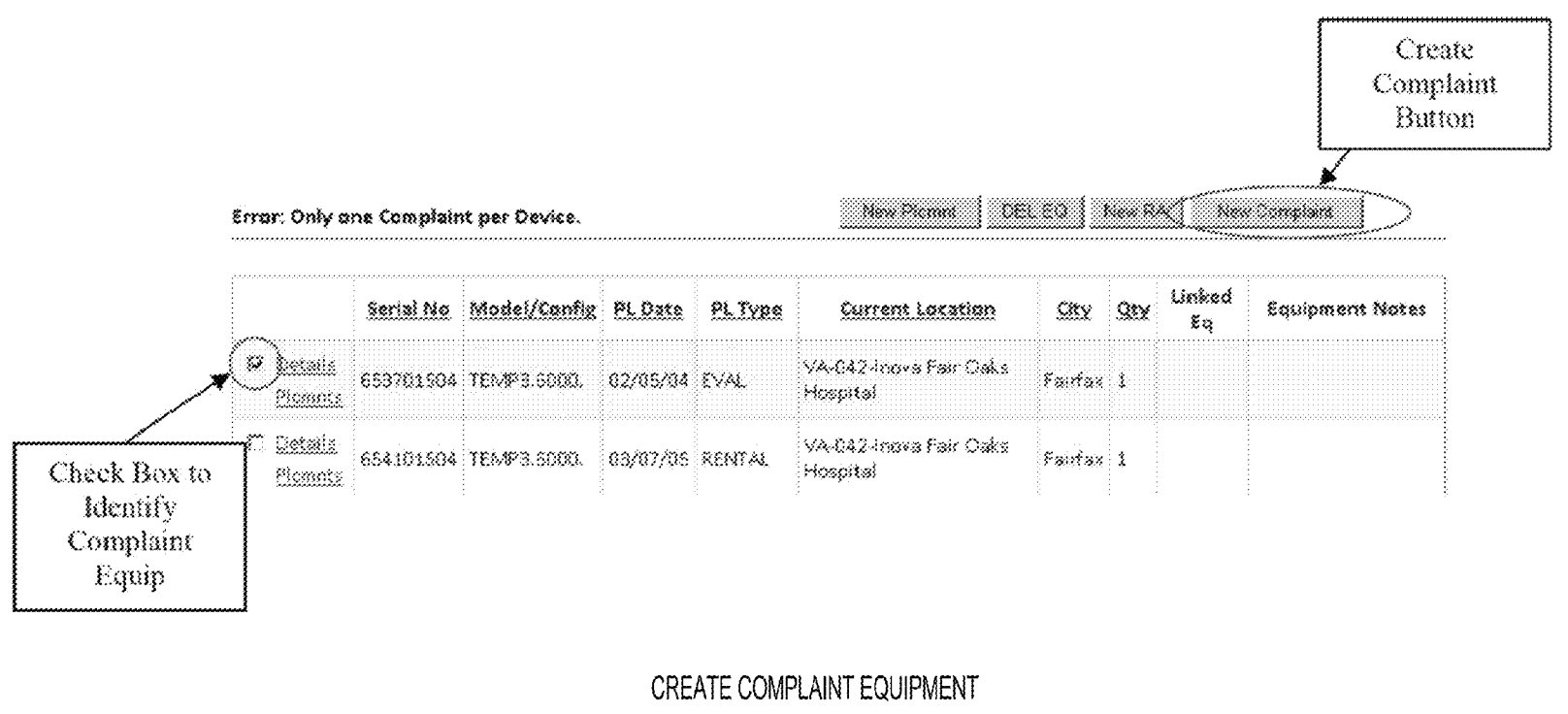

3. Click on "Create Complaint" button. See FIG. 81—Create Complaint Equipment.

Figure 82:
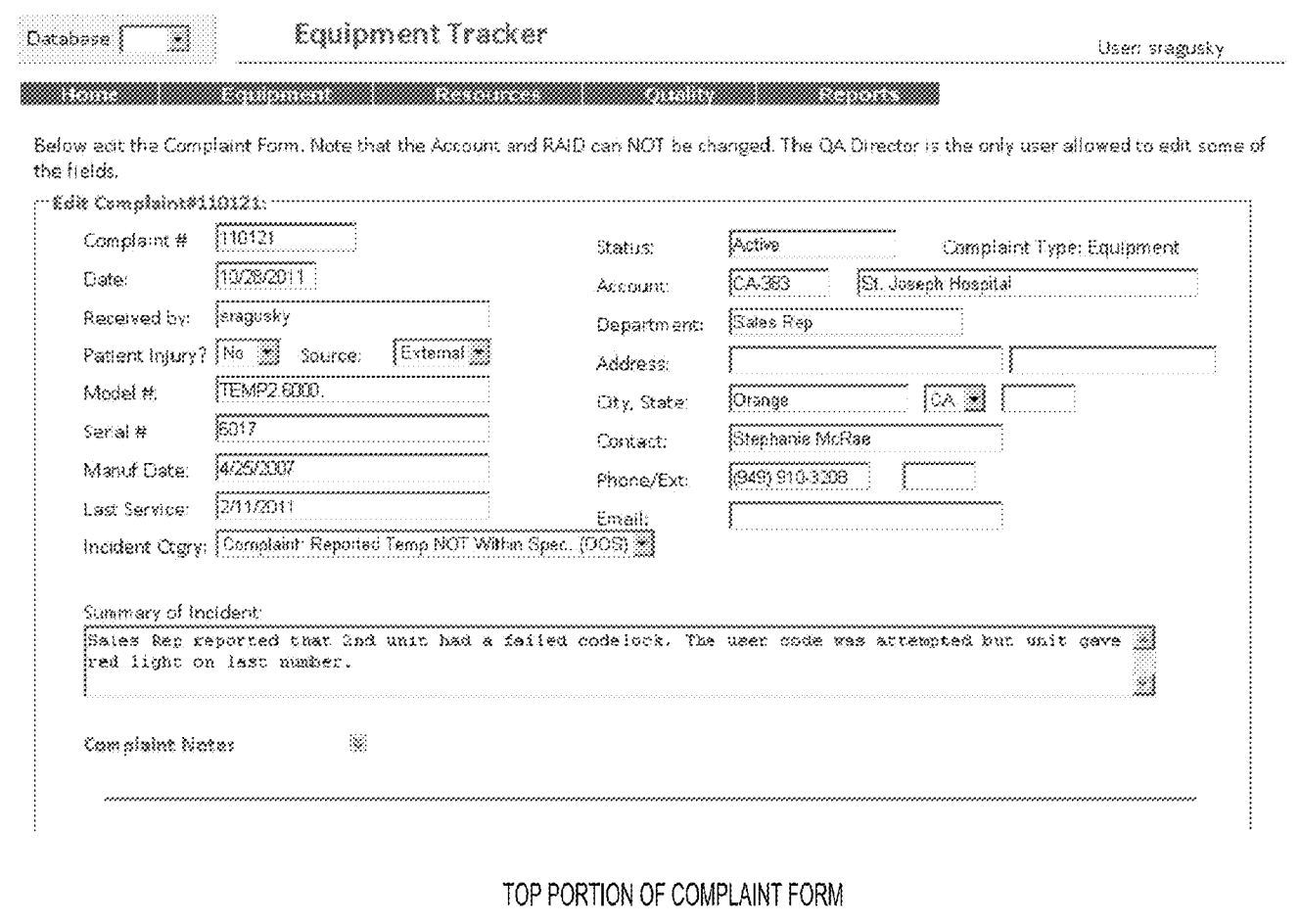

4. Complaint Window (See FIG. 82—Complaint—Top Half) displays with information auto-filled and Complaint Number assigned. Defaults are identical to the Drapes and Parts Complaints described above.
   Model Number and Serial Number, Account Number, City and State populate based on the Equipment Search selection.
   "Manuf Date" is auto-filled based on information on the initial Placement Date of the Equipment.
   "Last Service" is auto-filled based on the last date with a Maintenance Placement Type.

5. Complete Contact and Phone Number (Mandatory Fields).

6. Selected Category of Incident (Mandatory Field).

7. Add information to Summary of Incident.

8. If as part of the Immediate Corrective Action Replacement Equipment will be sent, complete street address and Zip Code.

9. Change Replacement from "No" to "Yes".

10. Select Replacement Model.

11. Select Replacement Type (Permanent or Temporary). Temporary Replacement equipment is used when Customer owned equipment is being returned for the Complaint.

12. If the Complaint Equipment is being returned, change Return from "No" to "Yes".

Figure 83:
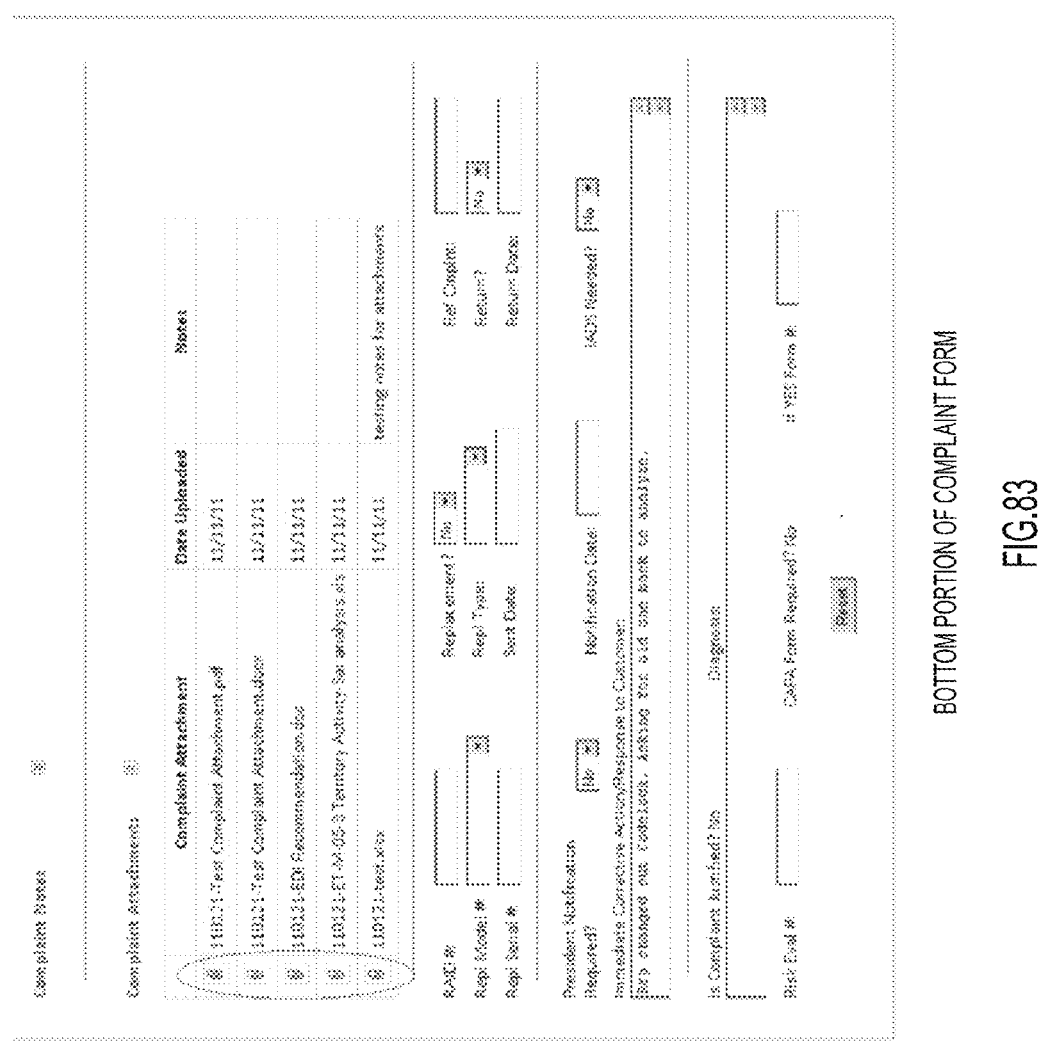

13. Click "Save Changes" button (See FIG. 83—Lower Half Complaint Record).

14. Click "Create RA" button.

15. RA Window will display with all information completed including Replacement Equipment.

16. Verify information is correct on the RA.

Figure 84:
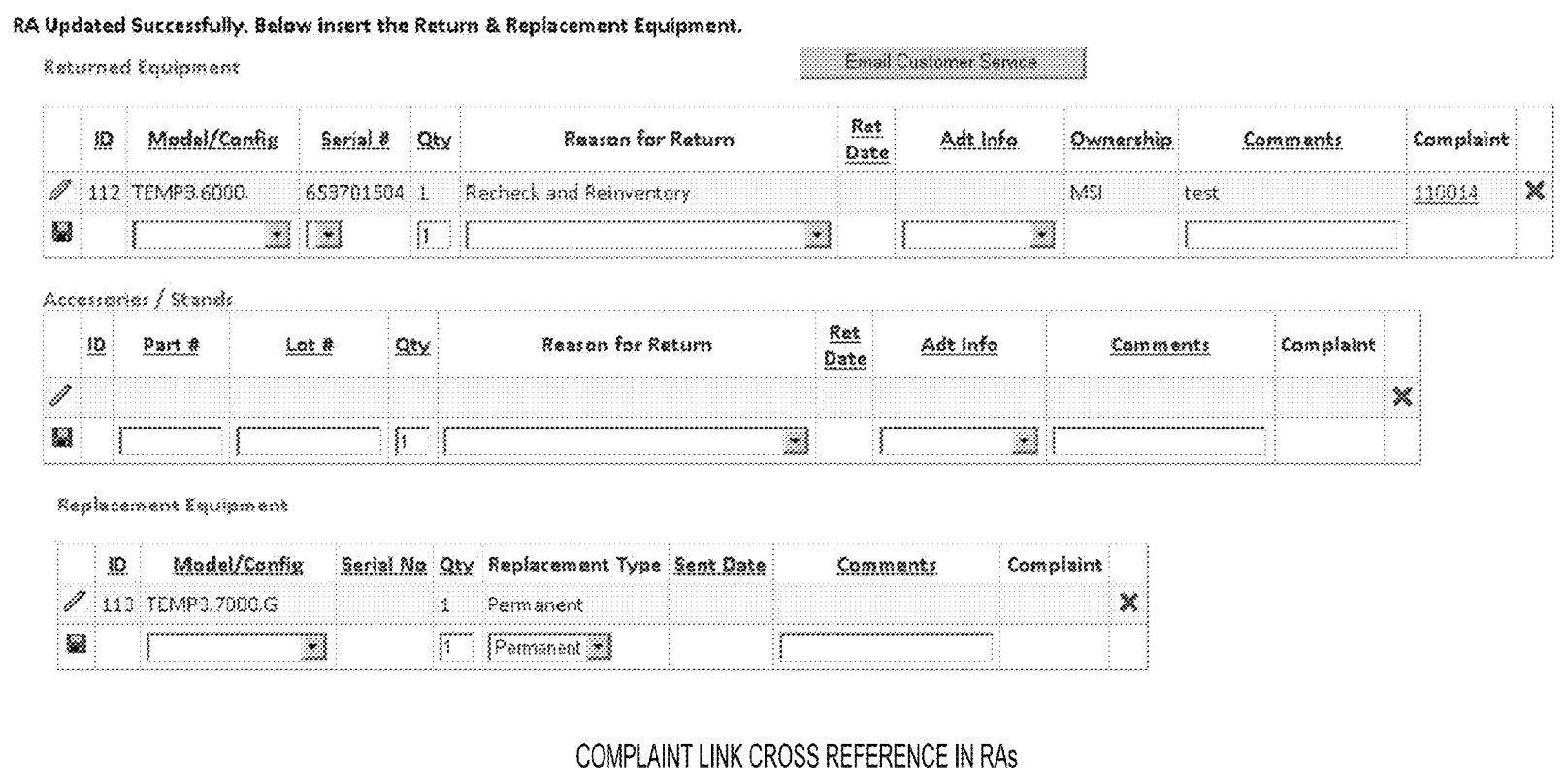

17. If Replacement Equipment is required click on the "Email Customer Service" Button (See FIG. 84—Complaint Link Cross Reference RAs). This will generate an e-mail with the RA information and the Replacement Equipment information allowing Customer Service to create the appropriate Packing Slips. Complaint Number is auto-populated in the Return Equipment Table and Replacement Equipment Table and functions as a LINK.

18. QA Director processes Complaint as described above.

If there is more than one Complaint from a location with no associated RA required, the QA Writer can use a "Copy Complaint" button. The system will prompt for an update to Model and Serial Number. If there are multiple Complaints with associated RAs the process should initiate with the RA as described above for multiple returned items.

Multiple Complaints from Single Location—Copy Complaint

In the event that a single location is filing multiple complaints and is not returning equipment, the "Copy Complaint" feature can be used. The following is an example session:

1. Complete initial Complaint.

2. Click on the "Copy Complaint" button. (e.g., See FIG. 85—Copy Complaint).

3. Identify the Type of Complaint. (e.g., See FIG. 86—Select Copy Complaint Type). This allows association of Drape and Equipment Complaints. When copying an Equipment Complaint and choosing Equipment, a list of the available models for the location will be displayed. Selecting a Model will present Serial Numbers available at the location.

Complaints are processed and signed off following QA procedures. There can be many documents created in addressing Complaints. These additional documents can be uploaded and attached to the Complaint Record in ET. Acceptable document format types may include:
   doc
   docx
   xls
   xlxs
   pdf The following example session represents attaching files/documents to a Complaint:

1. Search for the Complaint and open the record.

2. Click on the arrow for Complaint Attachments (e.g., See FIG. 87—Complaint Attachments Arrow).

3. The Complaint Attachments section of the Complaint will expand (e.g., See FIG. 88—Adding Complaint Attachments). Any existing Attachments will display in addition to the grid which allows for the addition of further documents is available. To hide the list/addition grid, click on the arrow.

4. To add a document, click on Browse and navigate to the file selected for uploading (e.g., See FIG. 89—Browsing to Complaint Attachment File).

5. Click Open.

6. File path will be displayed in Complaint Attachment Grid.

7. Add notes if appropriate and click on the Save icon to save the upload.

Figure 90:
FIG. 90 is a schematic illustration of an example graphical user interface screen for uploading complaint attachments.

8. The file will be added and the Date Uploaded populated (e.g., See FIG. 90—Attachment Uploaded).

9. Click on the Pencil Icon to edit notes. The file path and date can not be changed.

10. Repeat until all Complaint Attachments are uploaded. Attachments related to Complaints are stored within the Equipment Tracker Database and can be reviewed by clicking on the paper clip icon.

Search Complaints

Figure 91:
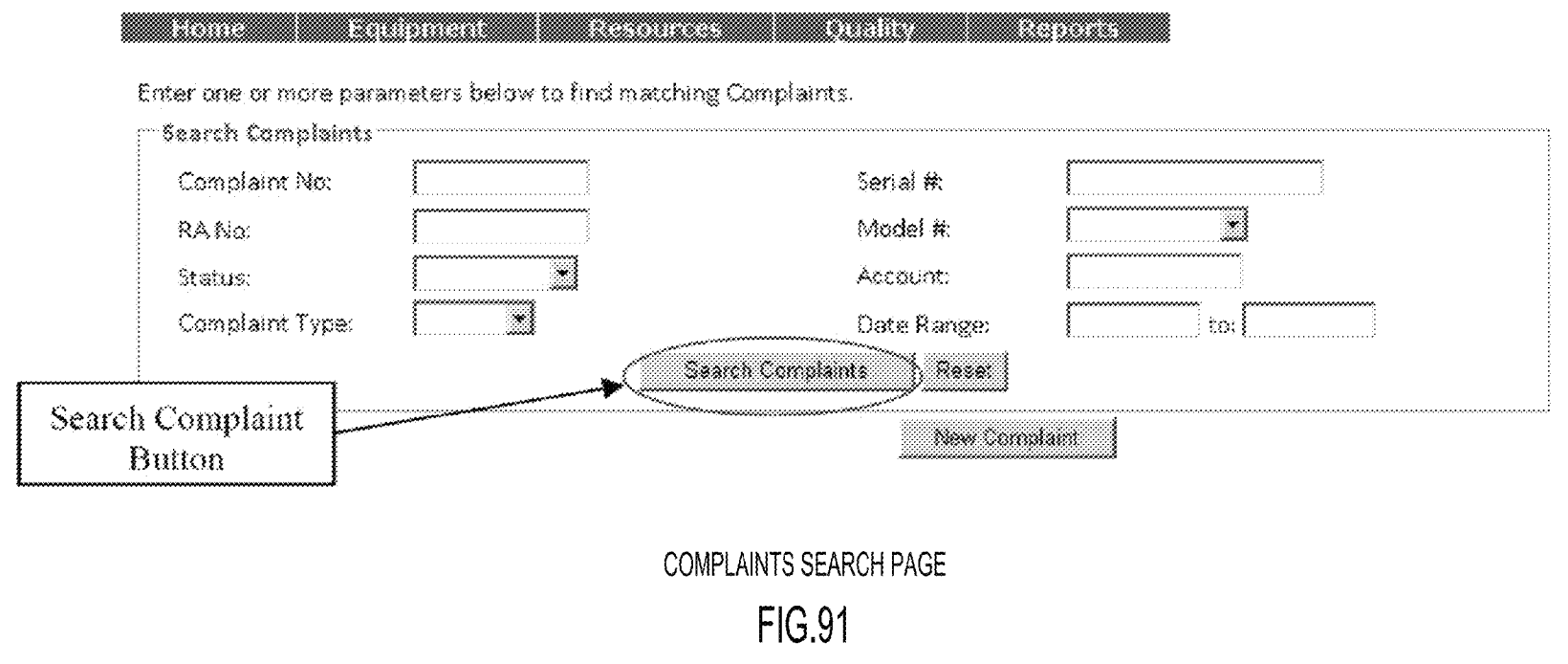

The Search Complaints function is found on the Main Menu Bar, Quality, Search Complaints (FIG. 91—Complaints Search Page displays the QA menu). The following is an example session.

1. Select Search Complaints from Main Menu, Quality. The Search Page displays.

2. Enter information on which to Search for Complaints. Please be sure not to enter conflicting information.

3. Complaints can be searched on the fields listed in FIG. 91—Complaints Search Page.

Figures 92, 93:
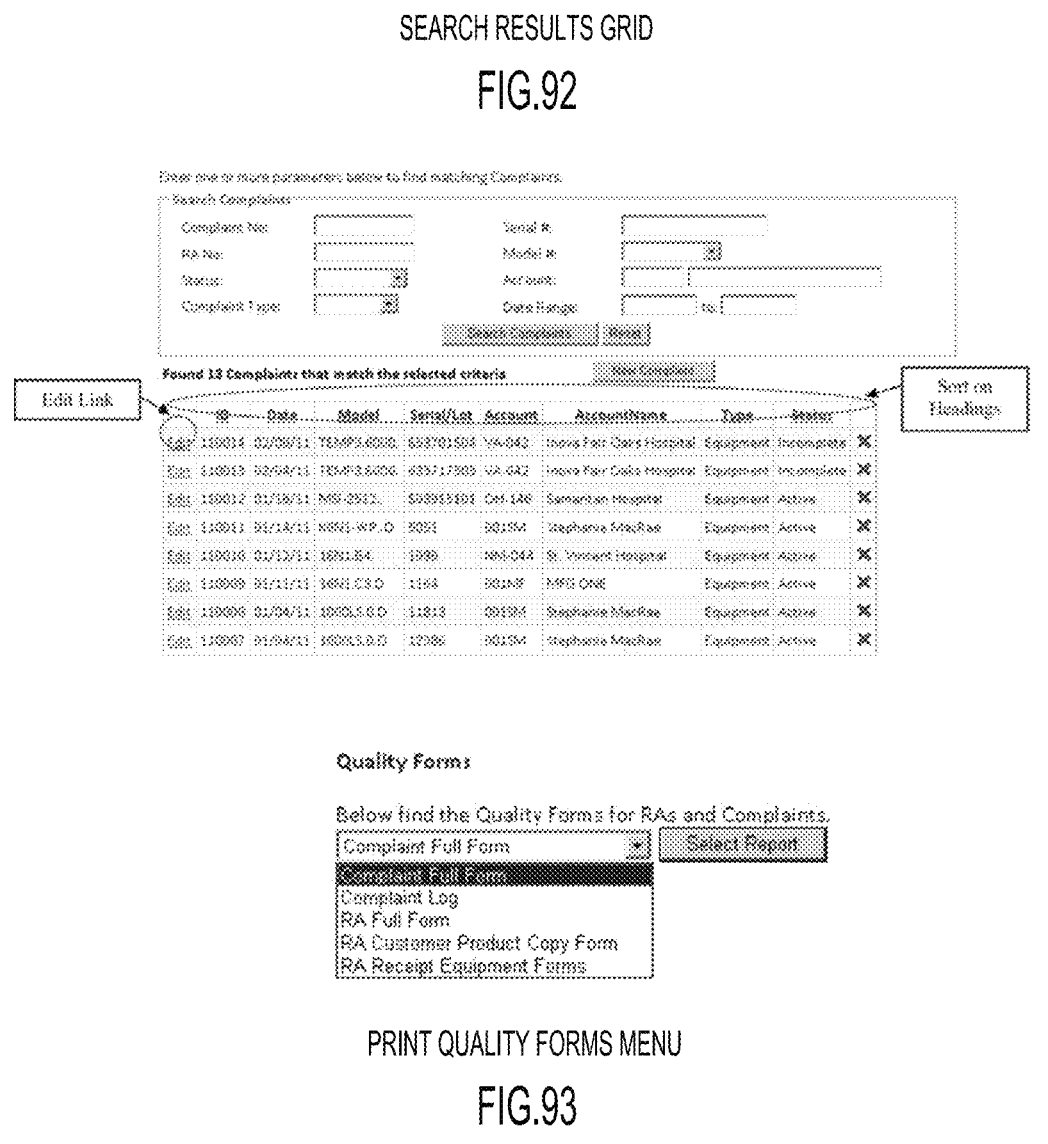

4. The Search Results Grid will display. See FIG. 92—Search Results Grid.

5. Click on the Edit Link to enter an individual Complaint.

6. The Search Results Grid can be sorted by clicking on the column headers. Click one for ascending and again for descending sorts based on the column header selected. Complaints are color coded. For example, complaints color coded ORANGE have a Status of "Active" and are older than 30 days.

7. The Search Results Grid can be copied and pasted into an EXCEL spreadsheet or WORD document.

8. The X is used to delete a Complaint (QA Director only).

Print Forms

The system provides the capability to print RA and Complaint Forms. This functionality provides Search capability to allow the user to print only those records of interest. The Shipping/Receiving Department currently relies on hardcopy forms. QA Users in the Shipping/Received Department will, based on Standard Operating Procedures, periodically print RA Forms. Future versions of ET will provide a capability to print the correct number of RA Forms based on the anticipated destination within the Company for Returned Equipment. The following is an example session to access Print Forms.

1. Main Menu Bar, Quality, Print Forms.

2. Select the Report Form desired. (See FIG. 93—Print Quality Forms Menu).

Figure 94:
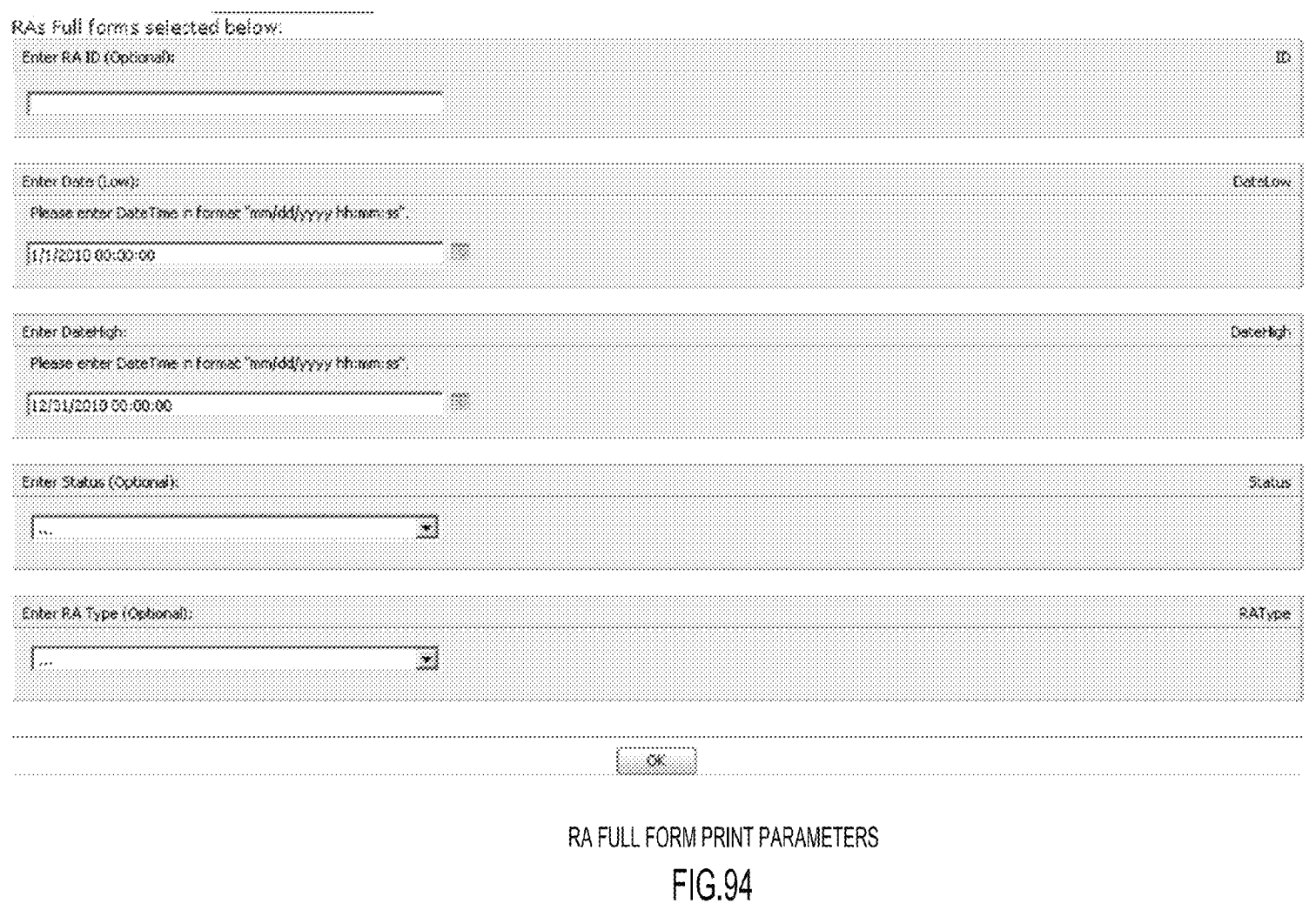

3. Fill in Search Criteria (See FIG. 94—RA Full Form Print Parameters).

4. Click Ok.

Figure 95:
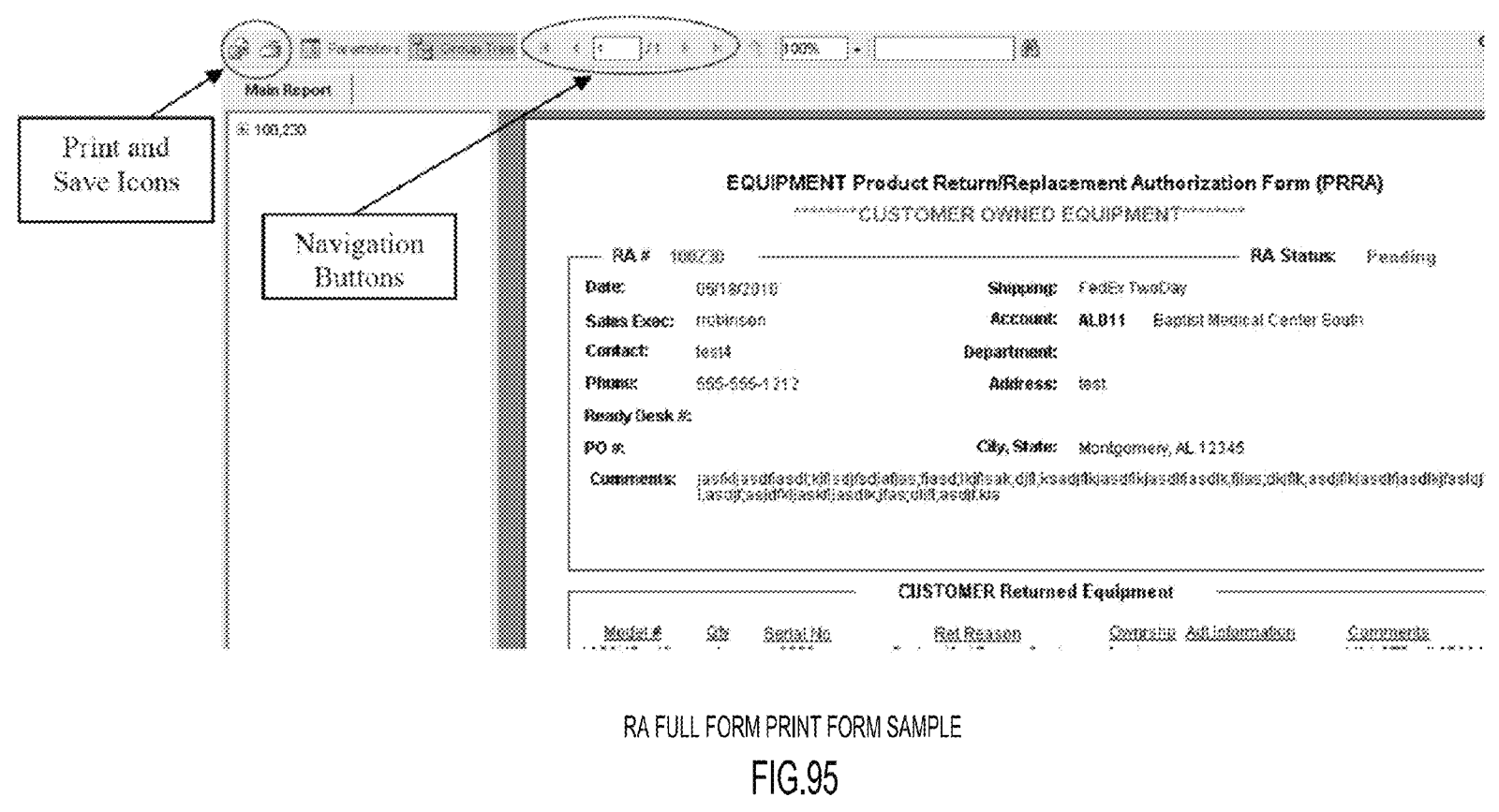

5. Report will display. (See FIG. 95—RA Full Form Print Form Sample).

6. Navigate thru pages of report (if applicable) using the Navigation Buttons.

7. Click the Save Icon to Save the report.

8. Click the Printer Icon to Print the report.

Figure 96:
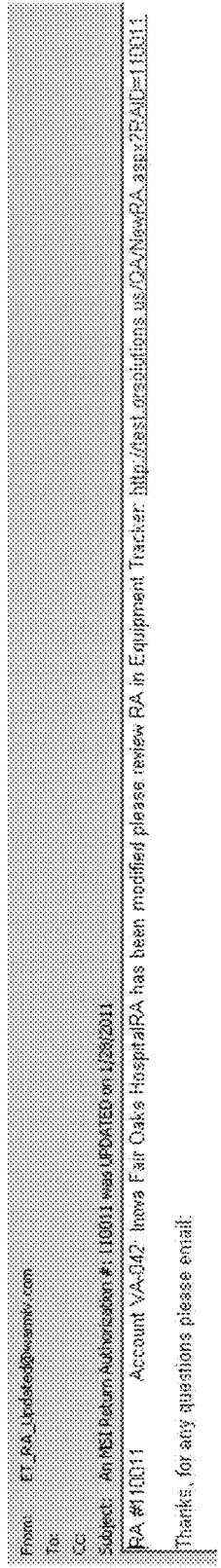
FIG. 96 is a schematic illustration of an example e-mail to shipping concerning an update to an RA.

The QA Department can update RAs with ship to address changes, adding equipment to the RA, and deleting equipment from the RA. In addition, status changes, including canceling the RA are also made. E-mails are automatically sent to the Shipping/Receiving Department when these RA updates are made (e.g., See FIGS. 96 and 97). The Shipping/Receiving Department may elect to print a replacement RA dependent on the nature of the RA Update. QA Department standard operating procedures are typically not to add either Return Equipment or Replacement Equipment to the RA after a 24 hour period. Any Replacement Equipment modification will be coordinated with Customer Service.

Printing Selected Complaints or RAs

Complaints and RAs can also be selected for Print from a Search Results Grid. Click the box to the left of the Complaint or RA number and then select "Print" (e.g., See FIG. 98—Print Selected Complaints or RAs).

Printing RA Receipt Forms and IADS

Equipment being returned as part of the Immediate Corrective Action for a Complaint may require an Initial Assessment Data Sheet (IADS). This requirement is identified by selected IADS="YES" when the QA Department Completes the Complaint record. Upon receipt of the Equipment, the Shipping/Receiving Department will print an RA Receipt Form. The IADS will automatically be printed when printing the RA Receipt Form. The Process to print an RA Receipt Form and its associated IADS (if applicable) is the same as identified above in Print Forms.

QA Resources

The QA Director has permission to Manage Reasons for Return. This provides flexibility and ensures appropriate categories for QA Department records and metrics are kept. The following is an example session to access Resources.

1. Main Menu, Quality, Click on Resources.

Figure 99:
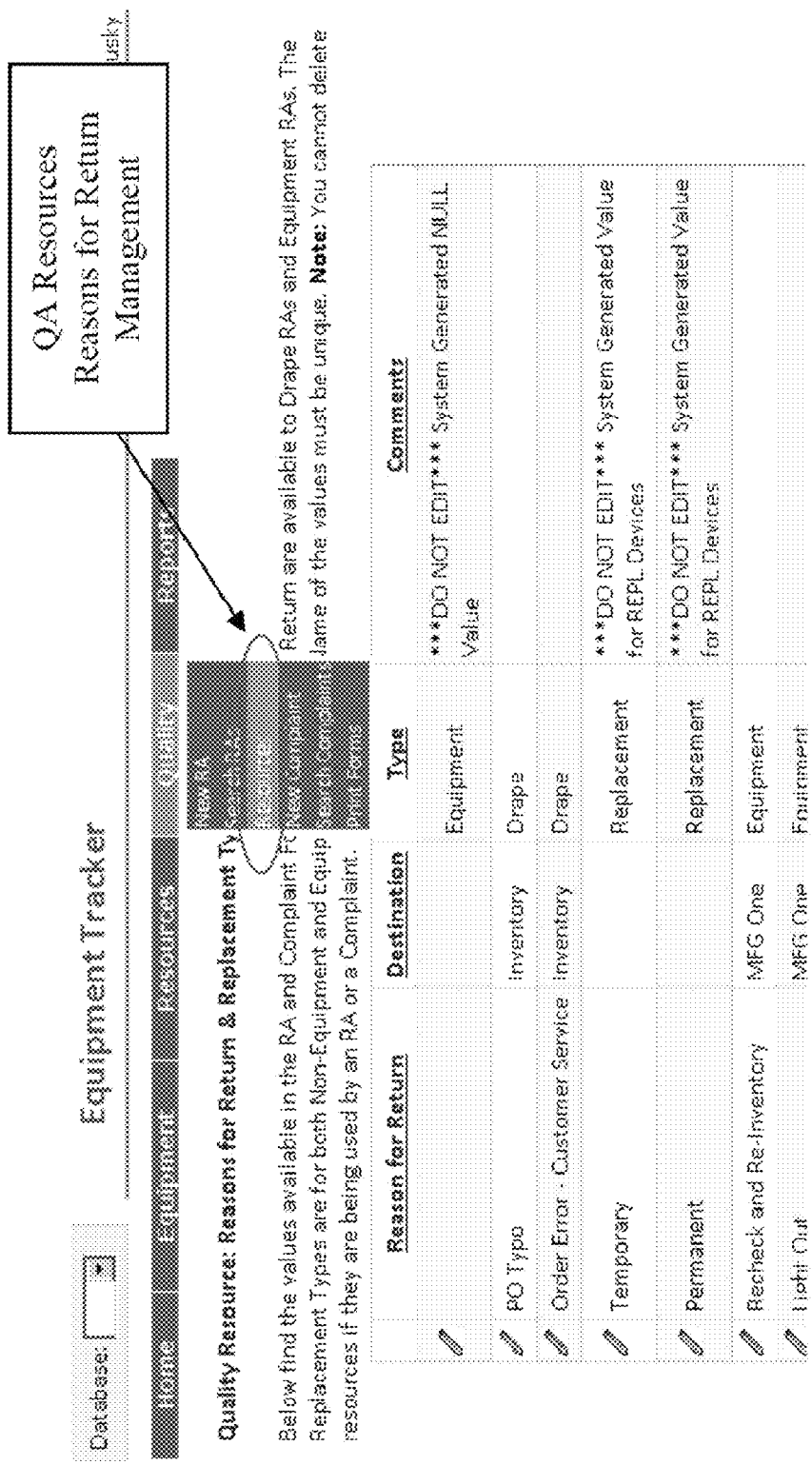
FIG. 99 is a schematic illustration of an example graphical user interface screen for managing QA resources.

2. A listing of current Reasons for Return will display. (See FIG. 99—Managing QA Resources).

3. To enter a new Reason For Return, go to the bottom of the Results Grid and enter information (See FIG. 100—Entering New Reason For Return).

Descriptive name for Reason For Return

Location for where items returned for that reason should be directed.

Selected RA Type. NOTE: If same Reason for Return can be applied to different RA Types, the Reason must be entered for EACH RA Type.

Enter comment, if appropriate.

4. Click the Save Icon to save the entry.

5. To edit a Reason for Return, click the Pencil Icon, make changes, and then click the Save Icon to save the changes.

Additional Functionality

Present invention embodiments may further provide other functionality pertaining to tracking of equipment or other items. The system (e.g., via the tracking and other modules) may provide various interfaces (e.g., interface screens, etc.) to interact with users and manage information. For example, the system may accommodate tracking of and access to Rental Agreements, Warranty and Service Agreements related to serial numbered Equipment. In this case, the system may provide appropriate interfaces to receive and provide corresponding information.

The system may accommodate online access for various tasks. For example, online access may be provided for completion of Bills of Lading (BOL) for equipment placement at customer locations, and Pick-up Documents for equipment removal from customer locations.

In addition, the system may provide inventory management support forms. In this case, Sales Executives and departments conduct their inventory, and enter their equipment information. The system would automatically notify them of when they're entering information that does not correlate with data to assist in resolution of inventory tracking errors.

The equipment tracking system may employ a Quick Response (QR) type code in combination with mobile devices. In this case, medical devices tracked by the system include a label with a QR code (preferably at least version 4). The QR Code can be read by various mobile devices (e.g., smartphone, etc.). The mobile devices utilize a mobile application to scan the medical device QR code. The mobile application utilizes Global Positioning System (GPS) information ascertained from the GPS capability of the mobile device to find the current location of the medical device and enable the system to prompt the user for the placement type. The mobile application uploads the information to the equipment tracking system. The system server creates the new placement with the uploaded information. The system selects the correct location based on the OPS coordinates, and checks that the Placement Type submitted was allowed based on the Location type and Ownership.

A user may use the mobile application to perform inventory counts by quickly scanning all medical device codes in an inventory location. Once the medical devices are scanned, the inventory data is uploaded and reconciled in the system server. When the equipment is delivered, instead of the current forms, the mobile application prompts for a receipt and appropriate information. The mobile application may be supported by Android mobile OS, and may be sold to users with a configuration package support plan.

The equipment tracking system may further employ Global Positioning System (GPS) capability. In particular, a GPS module chip (e.g., FV-M8 receiver module) may be added to the medical devices. The medical device locks onto all satellites in range, and logs its location in the internal memory of the medical device. The medical device establishes a wireless connection through a local Wireless network to use a Web Service to communicate to the configured equipment tracking system server. The medical device uploads time/location data points. The system, having a database of configured locations, updates the location of the medical device.

The system server checks the uploaded data, and logs the new placement. An alert is sent in response to the absence of an authorized scan within a predetermined time period (e.g., 4 hours, etc.). A backup battery may be installed in case the medical device lost power that would power the GPS module/subsystem. In case the medical device does not have access to the Internet, the medical device switches to a Global System for Mobile Communications (GSM) wireless card to connect to the equipment tracking system. When no Internet or Local wireless access is available, a user may access the data log through a Universal Serial Bus (USB) interface, and upload the data to the equipment tracking system.

In addition, die equipment tracking system may employ third party data connectors. Specifically, the equipment tracking system interacts with Accounting and Customer Relationship Management (CRM) systems to provide complete location and equipment information. The equipment tracking system uses an Accounting xml web service and a CRM xml web service to provide interconnecting data solutions between any database-based applications. A web service Extensible Markup Language (XML) client is installed in the Accounting or CRM server/network and queries the application's database. For security reasons, the client application queries a template view that only contains authorized data. The client XML application establishes an encrypted Secure Sockets Layer (SSL) channel out to the equipment tracking system server location to update the system data. Users of the equipment tracking system are able to see the data in the equipment tracking system's windows and through the included reports. The data is synchronized as per user requirements. The use of XML web services provides greater flexibility than the current direct Structured Query Language (SQL) server queries.

Database Fields

| Field Name | General Description |
| --- | --- |
| Catalogue | Groups of Models. A logical way of grouping types of Equipment. |
| Catalogue Description | Description of a Catalogue. |
| City | Name of the city where the Equipment is located. Each Location ID/Location has an associated City. |
| Condition | Condition code for equipment as determined by Manufacturing. N = Newly delivered finished good. A = Equipment is in the same cosmetic condition as New (N). B = Equipment has cosmetic condition of less than NEW, but functions the same as NEW. C = Equipment was previously sold. |
| Configuration | Description of Model |
| Country | Complete name of a Country where equipment is located. |
| Country | Standard abbreviation for the country. Used in search results rather than displaying the full country name used in the search criteria section for "RESOURCES LOCATIONS" |
| Current Location | The Location ID and Location Name for the current placement of the equipment. |
| Current RA | The RA Number associated with the equipment device whether it is a Replacement piece of Equipment or the Equipment being returned. This field is automatically cleared when the RA is Closed. |
| EA | Equipment Agreement(s) Details for the Location ID. Includes EA Attachments, EA date, and Equipment quantities by model associated with the EA |
| EA Attachment | Pdf version of the Equipment Agreement for the Location ID |
| EA Date | Date of the EA |
| EA Notes | Notes pertinent to the EA |
| Equipment Notes | Additional optional comments on a specific piece of equipment |
| LinkedEq | Model information (Model number, serial number etc.) for equipment linked to another piece of equipment. |
| Loc ID | Unique identifier for each physical location where equipment is currently or has been located. Rep Inventory and Company related locations use the format NNNXX. Example: 001ST is STOCK. Hospital and Customer related locations use the format of two letter State (or |

-continued

| Field Name | General Description |
|---|---|
| | letter for Country) and a 3 digit identifier. Example: MD003. Rep Inventory and Company locations use a 3 digit identifier followed by a 2 letter code. |
| Loc Name | Name of the Location |
| Loc Notes | Notes describing the location or pertinent information on the location. |
| Loc Class | Defines the type of location for logical groupings. Examples: Hospital, Company, Rep Inventory and Disposed (Scrapped or lost equipment). |
| Location | Combination of Location ID, Location Name. Displayed when choosing "Details" for a piece of equipment to obtain Placement History. |
| Loc Class Description | A description of the Location Class including appropriate Placement Types for use with the Location Class. |
| MFG Date Code | Original date code for an individual piece of equipment manufactured based on code criteria |
| Model Description | This is a short description of a model. |
| Model or Model Number | Model numbers. |
| On/Off GL | Indicates equipment status related to General Ledger. Used by Accountants. |
| PL Date | Placement Date - Identifies on what date the specific piece of equipment was placed into a location. Format is mm/dd/yy |
| PL Notes | Notes describing the particular (individual) placement |
| PL Type | Identifies under what terms that piece of equipment is placed at a location, for example: Loan, Eval, Sold |
| PL Type Description | Describes the use of the Placement Type |
| Product Level | Description of Model |
| Quantity | The number of items associated with placement of equipment. Defaults to 1 for Serial Numbered equipment. Can be greater than 1 for tracked non-serial numbered equipment such as stands and mounting kits. |
| Region | Region is predefined area compose of several Sales Territories linked to one Sales Manager |
| Region Description | Region description is a extended description of a region (e.g. Southeast, West,) |
| Sales Admin | Sales Administrator's name |
| Sales Manager | Sales Manager's name |
| Sales Person | Sales Executive's name associated with a Territory ID. |
| Serial No | Unique number assigned by the manufacturer for an individual piece of equipment |
| State | Name of the State |
| Status (Catalogue) | Status of the Catalogue (Active or inactive) |
| Status (Locations) | Designates if the Location is Active or Inactive. Inactive locations remain within the database for historical placement information, but are no longer available in pull down selection menus for placing equipment. |
| Status (Model) | Status of Model (Active or Inactive). Identifies if equipment continues to be manufactured under that Model. |
| Status (Placement Types) | Defines if Placement Type is still available for data entry. The Placement Type will still appear in SEARCH pull downs menus for Placement History information. |
| Territory | Identifier for a sales territory |
| SA Expiration | Date of Service Agreement Expiration. Data: 01/01/0001 in field indicates no SA is in place. |
| Warranty Expiration | Date of Warranty Expiration. Data: 01/01/0001 in field indicates no SA is in place. |
| Ownership | Identifies the owner of the Equipment: Customer, Company, Rental or None. |

Variations

It will be appreciated that the embodiments described above and illustrated in the drawings represent only a few of the many ways of implementing embodiments for tracking equipment or other items.

The topology or environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems (e.g., server systems, client systems, etc.) employed by the present invention embodiments may be implemented by any number of any personal or other type of computer or processing system (e.g., IBM-compatible, laptop, PDA, mobile devices, etc.), and may include any commercially available operating system and any commercially available or custom software (e.g., browser software, communications software, server software, tracking software, etc.). These systems may include any types of monitors and input devices (e.g., keyboard, mouse, voice recognition, etc.) to enter and/or view information.

It is to be understood that the software (e.g., tracking and other modules, etc.) of the present invention embodiments may be implemented in any desired computer language and could be developed by one of ordinary skill in the computer arts based on the functional descriptions contained in the specification and flow charts and/or diagrams illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts and/or diagrams may be modified in any manner that accomplishes the functions described herein. In addition, the functions in the flow charts and/or diagrams or description may be performed in any order that accomplishes a desired operation.

The software of the present invention embodiments (e.g., tracking and other modules, etc.) may be available on a recordable or computer usable medium (e.g., magnetic or optical mediums, magneto-optic mediums, CD-ROM, DVD, memory devices, etc.) for use on stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The present invention embodiments may employ any number of any conventional or other databases, data stores or storage structures (e.g., files, databases, data structures, data or other repositories, etc.) to store information (e.g., relating to the equipment or other items, etc.). The database system may be implemented by any number of any conventional or other databases, data stores or storage structures (e.g., files, databases, data structures, data or other repositories, etc.) to store any desired information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information (e.g., obtaining information for the desired equipment, providing the report, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The reports may include any information arranged in any fashion (e.g., pertaining to equipment or other information, etc.). The report may be configurable based on rules or other criteria to provide desired information to a user (e.g., certain equipment, dates, locations, etc.).

The present invention embodiments are not limited to the specific computer systems, tasks, or algorithms described above, but may be utilized within any system for selectively processing and tracking various types of items.

From the foregoing description, it will be appreciated that the invention makes available a novel method and system for tracking equipment, wherein a tool tracks manufactured and other products from cradle to grave.

Having described preferred embodiments of a new and improved method and system for tracking equipment, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for tracking items comprising:
   a plurality of position sensing devices each associated with a corresponding item to detect a geographic location of the corresponding item;
   a computer system including at least one processor configured to:
      provide a user interface to interact with a user;
      periodically communicate with a position sensing device of an item to obtain the detected geographic location for the item and generate an alert in response to an absence of a communication to the periodic communicating from the position sensing device for a predetermined time interval indicating an unknown location for the item, wherein the position sensing device communicates over a wireless network to utilize a network service to periodically communicate with the computer system;
      receive information concerning the item from the user interface and position sensing device including the detected geographic location;
      maintain one or more agreements associated with the item, wherein the agreements include one or more of an equipment agreement, a rental agreement, a warranty agreement, and a service agreement;
      analyze an agreement to determine a quantity of permitted items for each location covered by the agreement;
      compare the determined quantity of permitted items to a quantity of items at each corresponding location covered by the agreement;
      color-code on the user interface a location identifier indicating a corresponding location covered by the agreement to specify compliance of that location with respect to the determined quantity of permitted items indicated by the agreement; and
      process the received information and track placement of the item for a duration of an item operational life, wherein the tracking of item placement includes tracking of item locations and times of placement and removal of the item from those locations.

2. The system of claim 1, wherein the item includes at least one of medical devices, parts, and accessories.

3. The system of claim 1, wherein the at least one processor is further configured to:
   link the item with another item being tracked; and retrieve and provide information for the linked item based on the linking.

4. The system of claim 1, wherein the at least one processor is further configured to:
determine a placement history based on the tracked item placement; and
export the placement history to a file.

5. The system of claim 1, wherein the position sensing device of an item includes:
a mobile device including a GPS capability to determine the item location and provide the item location to the computer system.

6. The system of claim 1, wherein the item includes the position sensing device in the form of a GPS module to determine the item location.

7. The system of claim 1, wherein the at least one processor is further configured to:
create and maintain a complaint including incident information for the item indicating an operational defect of the item encountered by a user, replacement information indicating a replacement item, and a return authorization enabling return of the item; and
link the complaint with the item and retrieve information for the complaint based on the link between the item and the complaint.

8. The system of claim 7, wherein the at least one processor is further configured to:
maintain one or more documents associated with the complaint.

9. The system of claim 1, wherein the at least one processor is further configured to:
track a returned item placed into stock.

10. The system of claim 9, wherein the at least one processor is further configured to:
track a replacement item that replaces the returned item.

11. The system of claim 1, wherein the at least one processor is further configured to:
interact with an external system to provide information pertaining to the item.

12. A method of tracking items, wherein a plurality of position sensing devices are each associated with a corresponding item to detect a geographic location of the corresponding item, the method comprising:
(a) providing a user interface, via a processor, to interact with a user and periodically communicating with a position sensing device of an item, via the processor, to obtain the detected geographic location for the item and generating an alert in response to an absence of a communication to the periodic communicating from the position sensing device for a predetermined time interval indicating an unknown location for the item, wherein the position sensing device communicates over a wireless network to utilize a network service to periodically communicate with the processor;
(b) receiving information concerning the item from the user interface and position sensing device including the detected geographic location and processing the received information, via the processor, to track placement of the item for a duration of an item operational life, wherein the tracking of item placement includes:
(b.1) tracking item locations and times of placement and removal of the item from those locations;
(b.2) maintaining one or more agreements associated with the item, wherein the agreements include one or more of an equipment agreement, a rental agreement, a warranty agreement, and a service agreement;
(b.3) analyzing an agreement to determine a quantity of permitted items for each location covered by the agreement;
(b.4) comparing the determined quantity of permitted items to a quantity of items at each corresponding location covered by the agreement; and
(b.5) color-coding on the user interface a location identifier indicating a corresponding location covered by the agreement to specify compliance of that location with respect to the determined quantity of permitted items indicated by the agreement.

13. The method of claim 12, wherein the item includes at least one of medical devices, parts, and accessories.

14. The method of claim 12, wherein step (b) further includes:
linking the item with another item being tracked; and
retrieving and providing information for the linked item based on the linking.

15. The method of claim 12, wherein step (b) further includes:
determining a placement history based on the tracked item placement; and
exporting the placement history to a file.

16. The method of claim 12, wherein step (b) further includes:
receiving the item location from the position sensing device including a mobile device including a GPS capability.

17. The method of claim 12, wherein the item includes the position sensing device in the form of a GPS module to determine item location, and step (b) further includes:
receiving the item location from the GPS module.

18. The method of claim 12, further including:
(c) creating and maintaining, via the processor, a complaint including incident information for the item indicating an operational defect of the item encountered by a user, replacement information indicating a replacement item, and a return authorization enabling return of the item; and
(d) linking the complaint with the item and retrieving information for the complaint based on the link between the item and the complaint.

19. The method of claim 18, wherein step (c) further includes:
(c.1) maintaining one or more documents associated with the complaint.

20. The method of claim 12, wherein step (b) further includes:
tracking a returned item placed into stock.

21. The method of claim 20, wherein step (b) further includes:
tracking a replacement item that replaces the returned item.

22. The method of claim 12, further including:
interacting with an external system to provide information pertaining to the item.

23. A device for tracking items, wherein a plurality of position sensing devices are each associated with a corresponding item to detect a geographic location of the corresponding item, the device comprising:
a non-transitory computer useable medium having computer readable program code recorded thereon, the computer readable program code comprising computer readable program code that when executed by a processor is configured to:
provide a user interface to interact with a user;

periodically communicate with a position sensing device of an item to obtain the detected geographic location for the item and generate an alert in response to an absence of a communication to the periodic communicating from the position sensing device for a predetermined time interval indicating an unknown location for the item, wherein the position sensing device communicates over a wireless network to utilize a network service to periodically communicate with the processor;

receive information concerning the item from the user interface and position sensing device including the detected geographic location;

maintain one or more agreements associated with the item, wherein the agreements include one or more of an equipment agreement, a rental agreement, a warranty agreement, and a service agreement;

analyze an agreement to determine a quantity of permitted items for each location covered by the agreement;

compare the determined quantity of permitted items to a quantity of items at each corresponding location covered by the agreement;

color-code on the user interface a location identifier indicating a corresponding location covered by the agreement to specify compliance of that location with respect to the determined quantity of permitted items indicated by the agreement; and process the received information to track placement of the item for a duration of an item operational life, wherein the tracking of item placement includes tracking of item locations and times of placement and removal of the item from those locations.

24. The device of claim 23, wherein the item includes at least one of medical devices, parts, and accessories.

25. The device of claim 23, wherein the computer readable program code further comprises computer readable program code configured to:

link the item with another item being tracked; and retrieve and provide information for the linked item based on the linking.

26. The device of claim 23, wherein the computer readable program code further comprises computer readable program code configured to:

determine a placement history based on the tracked item placement; and export the placement history to a file.

27. The device of claim 23, wherein the computer readable program code further comprises computer readable program code configured to:

receive the item location from the position sensing device including a mobile device including a GPS capability.

28. The device of claim 23, wherein the item includes the position sensing device in the form of a GPS module and the computer readable program code further comprises computer readable program code configured to:

receive the item location from the GPS module.

29. The device of claim 23, wherein the computer readable program code further comprises computer readable program code configured to:

create and maintain a complaint including incident information for the item indicating an operational defect of the item encountered by a user, replacement information indicating a replacement item, and a return authorization enabling return of the item; and link the complaint with the item and retrieve information for the complaint based on the link between the item and the complaint.

30. The device of claim 29, wherein the computer readable program code further comprises computer readable program code configured to:

maintain one or more documents associated with the complaint.

31. The device of claim 23, wherein the computer readable program code further comprises computer readable program code configured to:

track a returned item placed into stock.

32. The device of claim 31, wherein the computer readable program code further comprises computer readable program code configured to:

track a replacement item that replaces the returned item.

33. The device of claim 23, wherein the computer readable program code further comprises computer readable program code configured to:

interact with an external system to provide information pertaining to the item.

* * * * *